United States Patent
Malik et al.

(10) Patent No.: US 6,438,409 B1
(45) Date of Patent: Aug. 20, 2002

(54) METHODS OF CHARACTERISING VENTRICULAR OPERATIONS AND APPLICATIONS THEREOF

(75) Inventors: Marek Malik, London (GB); Burak Acar, Ankara (TR); Velislav Nikolaev Batchvarov, London (GB)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/534,454

(22) Filed: Mar. 24, 2000

(30) Foreign Application Priority Data

Mar. 25, 1999 (GB) ................................. 9906951
Mar. 15, 2000 (GB) ................................. 0006235

(51) Int. Cl.[7] .......................................... A61B 5/0428
(52) U.S. Cl. ...................................... 600/512
(58) Field of Search ........................... 600/508, 509, 600/510, 512

(56) References Cited

U.S. PATENT DOCUMENTS

| | | | |
|---|---|---|---|
| 3,884,221 A | * | 5/1975 | Eastman |
| 4,697,597 A | * | 10/1987 | Sanz et al. |
| 5,331,966 A | * | 7/1994 | Bennett et al. |
| 5,437,285 A | | 8/1995 | Verrier et al. ............... 128/702 |
| 5,560,370 A | | 10/1996 | Verrier et al. ............... 128/705 |
| 5,792,065 A | | 8/1998 | Xue et al. .................... 600/516 |
| 5,803,084 A | * | 9/1998 | Olson |
| 5,842,997 A | | 12/1998 | Verrier et al. ............... 600/518 |
| 5,921,940 A | | 7/1999 | Verrier et al. ............... 600/518 |

OTHER PUBLICATIONS

"Determinants of Precordial QT Dispersion in Normal Subjects" Lee et al, Journal of Electrocardiology, vol. 31 Supplement, pp. 128–133.

"QT Dispersion as an Attribute of T–loop Morphology" Kors et al., Circulations 1999; 99, pp. 1458–1463.

* cited by examiner

*Primary Examiner*—Scott M. Getzow
(74) *Attorney, Agent, or Firm*—Thomas F. Woods; Eric R. Waldkoetter; Thomas G. Berry

(57) ABSTRACT

New methods of characterising ventricular operations by measuring propagation characterisics of the repolarisation wavefront (the T wave) are disclosed, the methods use new descriptions of T wave Morphology Dispersion (TMD), Total Cosin R__ to __T (TCRT) and T wave energy residium to quantify the wavefront characteristics, these descriptors measure the spatial variability of the T wave Morphology, the vector deviations between the depolarisation and repolarisation wavefronts and the energy of the non-dipolar components of the ECG vector respectively. TCRT also provides a responsive descriptor for measuring autonomic tone. As such, has applications for improved pacing and autonomic nervous system monitors.

41 Claims, 22 Drawing Sheets

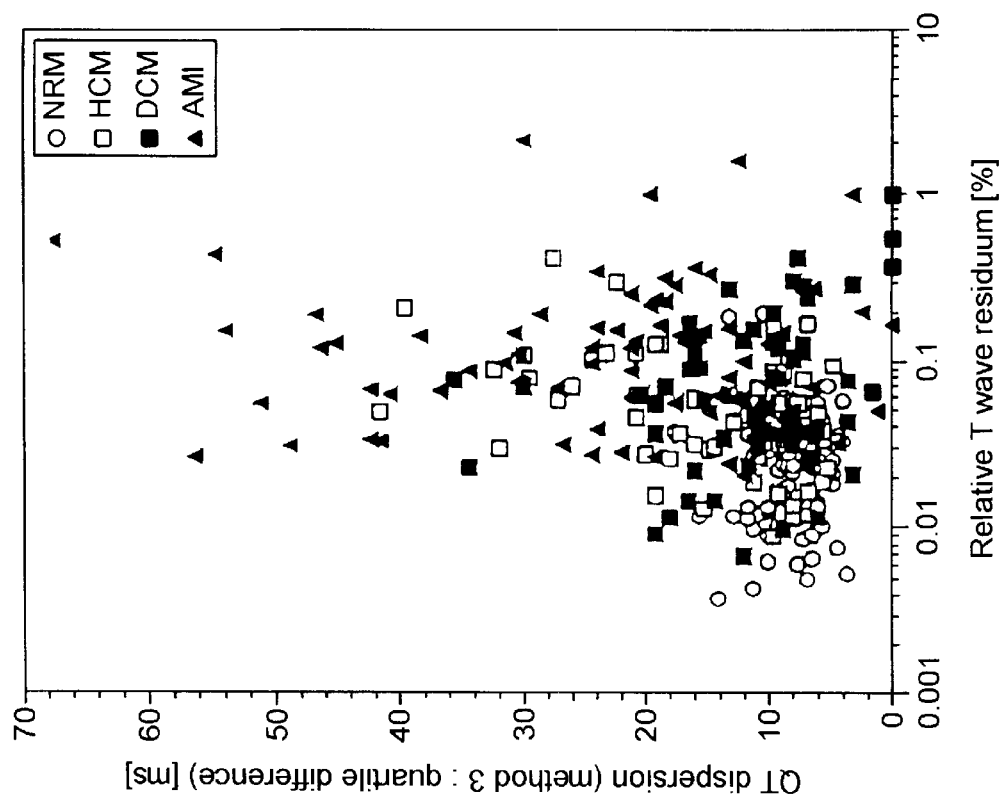
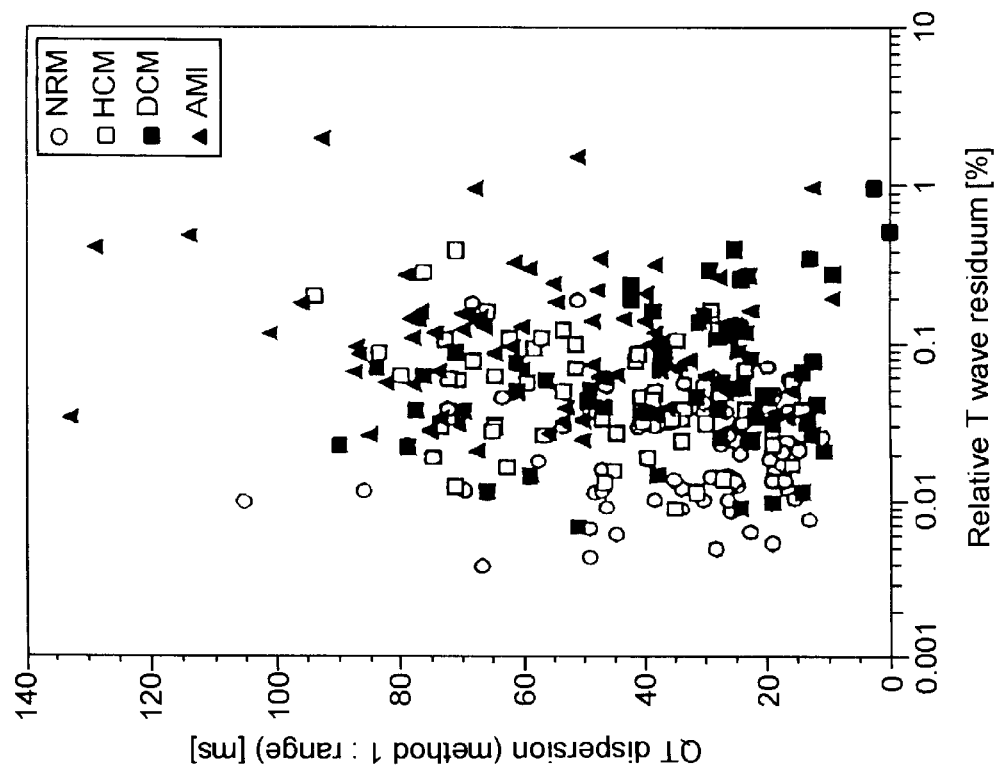

METHODS OF CHARACTERISING VENTRICULAR OPERATIONS AND APPLICATIONS THEREOF

FIELD OF THE INVENTION

The present inventions relate to methods of characterising ventricular operation. In particular, but not exclusively, they relate to a system for quantifying abnormalities of an electrocardiogram and to a method and an apparatus for measuring such abnormalities. The present inventions also extend to an operating system for a computer, to a computer program and to media having stored thereon a computer program for putting the inventions into effect. Other applications include use of the algorithms in pacemakers and heart monitors. The inventions share a common link of characterising differences in the wavefront of the repolarisation wave.

BACKGROUND OF THE INVENTION

Electrocardiographic patterns of the heart's movements have been well studied. An electrocardiogram (ECG) records the changes in electrical potential associated with the spread of depolarisation and repolarisation through the heart muscle. In a normal healthy patient, depolarisation starts in an area of the right atrium called the sinoatrial node and spreads through the atrioventricular node and into the ventricular muscle via specialised conduction tissue, causing the two atria and the two ventricles to contract. During repolarisation, the atria and ventricles relax and refill with blood. The depolarisation of the atria is responsible for the P wave of an ECG and depolarisation of the ventricles results in the QRS complex. Repolarisation of the atria coincides with the QRS complex so it is not seen. Repolarisation of the ventricles, however, is seen as the T wave.

ECG's are typically recorded using a standard arrangement of 12 leads, 6 (the I, II, III, VR, VL, VF leads) looking at the heart in different directions in an approximately vertical plane of a body in an upright position and 6 (the V1, V2, V3, V4, V5 and V6 leads) looking at the heart in different directions in an approximately horizontal plane. Using such an arrangement of leads, the spread of the waves of electrical potential associated with depolarisation and repolarisation through the three dimensional space of the body, can be recorded.

The spread of these waves through the heart is often described by vectors. For example, the average direction of spread of the depolarisation wave through the ventricles as seen from the front of the body is called the cardiac axis and the direction of this axis has long been used to indicate different abnormalities of the heart.

To study abnormalities associated with ventricular repolarisation, a number of data processing techniques have been proposed to measure, for example, the QT interval, i.e. the interval between the beginning of depolarisation and the end of repolarisation of the ventricles. Interlead variability of the QT interval durations in standard 12 lead ECG recordings has also been studied. However, whilst these measurements may provide some diagnostic assistance, concerns have been raised about the poor reproducibility of results.

Studies have also tried to quantify the inhomogeneities in the ventricular repolarisation patterns by evaluating the complexity of the T wave morphology using eigenvalues associated with the principal components of ECG, measured over a period of 24 hours. The direction of the ECG vector during T wave in the 3D physical (x,y,z) has also been shown to have some predictive value.

However, there is still a need for further measurements which may provide a more accurate technique for identifying certain conditions, particularly those which affect repolarisation of the ventricles. A problem with known methods, for example, is that they only quantify global variations in the T wave rather than spatial variations in individual waves, that is the synchronicity of the T wave, as observed from different locations on the body, is not observed.

SUMMARY OF THE INVENTION

Thus, viewed from a first broad aspect, a first invention described herein provides a method of quantifying abnormalities of an electrocardiogram observing repolarisation patterns from different locations on a body, wherein the abnormalities are quantified by a measure of the synchronicity of the repolarisation patterns as observed from those different locations on the body. In other words, this is a measure of the homogenity of the spread of repolarisation waves.

Unlike depolarisation of the heart muscle, the repolarisation of individual cells is not triggered by neighbouring cells but is instead a time dependent process. If repolarisation patterns, as observed in different locations on the body, lack synchronicity, then this can be indicative of certain heart complications.

By quantifying these abnormalities, it may be possible to use the data to assist with diagnosis or to identify patients at most risk or classify them into different categories of risk. This may be of great importance in determining whether certain treatments should be offered to a patient, for example. The data could also be used to trigger an alert in a monitoring device.

The homogenity of the spread of repolarisation waves can be measured by quantifying the spatial variability of the ventricular repolarisation patterns i.e. the spatial variability of the T wave.

Thus viewed from a second aspect, the first invention provides a method of characterising ventricular operation, comprising the steps of:
recording a signal monitoring the propagation of a repolarisation wave;
determining a vector which is representative of the wavefront of the repolarisation wave; and
determining a measure of the spatial variation of the repolarisation wavefront.

In one preferred embodiment, it provideed a method of quantifying abnormalities of ventricular repolarisation by determining a measure of the spatial T wave morphology variation.

Preferably the spatial T wave morphology variation is quantified by measuring the T wave Morphology Dispersion.

Preferably this is achieved by determining vectors describing the contributions which the signals from each lead (often referred to as the channels of an ECG) makes to the T wave. The angles between these vectors are then calculated and a mean value is determined. This mean value of the angles provides a measure of the spatial T wave morphology variation. The smaller the value, the closer the T wave morphologies will be in the signals of the individual leads.

Preferably the ECG signal is morphologically filtered to improve the signal to noise ratio. In one preferred embodiment, this consists of the steps of decomposing the T wave using a technique such as Singular Value Decomposition, filtering by keeping only the two most significant signal components, and applying a DC compensation. A preferred DC compensation is provided by subtracting an average of the start and end signal components during the QRS complex and T wave. The morphologically filtered T wave is then preferably rescaled to equalise energies in the different component directions. The corresponding reconstruction parameters are calculated to determine the vector contributions of each of the ECG leads. The angles between each pair of the vector contributions is then calculated and the mean determined. Most preferably the contribution in respect of lead V1 is ignored because the T wave morphology in this lead is generally different than that of other channels, irrespective of any clinical background, mainly due to the position of the V1 electrode, and by ignoring this component, it has the effect of enhancing the predictive value of the T wave morphology dispersion descriptor.

The main reason for initially decomposing the data matrix is to find an optimum representation of the ECG signals upon which the measurements can be performed. In this way, the system does not use the standard XYZ axes of the body but finds an optimally constructed orthogonal system to represent the 12 lead ECG. In a preferred embodiment, therefore, the first invention can be seen as providing a method for looking at the vector representation of each of the standard electrocardiographic leads in an optimum dimensional vector space in which the ECG signals can be represented and comparing the angles between the vectors of individual standard leads.

The spatial T wave morphology variation may provide a useful descriptor when it is determined for the whole of the T wave, the first half of the T wave, the second half of the T wave or any other portion or combination of portions of the T wave.

The present inventions are not limited to standard 12 lead electrocardiograms, although this is preferred, but extend to electrocardiograms produced from only three or more leads. In certain applications, it may be useful to use the electrodes of a pacemaker to record an electrocardiogram signal. In such situations, the positions and numbers of the electrodes would not usually correspond with the arrangement of standard leads, for example. Whilst it is preferred to view the waves in three dimensions, because, research up to date suggests that approximately 99% of 12-lead ECG energy can be represented in a 3D space, the inventions are applicable to situations where the heart is viewed in any dimensions, greater than or equal to two.

In a conventional 12 lead ECG, only 8 (I, II, V1, V2, V3, V4, V5 and V6) of the signals are independent. The other 4 signals (III, VR, VL, VF) are algebraically dependent on the other leads so, if desired, may be generated by data processing methods rather than measured as such. As explained above, it is most preferred to use signals only from leads I, II, V2, V3, V4, V5 and V6, and to ignore the signal from V1 in order to concentrate the abnormalities seen in the T wave. The position of the leads, although having an effect on the value produced by the descriptors, is not critical to the inventions. Whilst the inventions may be described with reference to the standard ECG leads, this is not intended to limit the inventions to just those positions. These positions are preferred, however, since they have become "standard" measuring points throughout the world.

It has also been found that comparing the spread of depolarisation through the ventricles with the spread of repolarisation can provide useful information.

Thus, in accordance with a first aspect of a second invention described herein, there is provided a method of characterising ventricular operation, comprising the steps of:

recording a signal monitoring the propagation of depolarisation and repolarisation waves;

determining vectors which are representative of the direction of the wavefronts of the depolarisation and repolarisation waves; and determining a measure of the deviation between those vectors.

Thus, the present invention can be seen to provide a method of quantifying abnormalities of an electrocardiogram observing the spread of depolarisation and repolarisation waves through the ventricles, wherein the abnormalities are quantified by comparing a property of the depolarisation wave with a property of the repolarisation wave where preferably the abnormalities are quantified by a measure of the vector deviation between the ventricular depolarisation and the ventricular repolarisation waves.

Described in other terms, a method of the second invention may compare the direction of the depolarisation wave (i.e., the QRS part of the ECG) with the repolarisation wave (i.e. the T wave). This may be achieved by comparing the angles between principal vectors of the ventricular depolarisation and repolarisation waves, comparing the angles between a principal vector of the ventricular depolarisation wave and the ECG vectors during ventricular repolarisation, comparing the angles between the ECG vectors during ventricular depolarisation and a principal vector of the ventricular repolarisation wave, or comparing the angles between the ECG vectors during ventricular depolarisation with those during ventricular repolarisation. The angles may be compared for the whole of a wave or just a portion of a wave or any combination of portions of the waves. For example, in one embodiment the angles between the depolarisation and repolarisation vectors are compared for portions of the waves which span the peak energy values, but it may be preferred in some instances to look at and compare other portions of the waves which would correspond to depolarisation and repolarisation occurring in different regions of the heart muscle.

Preferably the vector deviations are determined using the optimally constructed representation of the ECG signals discussed above.

In healthy patients, the principal vectors would, generally speaking, only deviate by up to about 30°. In patients having hypertropic cardiomyopathy (HCM), for example, vector deviations greater than 90° may be seen. These deviations can be distinguished over inversion of the T wave, for example, which would result in angles closer to 180°.

Again it is preferred to conduct certain data processing steps before the angles of the vectors describing the QRS complex and T wave are compared. Firstly the data matrix describing the signal is decomposed, again preferably by Singular Value Decomposition. The decomposed signal components are ranked in order of their significance in terms of the energy of the ECG vector that they represent. Thus the First signal component contains the most energy in a first direction. The second signal component contains the next most energy in a second direction which is perpendicular to the first. The third signal component contains the next most energy in a third direction which is perpendicular to the first and second directions. Where eight of the independent ECG channels are recorded, the ECG vector can be decomposed into an eight dimensional orthogonal space. When measuring the vector deviations of depolarisation and repolarisation vectors, a good approximation may be made by only measuring the first two or three of the decomposed signal components since these can account for more than 99% of the total energy of the 12-lead ECG signal. The QRS complex and T wave are localised by making use of the variation of the instantaneous ECG energy. The method does not depend on accurate localisation of the QRS complex and the T wave. This method of detection provides an example of many possible ways.

Both the vector representations of the QRS complex and T wave follow an approximate loop in the constructed space. Vectors can be determined which represent the maximum energy of the T wave and QRS complex, and the angles between them compared. More preferably a vector describing the maximum energy of the T wave is compared to the vectors describing the QRS complex for a set of points at the peak of ventricular repolarisation (which, for example, can be determined by tracing the instantaneous ECG energy). In the most preferred embodiment, the vector deviation between the depolarisation and repolarisation waves is measured as the average of the cosines of the angles between the vector describing the maximum energy of the T wave and the vector describing the wavefront of the QRS complex, the angles being determined in constructed space. The measurement of the vector deviation in terms of the cosine of the angle is referred to herein as TCRT—total cosine R_to _T.

The second invention introduces the idea of considering depolarisation and repolarisation processes of the heart muscle simultaneously and comparing them. While it may be described as a comparison of ECG vectors observed during these processes, in an appropriately constructed vector space, this is not intended to limit the invention to just ECG vector comparison and to processing of standard ECG leads.

Comparing the propagation directions of depolarisation and repolarisation has revealed some interesting detection properties. In particular, TCRT has proved to be more sensitive to autonomic changes of ventricular repolarisation than other known descriptors such as ventricular gradient and QT dispersion. From investigations, it has been found that TCRT responds quickly to changes in the position and activity of the patient with distinct ranges or levels of descriptor values being obtainable for different autonomic tones. This descriptor may be used to check for abnormalities in ventricular depolarisation and repolarisation under different autonomic conditions, thereby providing a fuller picture to assist with diagnosing defects. TCRT has been found to be useful as a predictor for mortality in patients which have suffered acute myocardial infarction and as a predictor for arrythmias. The descriptor could be used in a monitor carried by the patient or in equipment in an intensive care unit to warn the patient or medic by means of an alarm when the TCRT is pushed to a danger level as a result of changes in the autonomic tone, for example, caused through exercise or trauma. TCRT could also be used to check that the patient has a properly functioning autonomic system, for example, prior to the administration of anaesthetic agents before surgery.

TCRT is in effect able to provide a measure of the autonomic tone of a patient. It could be used to control pacing of a pacemaker making it more responsive to the patient's needs by responding to changes in the autonomic tone. TCRT is increased by physical or emotional stress during fixed rate pacing and is decreased by an increase in pacing rate. TCRT could be implanted in a closed loop rate-adaptive feedback system. At times of physical or emotional stress TCRT would increase, triggering an increased pacing rate to decrease TCRT to resting level.

TCRT could be used to monitor the effect of certain drugs and the way in which they effect the autonomic system. When testing drugs which prolong the QT interval, TCRT could be used to monitor the patient and raise an alarm arrythmias are predicted or detected. It could be used to monitor changes in electrolyte of the body and other conduction phenonoma. It could even be used to control a drug delivery mechanism, administering certain drugs as heart function abnormalities are detected or in response to changes in the autonomic tone.

Conditions such as ischemia, as well as most illnesses, will have an effect oil the autonomic tone of the patient. TCRT could be used to assist in the prediction of ischemia or in the monitoring of the progression of a disease, for example, in heart failure patients, by providing an indication of the autonomic tone as well as changes in direction of the repolarisation wavefront. TCRT may be able to observe autonomic changes caused by the onset of ischemia before ST segment changes are observable on an ECG or pain is felt by the patient. It may also be useful in the monitoring of patients suffering from epilepsy, providing an early warning of heart function abnormalities. The autonomic tone could be observed to detect hypoxy conditions in a patient prone to fitting.

It should be noted that the possibilities mentioned above with reference to TCRT are not intended to be inferred as limiting the present invention to the preferred situation where TCRT is the average of the cosines of the angles between the vector describing the maximum energy of the T wave and the vector describing the wavefront of the QRS complex. For example, TCRT may compare the angles between the sets of vectors describing the depolarisation and repolarisation wavefronts with respect to time or may compare the vectors describing the maximum energy of depolarisation and repolarisation to each other. While the use of cosine provides an effective way of separating the angles between the vectors associated with abnormalities from those observed in normal patients, other operators may be used to separate the data.

As mentioned above, of the standard 12 lead ECG signals, 8 are independent. Thus, it is possible to describe the T wave as an 8-by-n matrix M, with each row corresponding to a standard ECG channel (I, II, V1, V2, V3, V4, V5, V6) and n being the number of samples. Performing Singular Value Decomposition on the matrix M generates a signal vector representing the progress of a T wave in 8 dimensions, where each dimension can be regarded as a component of the signal, associated with a fraction of the total energy of 12-lead ECG. For most purposes, as mentioned above, only the first two or three components are normally used, since these may account for over 99% of the total T wave energy in 12-lead ECG signals. However it has been found that comparing the energy of the most significant components with the energy of the other components provides a further useful descriptor that can be used during analysis of the ECG.

Thus according to a third invention described herein, there is provided a method of quantifying abnormalities of an electrocardiogram having a plurality of independent signals, in which the signals are decomposed to obtain a signal vector having two or more signal vector components, wherein the energy of the components is compared.

Preferably, the components are arranged substantially in order of decreasing signal energy and the energy of the most significant components representing the majority of the signal energy is compared to the energy of the other components. Preferably the electrocardiogram records 8 independent signals and the signal vector has 8 components and the first 3 components of the signal vector, thus constructed, represents the majority of the signal energy.

The third invention introduces the idea to transform the ECG signals into an optimally constructed space which represents the ECG energy in a minimum dimensional space of orthogonal components and to assess the residual energy that is left outside the three dimensional space of the first three signal components. In a possible implementation, as described above, this corresponds to assessing the relative values of the 3 highest singular values of the matrix M to the other singular values. The first three signal components represent the dipolar components of the ECG vector and the remaining signal components correspond to the non-dipolar components. By measuring the power in the orthogonal components outside the three dimensional space, it is possible to measure the power of the non-dipolar components which provides a measure of the local repolarisation abnormalities. However with a different set of input signals and/or different parts of the ECG signal, the separation/number of significant components may vary.

The inventions described above also extend to an apparatus which is programmed with an algorithm to process data from an ECG in accordance with any of the described inventive methods. The apparatus could be a computer, for example, programmed in a particular way or could be a plug-in box for an ECG apparatus or an ECG apparatus provided with means to calculate these descriptors and display the result to an operator. Furthermore, the inventions extend to an operating system or a computer program having an algorithm to process data from an ECG in accordance with the described methods and to media having such a computer program or operating system stored thereon. Thus, the inventions extend to a computer program product which is directly loadable into the internal memory of a digital computer, comprising software code portions for performing the steps of the afore-described methods when the product is run on a computer.

The present inventions will now be described by way of example only with reference to a preferred embodiment and the accompanying drawings, in which:

BRIEF DESCRIPTION OF THE DRAWINGS

FIGS. 20a and 20b show the lack of relationship between QT dispersion and relative T wave residuum data.

DETAILED DESCRIPTION OF THE PREFERRED EMBODIMENTS

Figure 1:
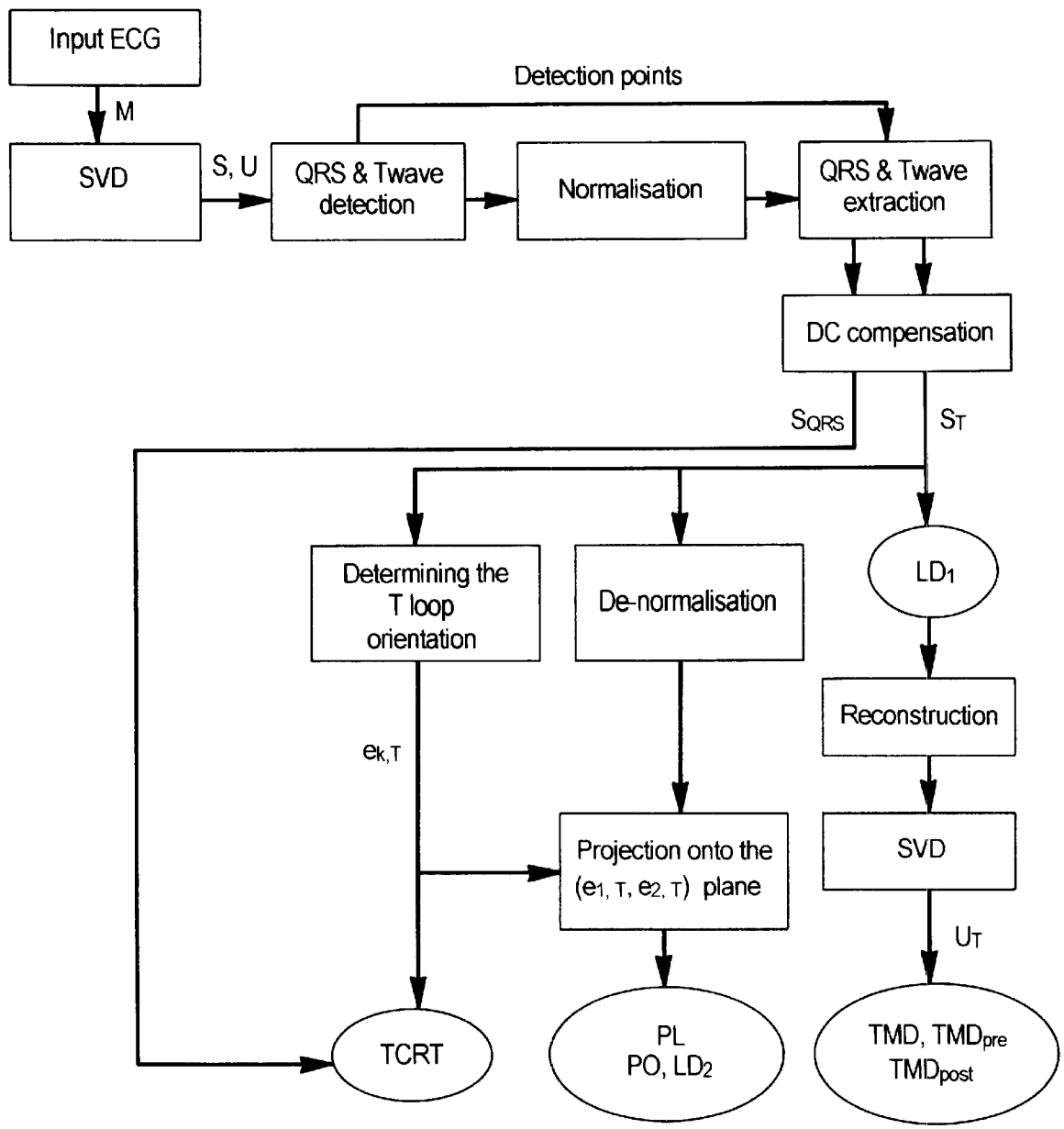
FIG. 1 shows a flow chart of preferred algorithms.

Three new approaches for the analysis of ventricular repolarisation in 12 lead electrocardiograms (ECG) will now be discussed in relation to a first case study: The spatial and the temporal variations of T wave morphology and the wavefront direction difference between the ventricular depolarisation and repolarisation waves. A minimum dimensional space, constructed by the Singular Value Decomposition of ECG signals, is used. The spatial variation characterises the morphology differences between standard leads. The temporal variation measures the change of interlead relations during ventricular repolarisation. The depolarisation and repolarisation patterns are compared using the principal interlead relations (wavefront directions) that characterises them. All of the descriptors are measured using the ECG vector in the constructed space and the singular vectors that define this space. None of the descriptors requires time domain measurements (e.g. the precise detection of the T wave offset), avoiding the inaccuracies associated with the conventional QT interval related parameters.

The new descriptors have been compared with the conventional measurements provided by a commercial system for an automatic evaluation of QT interval and QT dispersion in digitally recorded 12 lead ECGs (QT Guard, Marquette Medical Systems). The basic comparison used a set of 1100 normal ECGs. The short-term intrasubject reproducibility of the new descriptors was compared to that of the conventional measurements in a set of 760 ECGs recorded in 76 normal subjects and a set of 630 ECGs recorded in 63 patients with hyperthropic cardiomyopathy (10 serial recordings in each subject of both these sets). The discriminative power of the new and conventional parameters to distinguish normal and abnormal repolarisation patterns was compared using the same set.

The results showed that the new parameters do not correlate with the conventional ones (i.e. assess different ECG qualities), are generally more reproducible than the conventional parameters based on the QT interval measurement, and lead to a more significant separation between normal and abnormal ECGs both univariately and in multivariate regression models.

The present inventions are based on the hypothesis that spatial and temporal variations in T wave morphologies and the relation between the depolarisation and repolarisation patterns will offer new measures of repolarisation abnormalities. It was aimed to define a set of parameters that would (a) quantify such abnormalities, (b) be highly reproducible, (c) have sensitivity and specificity greater than the conventional measurements such as QTd in separating normal and clinically relevant abnormal electrocardiograms, and (d) be independent of problematic time-domain measurements such as the detection of the T wave offset.

ECG decomposition by several different methods is known. One example is taught by Acar B. and Koymen H. in an article entitled "SVD-based on-line exercise ECG signal orthogonalization", (1999) IEEE Trans. Biomed. Eng., 46, pp. 311–321. The common approach is to transform the multiple lead ECG into another domain or to identify the dominant components of the recording. The analysis is subsequently carried out in the transformed domain which may have various advantages, e.g. a high signal-to-noise ratio.

In the following description, the uppercase bold letters are used for matrices whereas the lowercase bold letters for vectors.

The analysis is based on the Singular Value Decomposition (SVD) of the standard 12-lead ECG. It defines a minimum dimensional subspace that captures the ECG energy. SVD was defined by Golub G. H., and Van Loan C. F. (1996) in 'Matrix Computations', 3$^{rd}$ edition, (The John Hopkins University Press, Baltimore and London), pp. 70–71, as:

If M is an 8-by-n matrix, with each row corresponding to a standard ECG channel (I, II, V1, V2, V3, V4, V5, V6) and n being the number of samples, then there exist orthogonal matrices $$U=[u_1, \ldots, u_m] \in \mathfrak{R}^{m \times m} \text{ and } V=[v_1, \ldots, v_n] \in \mathfrak{R}^{n \times n}$$

such that $$\Sigma = U^T M V = \text{diag}(\sigma_1, \ldots, \sigma_p) \in \mathfrak{R}^{m \times n} p = \min\{m,n\}$$

where $\sigma_1 \geq \sigma_2 \geq \ldots \geq \sigma_p \geq 0$.

The columns of U are referred to as the left singular vectors, whereas the columns of V are referred to as the right singular vectors. $\sigma_i$ are the singular values. Furthermore, if $\sigma_1 \geq \ldots \geq \sigma_r > \sigma_{r+1} = \ldots = \sigma_p = 0$, then rank(M)=r null(M)=span$\{v_{r+1}, \ldots, v_n\}$ range(M)=span$\{u_1, \ldots, u_r\}$.

where range(M) is the minimum dimensional space which captures the 12-lead ECG energy. As shown in the following section, no significant errors are introduced by restricting the dimension of this space to 3. The singular values are measures of how much ECG energy exists along the corresponding vector u.

The signal representations in the minimum (r-dimensional) decomposition sub-space and the corresponding left singular vectors are used to derive the new parameters (FIG. 1). In the rest of this text, M designates the ECG data matrix. Each column of M corresponds to a sampling instant and each row corresponds to a different ECG channel. Because of the algebraic interdependency, eight of the standard 12 ECG channels are used, namely I, II, V1, V2, V3, V4, V5 and V6. The SVD of M is performed as:

$$\Sigma = \begin{bmatrix} \tilde{\Sigma} & 0 \\ 0 & \tilde{\tilde{\Sigma}} \end{bmatrix} = \begin{bmatrix} \tilde{U}^T \\ \tilde{\tilde{U}}^T \end{bmatrix} MV = U^T MV$$

Figure 2A:
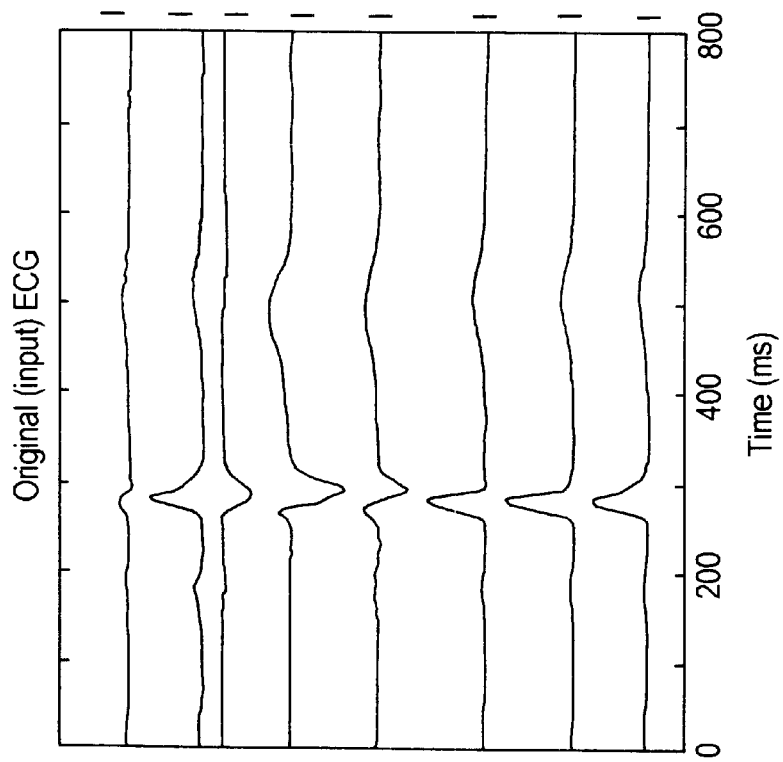
FIGS. 2a and 2b shows 8 input and 8 decomposed ECG signals (which can be obtained by Singular Value Decomposition), respectively.
Figure 2B:
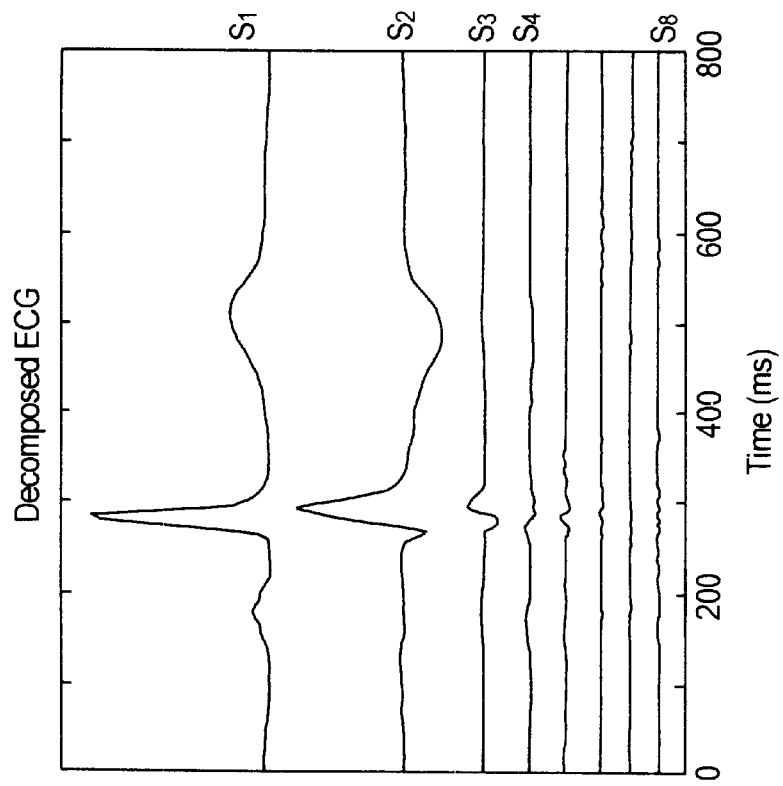

$\tilde{\Sigma} \in \mathfrak{R}^{3 \times 3}$ and is diagonal, $\tilde{U} \in \mathfrak{R}^{8 \times 3}$ where $\tilde{\Sigma} \in \mathfrak{R}^{3 \times 3}$ and is diagonal, and $\tilde{U} \in \mathfrak{R}^{8 \times 3}$. It has been shown previously that 99% of the ECG energy can be represented in a 3-dimensional minimum subspace (see the paper mentioned above by Acar and Koymen, 1999). Hence the effective rank of M is 3. This minimum subspace is spanned by the columns of $\tilde{U} \in \mathfrak{R}^{8 \times 3}$. Let S be the projection of M onto $\tilde{U}$, $S = \tilde{U}^T M$. FIG. 2 shows an example of the input and decomposed (projected) signals. The transformation of the 3 dominant decomposed signals back into the original ECG domain is equivalent to morphological filtering of the ECG in its original domain.

An approximate QRS and T wave detection is performed on the 3 ($s_1$, $s_2$, $S_3$) decomposed signals that contain most of the energy. Let $$s_{3D}(t_i) = [s_1(t_i) \quad s_2(t_i) \quad s_3(t_i)]^T \in \text{span}\{u_1, u_2, u_3\},$$

$$= [s_{2D}(t_i) \quad s_3(t_i)]$$

$$E_{3D}(t_i) = \|s_{3D}(t_i)\|_2.$$

Figure 3:
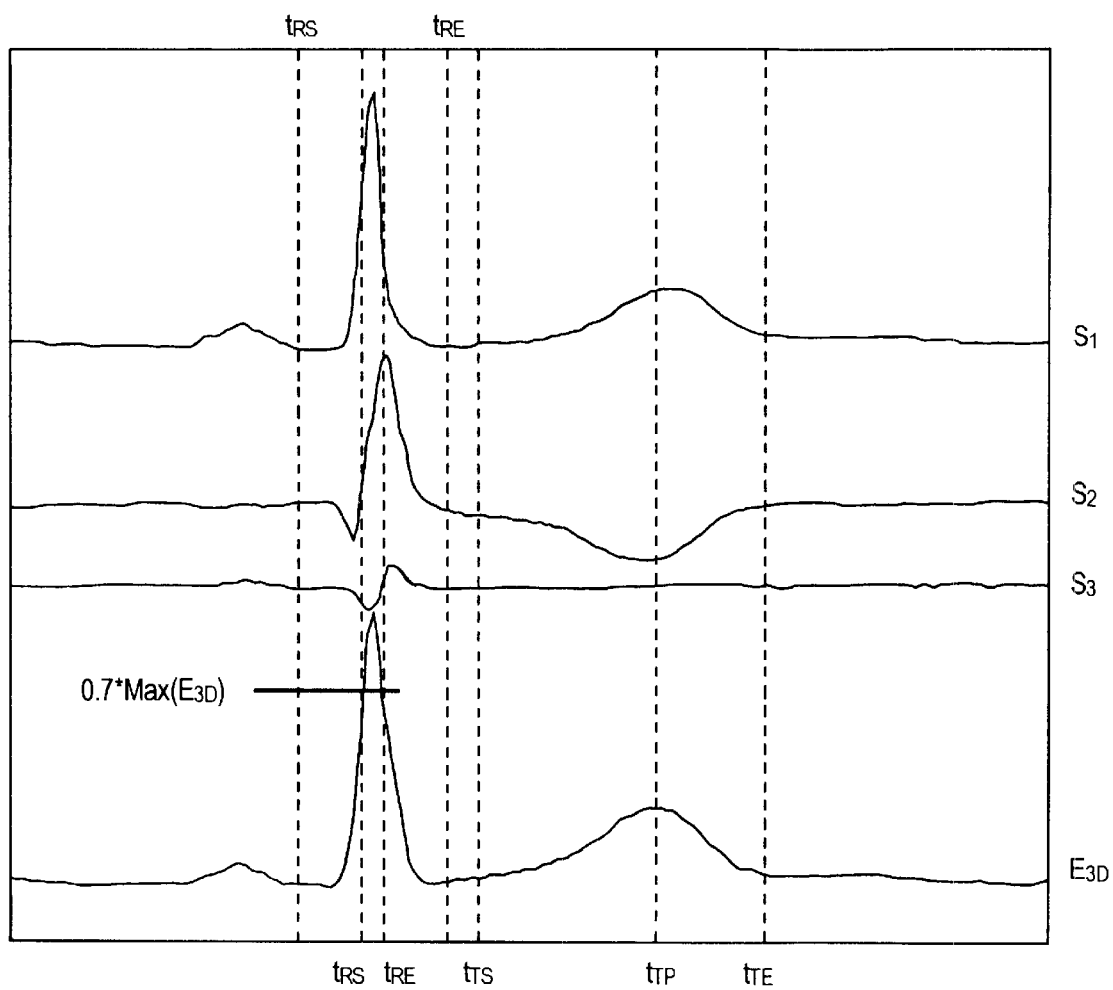
FIG. 3 illustrates approximate QRS and T wave detection using ECG energy, $E_{3D}$, which is calculated from $S_1$, $S_2$ and $S_3$, the most significant 3 decomposed ECG signals.
Figure 4:
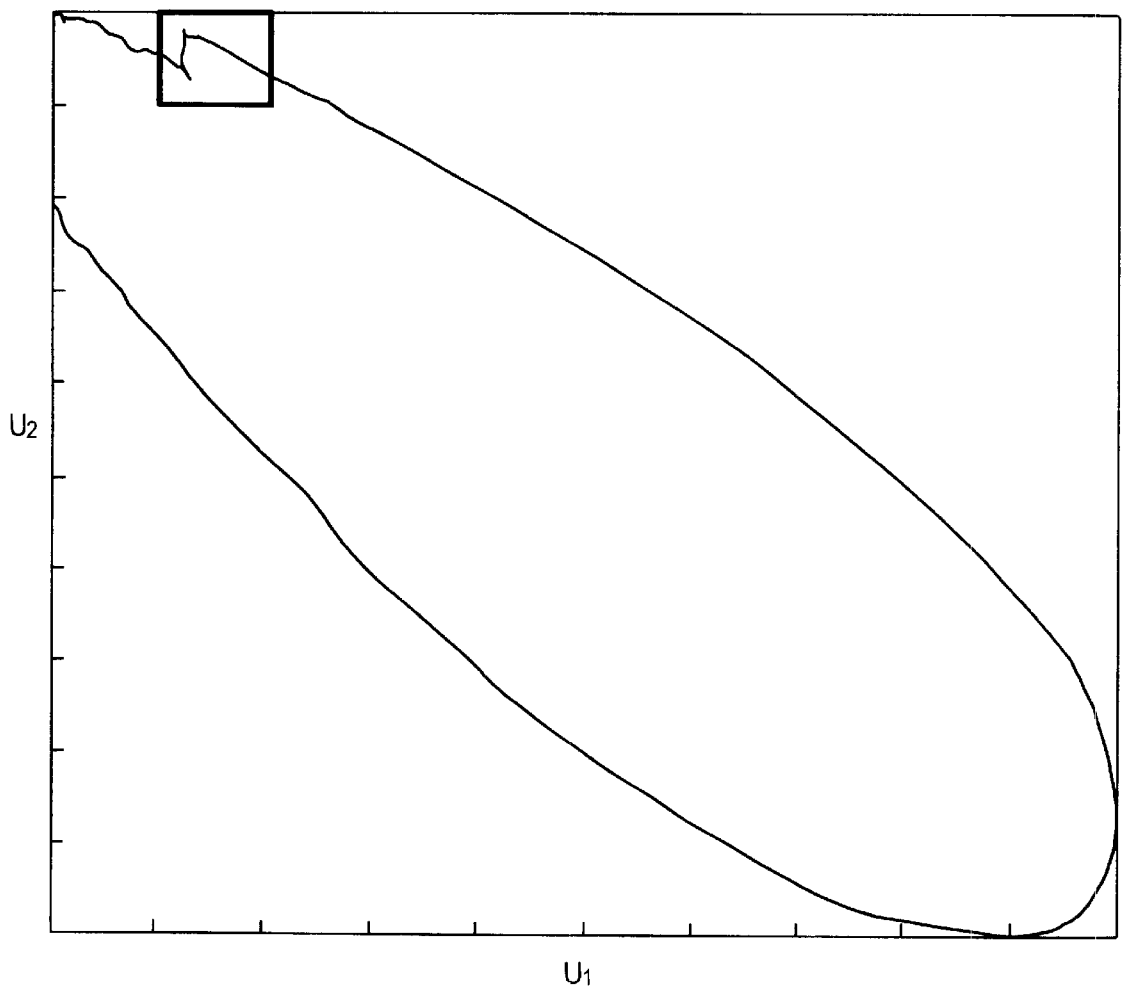
FIG. 4 provides an example of the T loop: Path of the tip of $s_{2D}$ (the most significant point of the ECG vector in the decomposition space) on the $u_1u_2$ plane.
Figure 5:
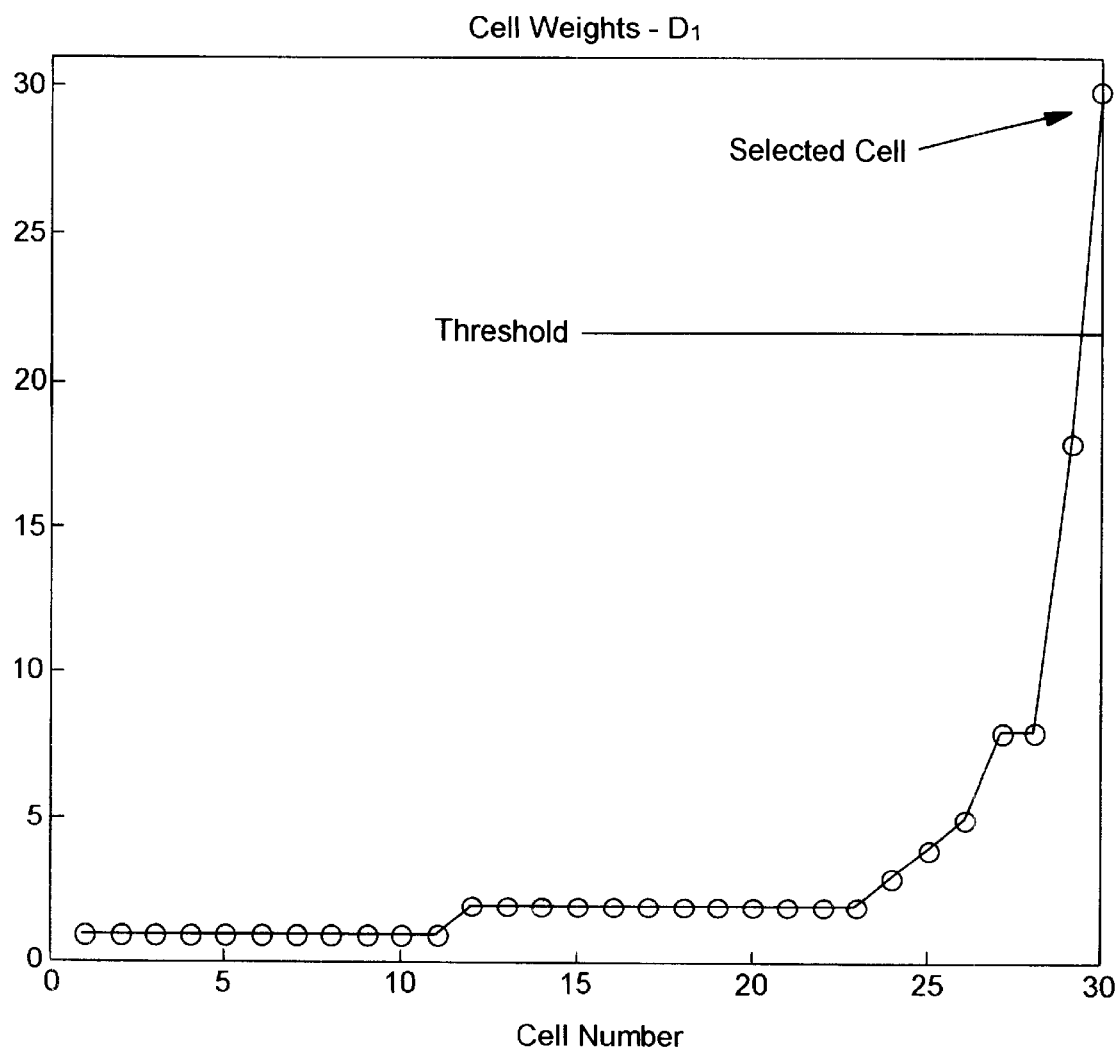
FIG. 5 illustrates an example of the cell weights D's, assigned to 100 equal cells in $u_1u_2$ plane (excluding the zero weights), in increasing order, showing the $30^{th}$ cell above the threshold, the $30^{th}$ cell (the one shown in FIG. 4) is selected as the T wave end.

FIG. 3 shows $S_{3D}$ and $E_{3D}$ for a single beat. The R-wave end point is assumed to be the first point after the maximum of $E_{3D}$, where $E_{3D}$ falls below 70% (arbitrary threshold) of its maximum value. That instant is disclosed as t'$_{RE}$. Although t'$_{RE}$ is not the actual R-wave end point, it serves the purpose. Similarly, the 70% point before the maximum is marked as t'$_{RE}$. The QRS complex is assumed to start 48 msec. before t'$_{RE}$ and end 48 msec. after t'$_{RE}$ (arbitrary limits). These two points are marked as t'$_{RE}$ and t'$_{RE}$, respectively. The T wave peak $t_{TP}$ is assumed to be the maximum point of $E_{3D}$ after t'$_{RE}$. The approximate T wave starting point $t_{TS}$ is taken to be ⅓ of ($t_{TP}$–t'$_{RE}$) after t'$_{RE}$. FIG. 3 shows the positions of t'$_{RE}$, t'$_{RE}$, t'$_{RE}$, t'$_{RE}$, $t_{TS}$ and $t_{TP}$. Since this study is only concerned with single beats, there is no need to choose an end point for the search of the T wave peak. However, such a point can easily be selected based on the instantaneous heart rate, when necessary. The detection of the T wave end point, $t_{TE}$, is based on the path of the tip of $s_{2D}$. FIG. 4 shows the path that the tip of $s_{2D}(t_i)$ follows in the plane spanned by $u_1$ and $u_2$, for $t_i \geq t_{TS}$. The rectangular area is divided into 100 equal rectangular cells (arbitrary number). Each cell is assigned a weight equal to the number of inner data points (time instants). This is a measure of the time spent by the tip of $s_{2D}$ in that cell. Let $D_i$ be the weight of the i$^{th}$ cell. The cells with zero weight are discarded and the other cells are ordered in respect of $D_i$. FIG. 5 shows $D_i$ values for a single beat. Assuming that there are K cells with nonzero weights, $D_1 \leq D_2 \leq \ldots \leq D_K$.

A threshold $th=mean(D_i)+\mu \times standard\_deviation(D_i)$. is used, where $\mu=3$ (arbitrary constant). If $D_i \geq th$ for $L \leq i \leq K$ for $Y \leq i \leq Q$, the earliest time instant at which the tip of $s_{2D}$ enters one of the cells Y to Q ($L \leq i \leq K$), is set to be the approximate T wave end point, $t_{TE}$.

Since the aim of the algorithm is to quantify the T wave shape between $t_{TS}$ and $t_{TE}$, rather than to measure the $t'_{RE}$ interval, the approximate and arbitrary nature of the $t_{TS}$ instant definitions is fully acceptable (as shown further).

If, using the algorithm described above, $t_{TE}$, which should not occur, $\mu$ is increased in steps of 0.2 until $t_{TE} > t_{TP}$. Similarly, if $D_K < th$, $\mu$ is decreased in steps of 0.2 until $D_K \geq th$. Such cases are rare.

This T wave end point detection scheme is based on the concept that the interlead relations do not change in the absence of the ECG signal. Each point on the $u_1 u_2$-plane corresponds to a specific interlead relation defined by the vectors $u_1$ and $u_2$. Hence, each cell in the $u_1 u_2$-plane represents a group of similar interlead relations. When the repolarisation pattern ends, the ECG signal remains confined to a small set of such relations.

The decomposed signal is subsequently normalised with the maximum energy set to 1:

$$s_{3D}(t_i) = [s_1(t_i) \ s_2(t_i) \ s_3(t_i)]^T \in span\{u_1, u_2, u_3\},$$
$$= [s_{2D}(t_i) \ s_3(t_i)]$$
$$E_{3D}(t_i) = \|s_{3D}(t_i)\|_2.$$

QRS complex and the T wave extracted by this algorithm result in decomposed data matrices $S_T$ and $S_{QRS}$, respectively. From both signals, a DC vector is subtracted as follows:

$$s_{3D}^{DC} = 0.25 \times \{s_{3D}(t_{RS}) + s_{3D}(t_{RE}) + s_{3D}(t_{TS}) + s_{3D}(t_{TE})\}$$

From now on, $S_T \in \Re^{3 \times K}$ ($K = t_{TE} - t_{TS}$) and $S_{QRS} \in \Re^{3 \times L}$ ($L = t_{RE} - t_{RS}$) will denote the decomposed, energy normalised and DC-compensated T wave and QRS complex.

The T wave is reconstructed from $S_T$, which is equivalent to a morphological filtering:

$$\hat{M}_T = \tilde{U} S_T = \tilde{U} \tilde{U}^T M_T.$$

Figure 6:
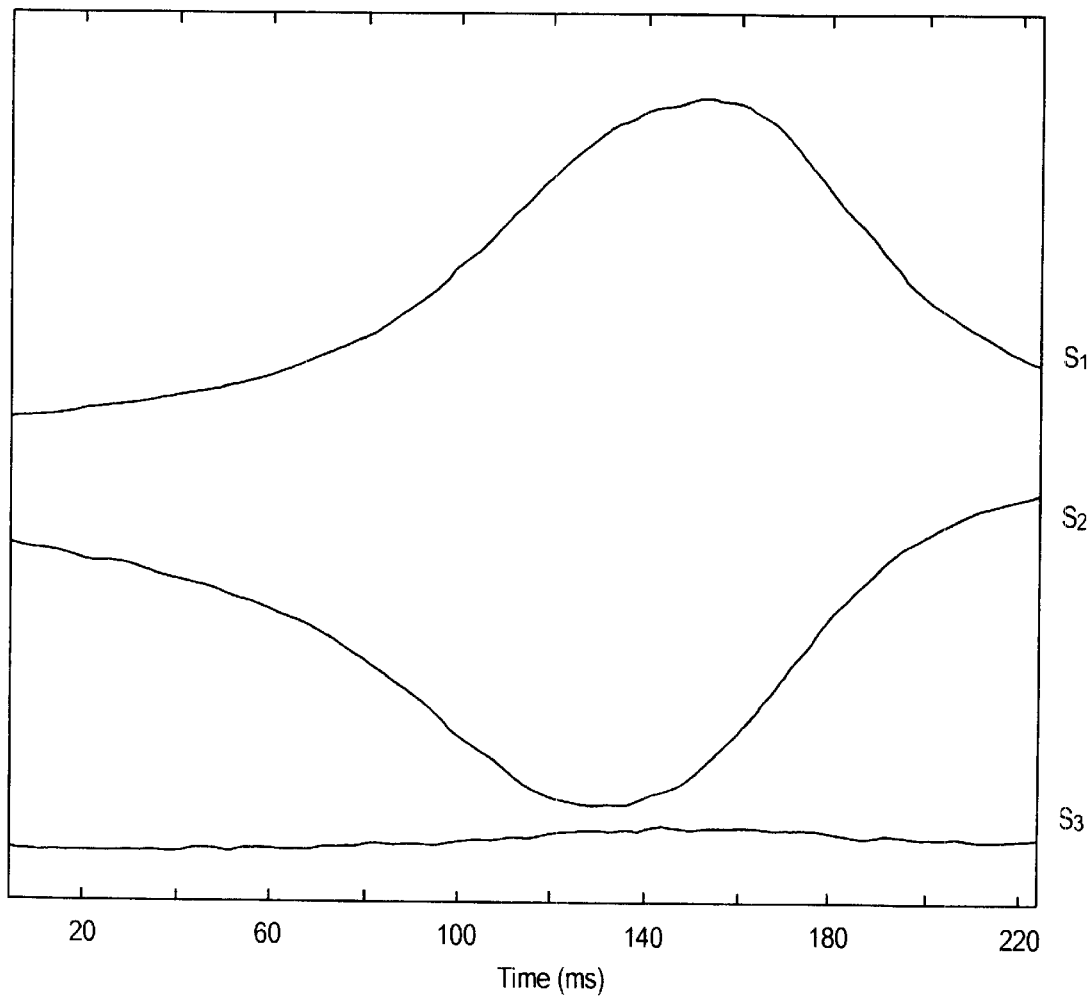
FIG. 6 shows the 3 most significant decomposed, time-orthogonal, channels of a T wave.

The reconstructed T wave, $\hat{M}_T$, is once again decomposed by SVD:

$$\Sigma_T = \begin{bmatrix} \tilde{\Sigma}_T & 0 \\ 0 & \tilde{\tilde{\Sigma}}_T \end{bmatrix} = \begin{bmatrix} \tilde{U}_T^T \\ \tilde{\tilde{U}}_T^T \end{bmatrix} \hat{M}_T V_T = U_T^T \hat{M}_T V_T$$

is diagonal, $\tilde{U}_T \in \Re^{8 \times 2}$ $\Sigma_T \in \Re^{2 \times 2}$ and diagonal, $\tilde{U}_T \in \Re^{8 \times 2}$ The subscript 'T' indicates that we are dealing with the T wave only, and the data superscript '~' by denotes a matrix which is reconstructed (morphologically filtered). Note that $\tilde{U}_T$ has two columns whereas $\tilde{U}$ has three columns. This is because the $3^{rd}$ decomposed signal in T wave decomposition has been excluded (FIG. 6).

The spatial variation descriptors are determined as follows: $\tilde{U}_T$ is an 8-by-2 matrix. Its columns are the two most significant left singular vectors of $\hat{M}_T$, $\tilde{U}_T = [\tilde{u}_{T,1} \tilde{u}_{T,2}]$ $\tilde{u}_{T,k} \in \Re^{8 \times 1}$. Each of its rows is the reconstruction vector of the corresponding standard ECG lead (note that the reconstruction from the 2D, most significant, subspace of the decomposition space means multiplying the decomposed data matrix by $\tilde{U}_T$). Let z denote the reconstruction vectors, $\tilde{U}_T = [z_I z_{II} z_{V1} \ldots z_{V6}]^T z_j \in \Re^{2 \times 1}$ (note that the ECG energy along the two orthogonal dimensions of the decomposed space $\tilde{u}_{T,k}$ and $\tilde{\tilde{u}}_{T,k}$ are proportional to the corresponding singular values $\sigma_{T,1}$ and $\sigma_{T,2}$). To guarantee that we deal with the morphologies rather than the energy differences, the decomposition space is rescaled to equalise the energies in both directions:

$$W_T^T = \tilde{U}_T \tilde{\Sigma}_T = [z_I \ z_{II} \ \cdots \ z_{V6}]^T \tilde{\Sigma}_T$$
$$= [w_I \ w_{II} \ w_{V1} \ w_{V2} \ w_{V3} \ w_{V4} \ w_{V5} \ w_{V6}]^T \ w_i \in \Re^{2 \times 1}$$

Each $w_j$ represents the reconstruction coefficients of the T wave of the $j^{th}$ channel of the standard ECG.

The angle between different $w_j$ vectors is calculated:

$$\theta_{ij} = \angle(w_i, w_j) \ \forall i,j \in \{I, II, V1, V2, V3, V4, V5, V6\}, i \neq j \in [0°, 180°]$$

Figure 7B:
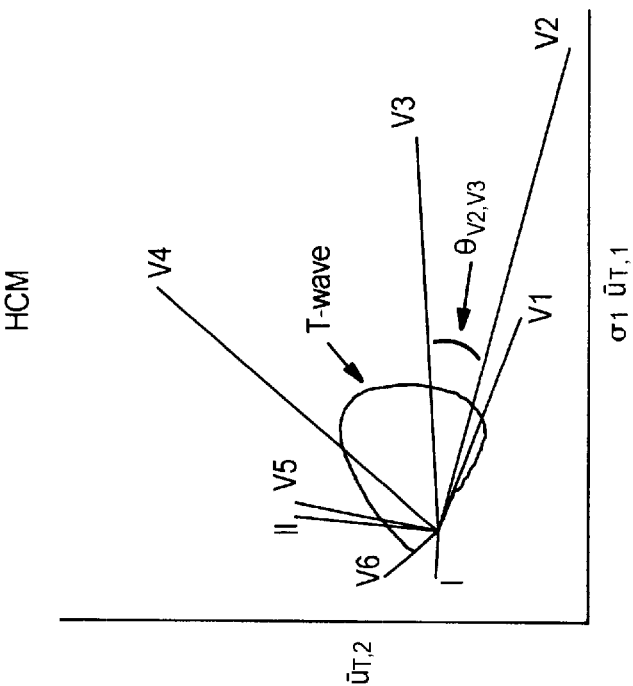
FIGS. 7a and 7b illustrate a T wave loop and reconstruction vectors of each standard ECG lead for a normal and HCM patient respectively.
Figure 7A:
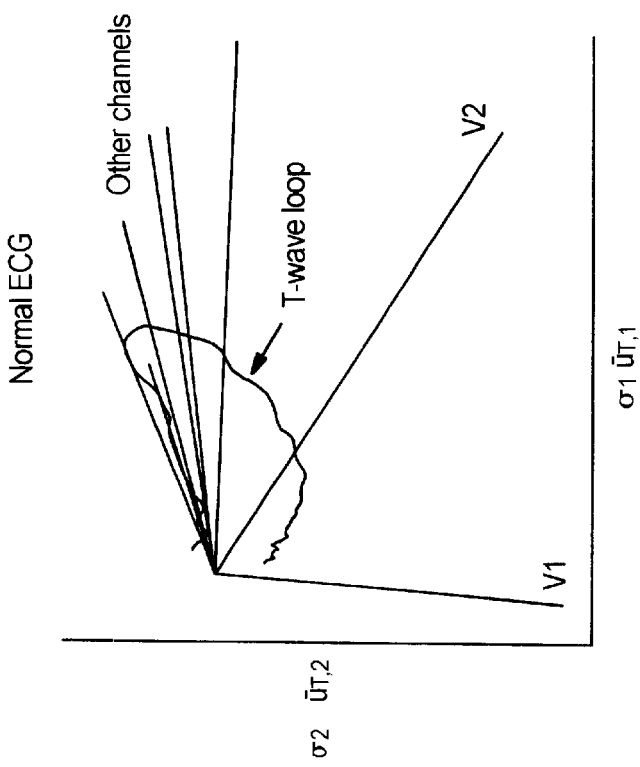

The smaller $\theta_{ij}$, the closer the reconstruction vectors of the $i^{th}$ and the $j^{th}$ ECG channels. It was observed in the data of this study that the T-wave morphology in V1 is generally different than that of other channels, irrespective of any clinical background, mainly due to the position of the V1 electrode. FIGS. 7a and 7b demonstrate the difference between a normal ECG and a HCM case. The projection of the T wave loop onto reconstruction vectors gives the particular T wave as observed in the corresponding ECG lead. It is seen that reconstruction vectors for normal ECG are closely grouped (meaning similar morphology), whereas they are dispersed (meaning different morphologies) for HCM patients. Note that the reconstruction vector of V1 in normal ECG is far from the others. This is the reason why it is preferred to exclude the V1 reconstruction vector from the calculations of the T wave Morphology Dispersion descriptor (i.e., the average of angles between all pairs of reconstruction vectors), to be explained in greater detail below.

The descriptor, T wave Morphology Dispersion (TMD), is defined as the mean of all $\theta_{ij}$ excluding V1:

$$MMV = \frac{1}{21} \sum_{i,j} \theta_{ij} \ \forall i, j \in \{I, II, V2, V3, V4, V5, V6\}, i \neq j$$

TMD is a measure of the spatial T wave morphology variation.

Since the ascending and the descending parts of the T wave are known to correspond to different facets of the repolarisation process, descriptors $TMD_{pre}$ and $TMD_{post}$, which are defined in the same way as TMD with the 'ascending' part of the T wave ($t_{TS} < t < t_{TP}$) used for $TMD_{pre}$ and the 'descending' part ($t_{TP} \leq t < t_{TE}$) used for $TMD_{post}$ were also computed.

Both of the QRS and the T wave represented by $S_{QRS}$ and $S_T$ follow an approximate loop in the column space of $\tilde{U}$. The orientation of the T wave loop is determined by selecting the unit vector $e_{T,1}$, with the maximum T wave energy, subsequently the unit vector $e_{T,2}$ perpendicular to $e_{T,1}$ with the maximum energy, and finally the unit vector $e_{T,3}$ perpendicular to both $e_{T,1}$ and $e_{T,2}$.

The descriptor Total Cosine R_to_T (TCRT) is defined as the average of the cosines of the angles between $e_{T,1}$ and $s_{QRS}(i)$ (columns of $S_{QRS}$) for all i within $[t'_{RS}, t'_{RE}]$. This is a measure of the vector deviation between the depolarisation and the repolarisation waves.

$$TCRT = \frac{1}{t'_{RE} - t'_{RS}} \sum_{i=t'_{RS}}^{t'_{RE}} \cos(\angle(e_{T,1}, s_{QRS}(i))).$$

Figure 8B:
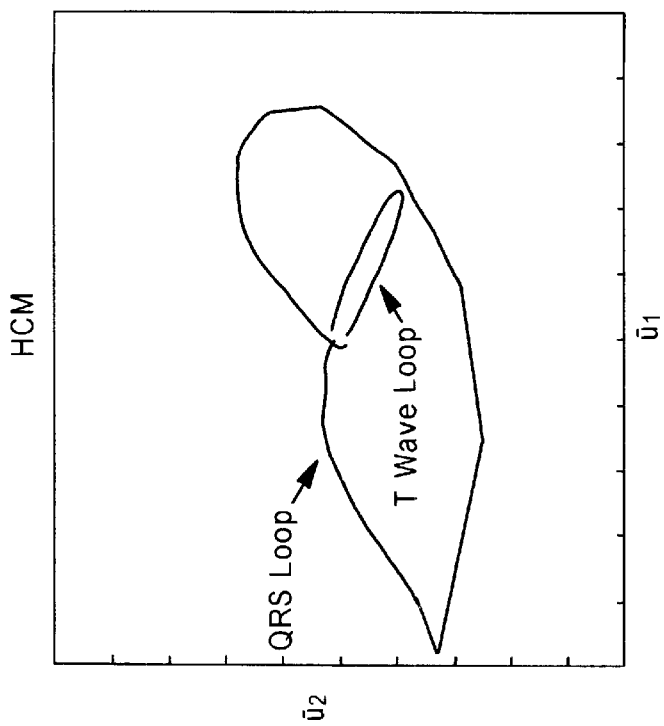
FIGS. 8a and 8b illustrate QRS and T wave loops for a normal and HCM patient respectively.
Figure 8A:
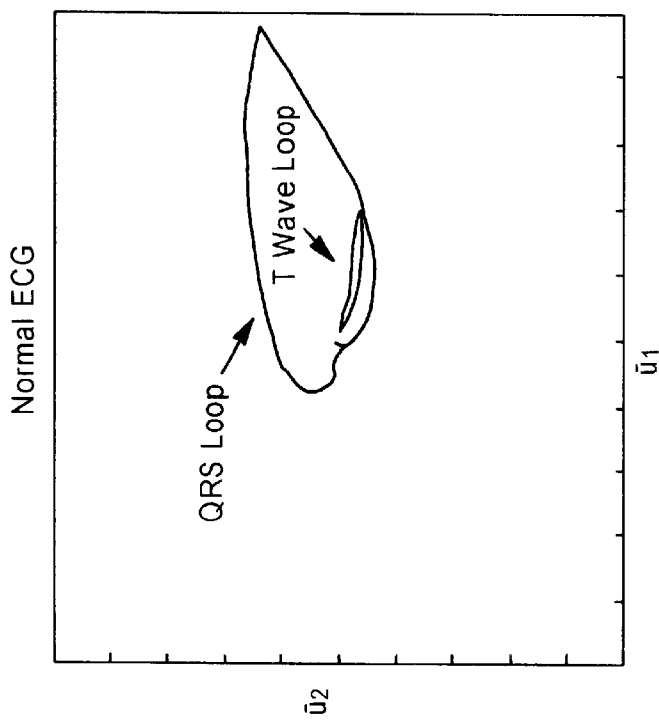

FIGS. 8a and 8b show examples of the QRS and the T wave loop orientations in a normal ECG and a HCM case. TCRT measures the deviation between these two loops. It, in effect, measures the difference between the propagation directions of depolarisation and repolarisation waves. Negative TCRT values correspond to large differences in the loop orientation. In FIGS. 8a and 8b, it can be seen that the orientation of QRS loop and T wave loop are close to each other in the case of a normal patient, whereas they are far from each other in the case of an HCM (hypertrophic cardiomyopathy) patient.

The T wave representation $S_T$, is de-normalised, removing the effect of energy normalisation and its projection onto span($e_{T,1}$, $e_{T,2}$) is calculated orienting the T loop along $e_{T,1}$. The rectangular area encompassing the T loop is divided into n>>1 (in the present implementation n=4900, arbitrary constant) cells of equal size. The loop is closed with a straight line connecting the end points and re-sampled with equal sampling steps of the 2D space. This re-sampling assures that there is at least one sample in every cell that the loop passes through. The numbers of cells in the loop area and in the outer area are counted and the descriptors, Percentage of the Loop Area (PL) and Percentage of the Outer Area (PO) are calculated. PL is the proportion between the number of cells inside the loop and the number of all cells. Similarly, PO is defined for the cells outside the loop. Note that PL+PO<1 because there are cells occupied by the loop itself.

The descriptor termed Lead Dispersion-1 ($LD_1$), is calculated using the decomposed, energy normalised and DC-compensated T wave $S_T$, as it was after the DC-compensation step. $s_{T,2D}(i) \in$ span($u_1$, $u_2$)∀$t_{TE} \leq i \leq t_{TS}$ follows a path in the $u_1 u_2$-plane, the T loop. The rectangular area containing that path is divided into 100 equal cells (arbitrary constant). $LD_1$ is defined as the number of different cells that the path involves. It serves as a measure of the temporal variation of the interlead relations during T wave.

The descriptor, Lead Dispersion-2 ($LD_2$), is defined similarly using the de-normalised T wave. It is the number of different cells that the T loop passes through, excluding the straight line that was added to close the loop. The basic difference between $LD_1$ and $LD_2$ is that $LD_1$ is calculated using the energy normalised decomposed signals (maximum ECG energy=1), while $LD_2$ is calculated using the original decomposed signals.

These descriptors provide further methods of quantifying abnormalities of ventricular depolarisation and repolarisation, and thus relate to further inventions disclosed herein.

The analytical system was implemented on a standard personal computer with Pentium 133 MHz CPU and 80 MB RAM, using Matlab Version 5.2.0 (The MathWorks Inc., 1998). The system was tested with standard 12-lead ECGs recorded by the MAC VU Electrocardiograph (Marquette Medical Systems, Milwaukee, Wis., USA). 10 second recordings with 500 Hz recording rate were acquired and the so-called median beat was obtained for each channel of the recording. These median beats, sampled at 250 HZ, were used in the analysis.

The inputs to system are 8, time-aligned median beats, each one being a representative of the ECG morphology in the corresponding standard channel. The main time consuming computations are the area calculations which involve a recursive algorithm, also implemented in Matlab. On the average, the computation of all parameters for a single recording takes 177 seconds. If excluding the area related parameters (PL and PO), the analysis takes 30 seconds per recording. Matlab commercially available library without any modification is presently used. A purpose built library would increase the performance of the system considerably.

Three sets of ECG recordings were used in the study:

(a) Standard resting 12-lead ECGs recorded in 1100 normal healthy subjects, 913 male, aged 33±12 years, range 10–81 years.

(b) 10 supine resting ECGs were recorded in each of 76 normal healthy subjects, 37 male, aged 38±10 years, range 13–59 years. In each individual, the serial ECGs were recorded one immediately after another using the same electrode attachments and without the subject moving during the whole recording session. Data acquisition of each recording lasted 10 seconds and, including the electrocardiograph handling, each series of the 10 ECGs was obtained within 3 minutes.

(c) Using the same recording strategy, 10 supine resting ECGs were recorded in each of 63 patients with hyperthropic cardiomyopathy (HCM), 44 male, aged 39±14 years, range 12–71 years.

Using a research version of the commercial QT Guard software package (Marquette Medical Systems, Milwaukee, Wis., USA), several conventional descriptors of repolarisation patterns were calculated for each ECG for comparison: This software aligns all beats with respect to the Q wave onset and was programmed to use the downslope inflex tangent method to detect the T wave offset. The following conventional QT interval and T wave parameters were considered:

i. Global QT Dispersion (G-QTd)=Max (QT interval in 12 leads)–Min (QT interval in 12 leads).

ii. Precordial QT Dispersion (P-QTd)=Max (QT interval in 6 precordial leads)–Min (QT interval in 6 precordial leads).

iii. Area QT Dispersion (A-QTd)=All of the 12 leads are assumed to have the same T wave onset and offset points. The areas under the T waves are calculated and the points at which they reach 90% of the corresponding total area are marked for each lead. The dispersion (maximum–minimum) of these markers over 12 leads is calculated.

iv. Global J to Tpeak Dispersion (G-JTpd)=Max (J to Tpeak interval in 12 leads)–Min (J to Tpeak interval in 12 leads).

v. Corrected QT Interval (QTc interval): Bazett formula corrected maximum QT interval in all 12 leads.

Principal Component Analysis of 12 lead T waves is also incorporated in the QT Guard packages. The 8 components with associated eigenvalues are obtained. Each eigenvalue is a measure of the significance of the corresponding component. If $s_i$ denotes the eigenvalue associated with the $i^{th}$ principal component, the following descriptors are calculated:

$$\text{PCA ratio 1 } (PCA_1) = \frac{s_1}{\sqrt{\sum_{i=2}^{12} s_i^2}} \times 100. \qquad \text{vi.}$$

-continued $$PCA\,ratio\,2\ (PCA_2) = \frac{s_2}{s_1} \times 100. \qquad \text{vii.}$$

$$PCA\,ratio\,3\ (PCA_3) = \frac{s_3}{s_1} \times 100. \qquad \text{viii.}$$

Note that these parameters can also be calculated by SVD, assigning $s_i = \sigma_i$.

To find out whether the new methods assess ECG qualities additional to the conventional parameters, the correspondence between the new and the conventional parameters was investigated. All new and conventional parameters of 1100 ECGs acquired from normal subjects were used for this investigation and to calculate the Pearson Product-Moment correlation coefficient (Statistica Package, Release 5.1) between the new and the conventional parameters and the ages of the subjects.

The reproducibility of all the parameters was assessed based on the variation of the measurements between serial ECG recordings from the same individual of the populations of 76 normal and 63 HCM subjects. The ratio of the individual range to the total range was calculated for each patient and each parameter. More precisely, for a fictional parameter X, this ratio $R_{nrm,j}^X$ for normal subject j is equal to $$R_{nrm,j}^X = \frac{\max_{1 \leq k \leq 10}(X_j^k) - \min_{1 \leq k \leq 10}(X_j^k)}{\max_{\substack{1 \leq k \leq 10 \\ 1 \leq i \leq N}}(X_i^k) - \min_{\substack{1 \leq k \leq 10 \\ 1 \leq i \leq N}}(X_i^k)}$$

where N=76 for our data set of 76 normal healthy subjects and $X_n^m$ is the value of descriptor X in $m^{th}$ ECG of the subject n.

The values $R_{hcm,j}^X$ were obtained in a similar way and for each descriptor X, the means and standard deviations of values $R_{nrm,j}^X$ and $R_{hcm,j}^X$ were calculated and used to compare the reproducibility of all the descriptors.

We also investigated the univariate and multivariate distinction between normals and HCM, using all of the new and conventional descriptors. The parameters were compared on the basis of the significance in discriminating these two groups and in terms of specificity and sensitivity. The populations of 76 normal and 63 HCM subjects were used and for each descriptor the mean values of 10 recordings were considered.

Individual parameters were firstly used in a univariate analysis. The normal and HCM groups were compared using non-parametric Mann-Whitney test implemented using an in-house written software according to the original description (see Mann H. B. and Whitney D. R. (1947): "On a test of whether one or two random variables is stochastically larger than the other", Ann. Math. Statistics, 18, pp. 50–60 for more information in this regard). P-value<0.05 was considered as statistically significant.

The Receiver Operator Characteristic (ROC) curves which show the dependency of specificity on sensitivity were calculated for each individual parameter using an in-house software package (see Hnatkova K., Poloniecki J. D. Camm A. J., Malik M. (1994): "Computation of multifactorial receiver operator and predictive accuracy characteristics", Comp. Meth. Prog. Biomed., 42, pp. 147–156, for more information in this regard). The area under the ROC curve (reported as a percentage) was used to characterise the predictive power of each parameter independent of fixed sensitivity levels.

Multiple regression analysis was used to assess the relative performance of individual descriptors in discriminating the HCM from normal subjects. The dichotomy limit of each parameter was set to the mean of the average values of the normal and the HCM groups. Multiple regression models of different orders were calculated (Statistica package, Release 5.1) in a backward stepwise manner, by excluding the least significant variable at each step until the p-values of all surviving parameters were below 0.05.

The most significant parameters, which were identified by the multiple regression analysis, were used for the calculation of multivariate ROC curves. The combinations of two and four parameters were used with the decision rules of at least 1 of 2 positive and at least 2 of 4 positive, respectively.

The results obtained using the new and conventional descriptors were as follows:

Table 1 gives the Pearson Product-Moment correlation coefficients between the conventional and the new descriptors and the age of the patients. None of the new or conventional descriptors had a significant correlation with the age ($|r|<0.16$ for all parameters). The absolute value of all the correlation coefficients between new descriptors were <0.5 except for: $TMD/TMD_{post}$: 0.91, $TMD/TMD_{pre}$: 0.93, $TMD_{post}/TMD_{pre}$: 0.79, PL/PO: −0.94, PL/LD$_2$: −0.54, PO/LD$_2$: 0.50.

The absolute values of the correlation coefficients between the conventional and the new parameters were all <0.5, except: TMD/PCA$_2$: 0.552, LD$_2$/PCA$_2$: −0.562.

Figure 9:
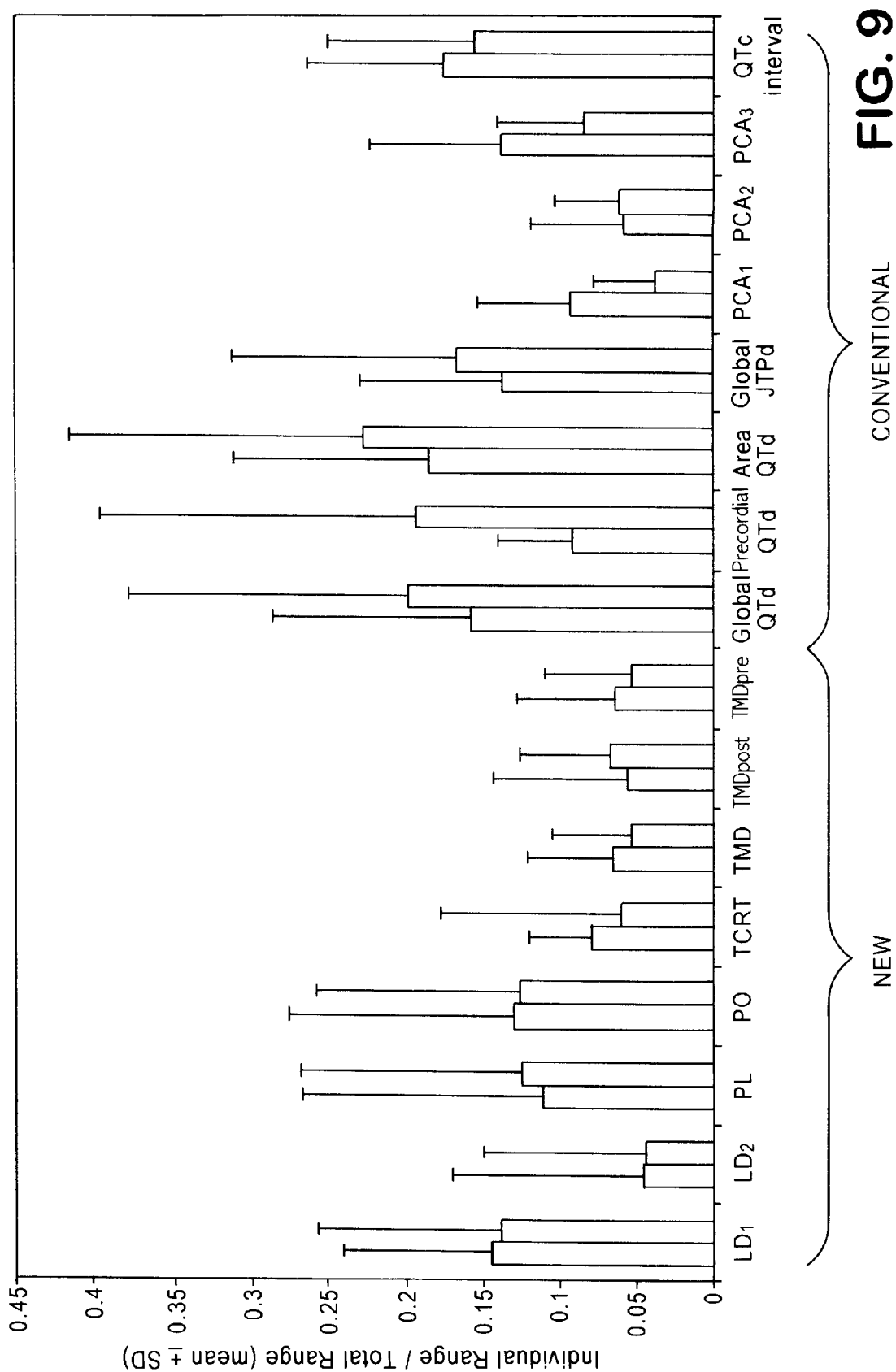
FIG. 9 illustrates the reproducibilities of all the descriptors, as measured by the ratio of individual variation to total variation in 10 supine recordings, from 76 normal and 63 HCM subjects (Grey: Normal subjects; Black: HCMs)

The reproducibility of the conventional descriptors was generally poorer than that of the new ones (FIG. 9) with the exception of PCA$_1$ and PCA$_2$, that had reproducibilities similar to those of the new descriptors.

Table 2 shows the mean values of $\theta_{ij}$ observed in 1100 normal subjects and confirms the reasons for excluding V1 lead from spatial variation descriptors. An increased spatial variation of T wave morphology in HCM subjects was observed in all of the three spatial variation descriptors, i.e. TMD, $TMD_{pre}$ and $TMD_{post}$. The mean TCRT was negative for HCM subjects and positive for normals. The PL was larger for normal subjects whereas the PO was smaller. The mean value of LD$_1$ (as well as of LD$_2$) in normal and HCM groups were close to each other.

Table 3 shows the comparisons between the descriptors in normal and HCM subjects. While all of the descriptors strongly differentiate between both groups, some descriptors have substantially lower p-values than others. The QTc interval and P-QTd offer the most significant univariate differentiation among the conventional descriptors. However, TCRT, TMD and $TMD_{post}$ outperformed all of the conventional descriptors, while $TMD_{pre}$ had a p-value close to that of QTc interval which is the best among the conventional descriptors.

Table 3 also shows the area under the univariate ROC curve for each descriptor. The results confirm the statistical comparisons: TCRT, TMD and $TMD_{post}$ have areas above 90%, QTc interval has the largest area (85.6%) among the conventional descriptors.

Table 4 shows the p-values of each parameter in a succession of multiple regression models of different orders. The descriptors TCRT, $TMD_{pre}$, P-QTd and QTc interval survived throughout the successive multiple regression models performed in a backward stepwise fashion. When excluding $TMD_{pre}$ and $TMD_{post}$, the final significant parameters surviving the backward stepwise multiple regression analysis were TCRT, TMD, P-QTd and QTc interval, with p-values of $5.75 \times 10^{-8}$, 0.011, $5.93 \times 10^{-4}$, $8.61 \times 10^{-6}$, respectively. In both cases, TCRT outperformed all of the other parameters in all orders of multiple regression analysis.

TABLE 1

Pearson Product-Moment correlation coefficients between the new descriptors, the conventional descriptors and the age of the subjects.

CORRELATION COEFFICIENTS

|  | TMD | $TMD_{post}$ | $TMD_{pre}$ | TCRT | PL | PO | $LD_1$ | $LD_2$ |
|---|---|---|---|---|---|---|---|---|
| TMD | 1.00 | | | | | | | |
| $TMD_{post}$ | 0.91 | 1.00 | | | | | | |
| $TMD_{pre}$ | 0.93 | 0.79 | 1.00 | | | | | |
| TCRT | −0.01 | 0.04 | 0.05 | 1.00 | | | | |
| PL | −0.10 | −0.16 | −0.18 | −0.08 | 1.00 | | | |
| PO | 0.09 | 0.14 | 0.17 | 0.08 | −0.94 | 1.00 | | |
| $LD_1$ | 0.08 | 0.05 | 0.07 | 0.00 | 0.14 | −0.17 | 1.00 | |
| $LD_2$ | −0.30 | −0.18 | −0.17 | 0.20 | −0.54 | 0.50 | −0.12 | 1.00 |
| G-QTd | 0.08 | 0.10 | 0.01 | −0.03 | 0.04 | −0.02 | −0.01 | −0.08 |
| P-QTd | 0.16 | 0.16 | 0.09 | 0.00 | 0.03 | −0.02 | 0.00 | −0.15 |
| A-QTd | 0.10 | 0.11 | 0.00 | −0.08 | 0.04 | −0.03 | 0.01 | −0.13 |
| G-JTpd | 0.23 | 0.19 | 0.09 | −0.12 | 0.23 | −0.22 | 0.02 | −0.48 |
| $PCA_1$ | 0.25 | 0.17 | 0.22 | 0.09 | 0.06 | −0.05 | 0.15 | −0.24 |
| $PCA_2$ | 0.55 | 0.46 | 0.46 | −0.14 | 0.04 | −0.06 | 0.05 | −0.56 |
| $PCA_3$ | 0.16 | 0.15 | 0.14 | 0.03 | −0.11 | 0.10 | 0.11 | −0.12 |
| QTc interval | 0.07 | 0.07 | 0.08 | −0.05 | −0.17 | 0.16 | 0.04 | 0.04 |
| AGE | −0.06 | −0.11 | 0.00 | 0.09 | −0.06 | 0.01 | 0.05 | 0.07 |

TABLE 2

Average $\theta_{ij}$ values in the set of 1100 normal subjects. The shaded boxes contain the $\theta_{i,VI}$ and $\theta_{VI,i}$ values that are greater than the others.

AVERAGE $\theta_{ij}$ VALUES

| Channel | I | II | V1 | V2 | V3 | V4 | V5 | V6 |
|---|---|---|---|---|---|---|---|---|
| I | 0.000° | 6.799° ± 7.997° | | 22.47° ± 24.82° | 10.65° ± 10.79° | 4.648° ± 6.553° | 4.451° ± 4.603° | 5.966° ± 6.218 |
| II | | 0.000° | | 27.44° ± 25.79° | 15.43° ± 12.79° | 7.575° ± 9.010° | 4.701° ± 6.317° | 4.180° ± 6.015° |
| V1 | | | 0.000° | | | | | |
| V2 | | | | 0.000° | 12.94° ± 21.72° | 20.73° ± 24.39° | 24.86° ± 24.97° | 27.65° ± 25.42° |
| V3 | | | | | 0.000° | 8.685° ± 8.931° | 12.84° ± 10.70° | 15.64° ± 12.31° |
| V4 | | | | | | 0.000° | 4.406° ± 5.460° | 7.209° ± 8.129° |
| V5 | | | | | | | 0.000° | 2.939° ± 3.893° |
| V6 | | | | | | | | 0.000° |

TABLE 3

The mean values and the standard deviations of all parameters, the Mann-Whitney Test results and the area under univariate ROC curves of the separation between normal and HCM subjects.

SEPARATION BETWEEN NORMAL AND ABNORMAL ECGs

| Parameter | Normal n = 76 Mean ± SD | HCM n = 63 Mean ± SD | Mann-Whitney Test P-Value | Area under ROC Curves |
|---|---|---|---|---|
| TMD | 10.72 ± 4.784 | 41.10 ± 26.85 | $2.818 \times 10^{-18}$ | 90.1% |
| $TMD_{post}$ | 6.141 ± 4.462 | 36.68 ± 27.49 | $2.289 \times 10^{-19}$ | 91.1% |
| $TMD_{pre}$ | 8.682 ± 4.585 | 42.14 ± 32.62 | $1.605 \times 10^{-13}$ | 85.1% |
| TCRT | 0.522 ± 0.274 | −0.351 ± 0.522 | $3.548 \times 10^{-19}$ | 90.9% |
| PL | 0.671 ± 0.085 | 0.608 ± 0.142 | $5.935 \times 10^{-3}$ | 64.3% |

TABLE 3-continued

The mean values and the standard deviations of all parameters, the Mann-Whitney Test results and the area under univariate ROC curves of the separation between normal and HCM subjects.

SEPARATION BETWEEN NORMAL AND ABNORMAL ECGs

| Parameter | Normal n = 76 Mean ± SD | HCM n = 63 Mean ± SD | Mann-Whitney Test P-Value | Area under ROC Curves |
|---|---|---|---|---|
| PO | 0.273 ± 0.072 | 0.328 ± 0.115 | $3.051 \times 10^{-3}$ | 65.2% |
| $LD_1$ | 36.40 ± 1.163 | 34.81 ± 3.157 | $2.522 \times 10^{-6}$ | 71.8% |
| $LD_2$ | 724.5 ± 346.1 | 604.9 ± 458.1 | $6.787 \times 10^{-4}$ | 67.4% |
| G-QTd | 19.97 ± 11.62 | 36.55 ± 18.85 | $6.989 \times 10^{-9}$ | 77.5% |
| P-QTd | 10.79 ± 8.776 | 27.87 ± 18.69 | $6.611 \times 10^{-11}$ | 80.6% |
| A-QTd | 13.70 ± 8.564 | 24.38 ± 12.23 | $2.127 \times 10^{-8}$ | 76.8% |
| G-JTpd | 32.53 ± 12.18 | 45.96 ± 20.61 | $2.463 \times 10^{-5}$ | 70.8% |
| $PCA_1$ | 680.0 ± 226.3 | 481.4 ± 245.8 | $6.698 \times 10^{-8}$ | 76.7% |
| $PCA_2$ | 15.56 ± 6.162 | 23.56 ± 10.85 | $9.886 \times 10^{-7}$ | 74.4% |
| $PCA_3$ | 4.826 ± 2.373 | 7.765 ± 4.235 | $6.603 \times 10^{-9}$ | 78.4% |
| QTc interval | 404.4 ± 15.27 | 435.1 ± 25.50 | $4.122 \times 10^{-14}$ | 85.6% |

TABLE 4

Significance levels of the parameters in different orders of multiple regression models, calculated in a backward stepwise fashion by excluding the least significant parameter at each step.

P-VALUES IN MULTIPLE REGRESSION ANALYSIS

| | P - VALUES in Multiple Regression Models | | | | |
|---|---|---|---|---|---|
| Model Order | All (16) | 10 | 9 | 8 | 4 |
| PARAMETERS | | | | | |
| TMD | 0.769 | — | — | — | — |
| $TMD_{post}$ | 0.272 | 0.140 | 0.174 | — | — |
| $TMD_{pre}$ | 0.037 | 0.008 | 0.004 | 0.008 | 0.001 |
| TCRT | $1.45 \times 10^{-7}$ | $3.43 \times 10^{-8}$ | $5.39 \times 10^{-8}$ | $1.07 \times 10^{-7}$ | $2.24 \times 10^{-8}$ |
| PL | 0.880 | — | — | — | — |
| PO | 0.563 | 0.060 | 0.032 | 0.054 | — |
| $LD_1$ | 0.378 | — | — | — | — |
| $LD_2$ | 0.758 | — | — | — | — |
| G-QTd | 0.335 | 0.065 | 0.110 | 0.156 | — |
| P-QTd | 0.016 | 0.006 | 0.006 | 0.015 | $7.07 \times 10^{-4}$ |
| A-QTd | 0.658 | — | — | — | — |
| G-JTpd | 0.092 | 0.074 | 0.121 | 0.166 | — |
| $PCA_1$ | 0.628 | — | — | — | — |
| $PCA_2$ | 0.397 | 0.122 | 0.062 | 0.082 | — |
| $PCA_3$ | 0.352 | 0.205 | — | — | — |
| QTc interval | $6.06 \times 10^{-5}$ | $5.05 \times 10^{-5}$ | $1.94 \times 10^{-5}$ | $1.93 \times 10^{-5}$ | $8.57 \times 10^{-6}$ |

The multivariate ROC curve involving the descriptors TCRT, $TMD_{pre}$, P-QTd and QTc interval, had an area of 98.4%. Using the conventional and new descriptors separately in bi-variate ROC curves, we obtained areas of 95.5% for TCRT and $TMD_{pre}$, and of 91.6% for P-QTd and QTc interval.

Hence, TCRT, $TMD_{pre}$, P-QTd and QTc interval are mutually independent separators of normal and HCM ECGs of which TCRT is by far the strongest.

The new parameters proposed in this specification are defined using the decomposition space and aimed at the description of the temporal and spatial variations of ventricular repolarisation. The descriptors TMD, $TMD_{pre}$ and $TMD_{post}$ reflect the interlead morphological variations of the T wave patterns, that is the spatial variations. The area related descriptors, that is PL, PO, $LD_1$ and $LD_2$, characterise the temporal variations. TCRT introduces the concept of comparing the global wavefront directions of the depolarisation and repolarisation processes.

The original hypothesis was that, compared to normal ECGs, the spatial and temporal variation of T wave morphology are increased and the depolarisation and the repolarisation vectors are more different in pathological recordings, such as in HCM patients. The statistical comparisons of this study verify this hypothesis.

The mean of PL is higher and PO is lower in normal than in HCM subjects. This suggests that the T loop is relatively smooth and connected (not crossing itself) in normal ECGs than in HCM ECGs. On the other hand, despite the significant difference, the lead dispersion parameters ($LD_1$ and $LD_2$) have similar mean values for both the normal and HCM subjects. This suggests that the loop itself is not discriminative. The loop lengths were similar in both groups. The discrimination by PL and PO seems to be due to the disconnected and narrow loop (inner area is similar to a strip), rather than due to an increased irregularity of its shape.

The change of sign of TCRT between the normal and the HCM subjects provides a clear distinction between the two groups (the negativity of TCRT shows an increased deviation). This is in agreement with the original hypothesis. The repolarisation and depolarisation waves do differ in terms of their principal direction in a 3-dimensional time-orthogonal space. Since the mean difference between normal and abnormal ECGs is 52°, the descriptor does not merely reflect T wave inversion that would result in the difference near to 180°.

TCRT, $TMD_{pre}$, P-QTd and QTc interval were the only parameters that survived throughout the backward stepwise multiple regression analysis comparing normals and HCM subjects and TCRT was the best throughout the test. This verifies that the new spatial variation parameters and TCRT are very potent descriptors of repolarisation abnormalities.

In this preferred embodiment, all of the new descriptors are defined using the decomposition space. This provides an inherent immunity to noise and avoids the inaccuracies associated with time domain measurements, that are common in QT interval related descriptors that depend on T wave offset determination. The independence of time domain measurements makes the new descriptors highly reproducible, which is very important for their potential clinical applicability. Among the conventional parameters, only $PCA_1$ and $PCA_2$ have a reproducibility in the same order which is again due to avoiding the time domain measurements.

The weak correlation between the new and the conventional parameters shows that the new concepts quantify different properties of the ventricular repolarisation. Furthermore, the two new concepts, that is the spatial and temporal variation can be identified by strong correlations within each group and by weak correlations across the groups. The concept of TCRT is different from both spatial and temporal variations and the descriptor does not correlate strongly with any other descriptor.

The relatively poorer reproducibility of the T loop area related parameters is due to the algorithmic problems. An open loop may result from baseline wander, as well as ST-segment elevation/depression. A straight line was used to connect the ends of the loop, which is not necessarily the best approach. An alternative may be to connect the ends of the loop and its centre of gravity or to transform the $u_1u_2$-plane creating a closed loop. It is also possible that the loop crosses itself, resulting in more than one surrounded area. In the study, the inner area was defined as the closed area neighbouring the beginning of the loop, ignoring the "pockets". It is an open question whether the existence and/or the area of these 'pockets' is of any significance. The poor performance of the loop related descriptors in differentiating normal and abnormal ECGs may well be due to these problems.

The arbitrary choice of constants, used in dividing the plane of ECG into equal size cells, have an influence on $LD_1$, $LD_2$, PL and PO calculations as well as in approximate T wave offset detection. They define the precision of these descriptors. Increasing these constants would increase the precision at the cost of increased computation time. However, the precision is also restricted by the ECG sampling rate which determines the smallest distance between two consecutive ECG vectors. Unreasonably decreased cell size (increased constants) would also degrade the performance of T wave offset detection.

On the other hand, the T wave onset/offset definitions may have an influence on the temporal variation descriptors but do not affect the others. Setting the constant $\mu$ in T wave offset detection to 3 is an appropriate choice. The algorithm readjusted that value in 91 of 1100 normal ECGs. The QRS onset/offset definitions, on the other hand, are robust and able to handle wide QRS complexes. However, the choice of 70% threshold in determining the region of QRS used in TCRT calculation is important. A too low threshold may result in a too general estimation of the QRS loop orientation, whereas a high threshold may misinterpret the orientation of the depolarisation wavefront vector.

Only the principal direction of the ECG vector during T wave, $e_{T,1}$ was used in TCRT calculation, that is the other lower energy components, $e_{T,2}$ and $e_{T,3}$ were ignored. The average ratio of the energy along the second component to that of the first was 0.14 for normals and 0.22 for HCM patients. This shows that the T loop generally resembles a narrow ellipsoid and it is the direction of this loop that is of interest. Using $e_{T,2}$ and/or $e_{T,3}$ would not improve the concept of TCRT, mainly due to a decreased noise immunity. There is no ambiguity in the $e_{T,1}$ definition because the DC-compensation ensures that $e_{T,1}$ has the correct sign.

In conclusion, therefore, it can be seen that the new descriptors of repolarisation patterns described in this specification have several important qualities:

All of the new descriptors can be assessed in a minimum dimensional space constructed by SVD of 12-lead ECG. This provides a built-in immunity to noise.

None of the new descriptors require accurate time domain interval measurements. This makes them more reproducible than the conventional QT interval related descriptors.

The new descriptors assess different ECG qualities than the conventional parameters.

The spatial variation and wavefront direction descriptors can discriminate between normal and abnormal ECGs substantially better than the conventional descriptors. The wavefront direction descriptor (TCRT) is by far the strongest of all considered in this study.

In a second case study, the effect of changes in the autonomic tone of a patient was studied using known descriptors and some of the new descriptors described in the first case study. The findings were as follows:

In the early thirties, Wilson et al. (Wilson F. N., Macleod A. G., Barker P. S., Johnston F. D., The determination and the significance of the areas of the ventricular deflections of the electrocardiogram. A. Heart J. 1934; 10:46–61; Wilson F. N., Macleod A. G., Baker P. S., The T Deflection of the Electrocardogram. TR A Am Physicians 1931; 46:29) introduced the concept of algebraic sum of the areas under the ventricular deflections of the electrocardiogram (the net QRST area). The resulting vector quantity, called 'the ventricular gradient' (VG) was proposed as independent of the sequence of ventricular activation as long as the ventricular recovery properties remained constant. Therefore it was believed that the VG could help distinguish T wave changes following changes in the activation pattern ('secondary' T wave changes) from those due to myocardial damage ('primary' T wave changes).

The original idea did not evolve into a clinically useful tool both because of technical difficulties with the measurement, and because of data challenging the quantitative independence of the activation sequence. As discussed in relation to the first case study, a new descriptor of the wavefront direction of repolarisation has been proposed. It quantifies the difference in the global direction of the wavefronts of the depolarisation and of the repolarisation as an average of the cosines of angles between main depolarisation and repolarisation vectors in a minimum dimensional subspace derived from the independent leads of the electrocardiogram (total cosine R to T, TCRT). Although measured in the optimised 3D space that contains the maximum energy of all ECG leads, this new descriptor advances the classical concept of VG.

Ventricular gradient is a vector which gives the direction and magnitude of the electrical forces produced by a lack of uniformity in the duration of the excited state; it points from the region in which the average length of systole is greatest, toward the region in which it is least. Once considered a 'fundamental quantity in electrocardiography' the VG was gradually forgotten due to both uncertainties about the validity of its concept as well as to technical difficulties with its manual calculation from QRS-T time integrals before the personal computer era. Today the VG is hardly mentioned in modem textbooks of electrocardiology with comments such as that 'the most exciting thing about the ventricular gradient is its name'. The TCRT has been demonstrated to be more reproducible and to separate normal from abnormal ECGs better than several repolarisation parameters including the dispersion of the QT-end and JT-peak intervals and the corrected QTc interval. TCRT has also been found to contain independent predictor value of mortality and arrhythmic complications after myocardial infarction.

These observations suggest that the concept of VG might have been neglected prematurely. Having this in mind, several studies were initiated researching the properties of VG and of its modern and more precise counterpart. In the present study, the effects of basic autonomic provocations on VG were investigated. The study assessed the effect of postural changes and autonomic provocative manoeuvres on the direction and magnitude of the spatial VG and on TCRT in healthy subjects. We compared the effects of postural and autonomic provocations on VG descriptors with the effect on conventional repolarisation parameters, namely the QT interval duration and QT dispersion.

The study population consisted of 40 healthy subjects, 31 male, median age 33 years, mean age 33.1±7.3 years, range 18–56 years, with no history of heart disease and with normal resting 12-lead ECG. None of the subjects was taking any autonomically active medication and before the test, the subjects were instructed to refrain from smoking and from caffeine intake.

The procedure was as follows:

Following 10 minutes supine rest in a comforting temperatured and dimmed room with a low level of background noise, the subjects performed the following tests:

Postural changes (32 subjects): resting supine position, followed by sitting, unsupported standing, supine, and standing position, 4 minutes in each position (total of 20 minutes), with abrupt transition between the separate positions.

Valsalva manoeuvre (30 subjects): forced expiration into the mouthpiece of mercury manometer maintaining a constant pressure of 40 to 50 mm Hg for up to 1 minute. Each manoeuvre was performed 3 times in supine position with 4 min periods between the tests, and 3 times in unsupported standing position also with 4 minutes periods between the manoeuvres.

Sustained Handgrip (8 subjects); the maximum force of contraction was determined in each individual following which each subject maintained 30% of maximum force for 5 min. Each test was performed twice in supine position with 4 minute periods between the tests and twice in unsupported standing position again with 4 minutes of rest between the tests.

The data were recorded using continuous 12-lead digital ECG (250 Hz sampling rate, 12 bit A/D conversion) for the complete procedural section for each subject without any loss of signal using a digital recorder (SEER MC, Marquette Medical Systems, Milwaukee, Wis., USA). ECG data were stored in separate 10 sec portions. The individual tests were organised in a synchrony with the recorder in order to identify each 10 sec ECG sample within a specific phase of each test.

From each lead of each 10 sec ECG sample, the so-called 'median beat' was constructed representing the ideal QRST complex of the given ECG. Data analysis of ECG patterns was based on these median complexes.

The magnitude and angle of spatial VG were calculated in the following ways. From the median ECG beat, the area of the QRS complex and of the T wave in each of the 12 leads were calculated using the ECG Research Workstation Software Package Version 1.0, by Marquette G. E. (Milwaukee, Wis., USA). The QRS and T wave areas in the orthogonal X, Y, Z leads were derived from the areas in the 8 independent leads (II, II, $V_1$, $V_2$, $V_3$, $V_4$, $V_5$ and $V_6$) using the inverse Dower matrix. The magnitude of the spatial VG was calculated as $$VG_m((QRS_x+T_x)^2+(QRS_y+T_y)^2+(QRS_z+T_z)^2)^{1/2}$$

where $QRS_w$ and $T_w$ are the areas of the QRS complex and of the T wave in the orthogonal lead W, respectively. The angle VGa of the spatial VG was calculated as the spatial angle between vectors originating in the centre of the co-ordinates with the final points of $[QRS_x, QRS_y, QRS_z]$ and $[T_x, T_y, T_z]$, respectively.

As described in detail in the description of the first case study, the total cosine R_to_T (TCRT) was calculated. The median beat was represented in a minimum dimensional subspace using singular value decomposition of the standard 12-lead ECG. The TCRT was defined as the average of the cosines of the angles between the main QRS and T vectors in the 3-dimensional reconstructed subspace. In effect, TCRT measures the difference between the propagation directions of the depolarisation and repolarisation waves, with smaller (and negative) values corresponding to greater difference between the two wavefront directions.

The median beats of all ECGs were analysed automatically using the QT Guard software package (Marquette G. E.). A common onset of the Q-wave in all leads was identified and the offset of the T wave in each lead was determined by the downslope inflex tangent method. For the purpose of this study the maximum QT interval, the global QT dispersion (QTd, maximum QT interval in 12 leads–minimum QT interval in 12 leads) and the RR interval were taken from the results provided by the QT Guard package.

The first 2 minutes of the supine rest recordings were ignored in order to achieve fully stabilised steady state. The recordings obtained during the final 8 minutes of the 10 minutes of supine rest were used to derive baseline values for each parameter and to investigate their mutual correlation as well as correlation with heart rate. To investigate the correlation, averaged supine resting values of individual subjects were considered.

The mean values of each parameter for the separate positions and autonomic manoeuvres were calculated and compared by paired t-test and one-way within subjects (repeated measures) analysis of variance (ANOVA) with post hoc comparisons using Scheffe test (Statistica, Version 4.00). All values are expressed as mean±standard error of the mean (SEM). Statistical significance was defined as $p<0.05$.

The results of the study were as follows: The correlation coefficients between VGa, VG, TCRT and RR interval during steady-state supine position are shown in Table 5. There was a significant correlation between the angle and the magnitude of the VG, and between the angle of the VG and TCRT. While both VGa and VGm were significantly correlated to the RR interval, there was no significant correlation between TCRT and RR (Table 5).

Postural changes significantly decreased both VG and TCRT. While VGm and TCRT were significantly decreased in sitting and further in standing position position, VGa was increased in sitting and was further increased in standing position (Table 6).

As expected, the RR interval was significantly shortened in sitting and further in standing position. The maximum QT interval followed the changes of the RR interval (see FIGS. 10a and 10b).

VGa, VGm and TCRT were abruptly changed with transition from supine to sitting and from sitting to standing position. There was a general tendency for TCRT to be changed more abruptly when assuming each new position, compared to both VGa and VGm.

VGm and TCRT were significantly decreased and VGa was significantly increased during the strain phase of Valsalva manoeuvre compared to preceding resting period both in supine and in standing position.

The RR interval were significantly decreased during the strain phase of Valsalva both supine and standing. QT max was slightly but statistically significantly shortened during Valsalva in standing (364±4 vs 371±5 ms, p=0.02) but not in supine position (Table 6).

QT dispersion was not changed significantly during Valsalva.

VGm and TCRT were slightly but significantly increased by handgrip in supine position compared to the preceding resting period (57.8±4.1 vs 56.1±3.9 mVms, p<0.0001 for VGm and 0.63±0.06 vs 0.61±0.06, p=0.0007 for TCRT). Both descriptors were not changed significantly by handgrip in standing position. VGa was slightly but statistically significantly reduced by handgrip in supine (40.0±3.1 vs 40.8±3.1, p=0.01) and increased in standing position compared to preceding resting period (52.8±3.8 vs 51.8±3.7, p=0.027).

Neither the RR interval, nor QTd were changed significantly by handgrip compared to preceding resting period in supine as well as in standing position. However, QTmax was slightly, but significantly shortened by handgrip in standing position 370±5 vs 374±5, p=0.06).

The aim of this study was to examine the effect of established autonomic tests on the spatial ventricular gradient and on a new descriptor of the wave direction of depolarisation and repolarisation, TCRT.

The main finding is that both the magnitude and the angle of the spatial ventricular gradient, as well as the new wave direction descriptor, TCRT, react sensitively and rapidly to changes induced by postural and Valsalva manoeuvres. As expected from their mathematical relation (i.e. the algebraic sum of two vectors decreases as the angle between them increases) VGm followed the opposite trend to VGa and was significantly reduced in sitting compared to supine and was further reduced in standing position.

Figure 10A:
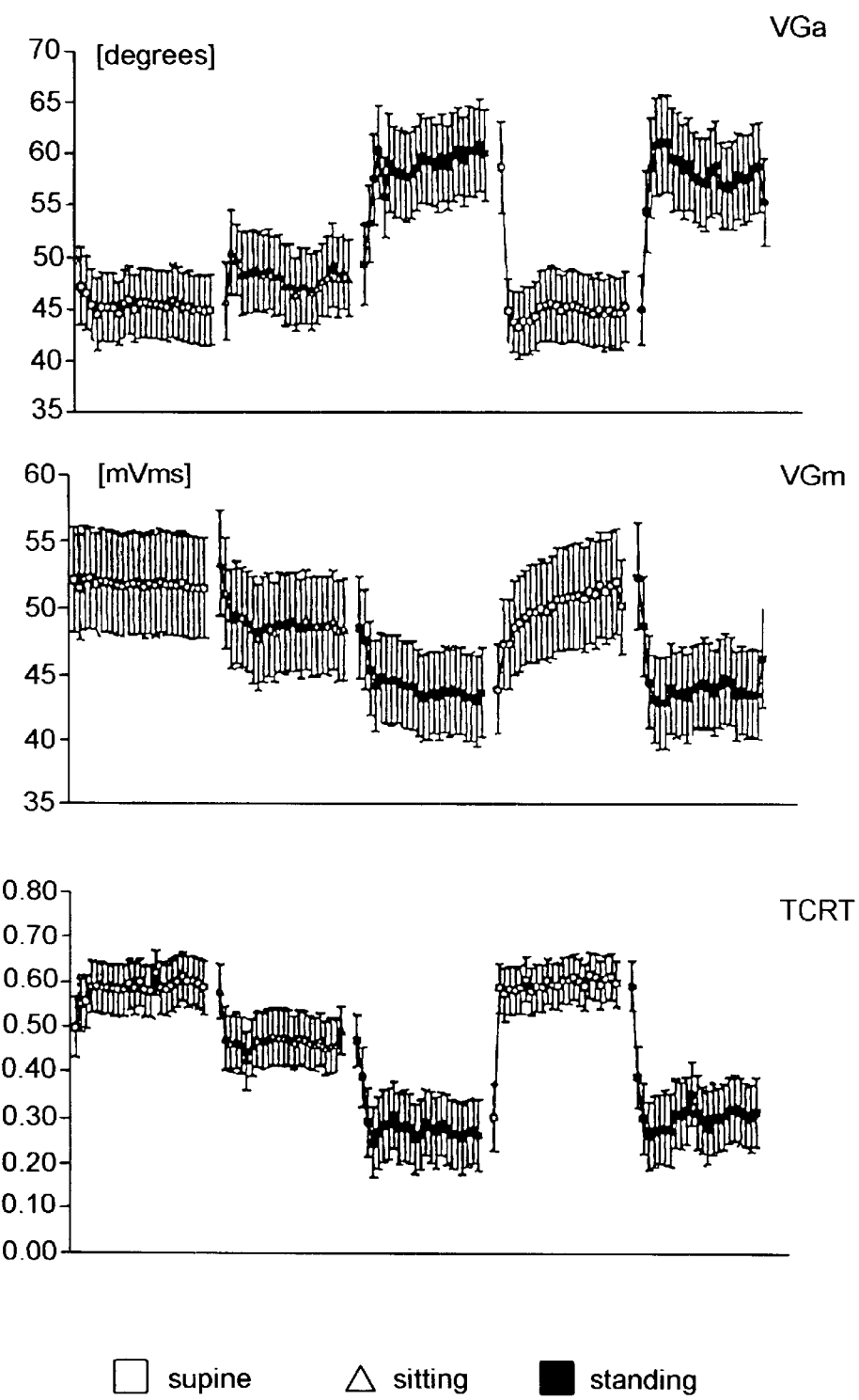
FIGS. 10a and 10b show the variations in descriptor value for ventricular gradient angle, ventricular gradient magnitude, TCRT, RR interval, maximum QT and QT dispersion for the postural changes of resting supine position, followed by sitting, unsupported standing, supine and standing position.
Figure 10B:
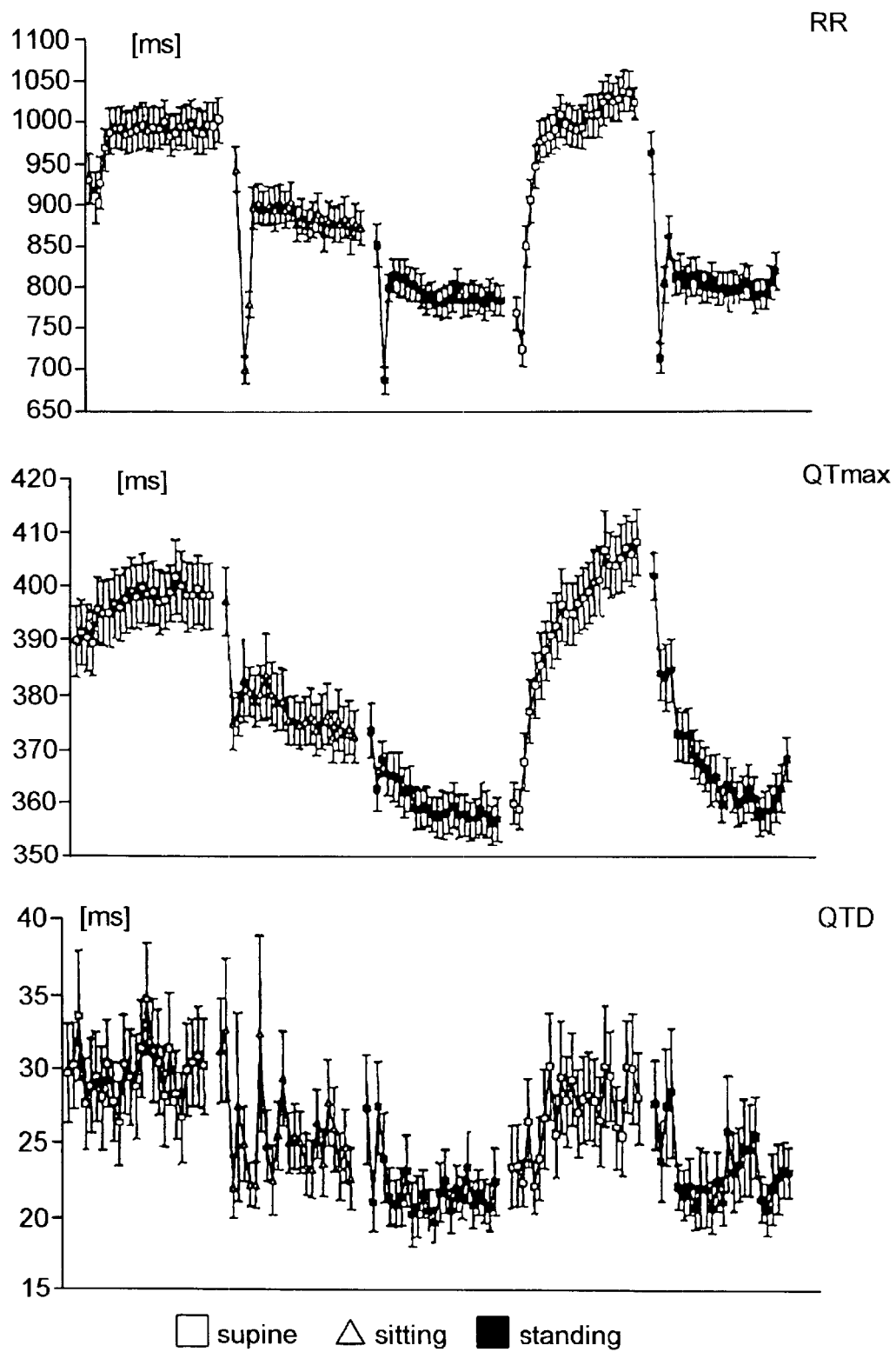

Even more impressive than the absolute magnitude was the speed of the change of VG and TCRT during postural changes and Valsalva manoeuvre. Statistically significant changes in TCRT were detectable already in the first or second 10-sec median ECG beat after standing up from supine or sitting position, or lying down from standing position (FIGS. 10a and 10b). Considering the fact that during the first 10-sec recording in each new position, the actual postural change took place (taking approximately 3–4 seconds), it is apparent that TCRT is an extremely rapidly responding parameter. TCRT appears to be able to respond more rapidly to autonomic modulations than both VGa and VGm.

TABLE 5

Correlation Coefficients Between The Wavefront Direction Descriptors, and Between Each of Them and the RR Interval

| Descriptor | VGa | VGm | TCRT |
|---|---|---|---|
| VGm | −0.50** | 1 | |
| TCRT | −0.78** | 0.15 | 1 |
| RR | −0.39* | 0.58** | 0.09 |

*p < 0.05;
**p < 0.01

TABLE 6

Repolarisation Descriptors During Postural Changes, Strain Phase of Valsalva Manoeuvre and Handgrip (mean ± SEM)

| | | Supine* | Sitting** | Standing*** | Valsalva′ supine | Valsalva″ standing | Handgrip′ supine | Handgrip″ standing |
|---|---|---|---|---|---|---|---|---|
| RR [ms] | | 973 ± 23 | 875 = 19 | 803 ± 20 | 891 ± 24 | 749 ± 22 | 992 ± 26 | 830 ± 21 |
| | p value | <0.0001 | <0.0001 | <0.0001 | 0.0002 | 0.0001 | 0.07 | 0.91 |
| VGa [°] | | 45.2 ± 3.4 | 48.0 = 3.7 | 57.8 ± 4.2 | 42.9 ± 3.2 | 58.0 ± 4.0 | 40.0 ± 3.1 | 52.8 ± 3.8 |
| | p value | 0.02 | <0.0001 | <0.0001 | 0.048 | 0.03 | 0.01 | 0.03 |
| VGm [mV · ms] | | 50.9 ± 3.8 | 48.9 ± 3.8 | 44.4 ± 3.4 | 51.6 ± 3.7 | 42.2 ± 3.2 | 57.8 ± 4.1 | 49.4 ± 3.8 |
| | p value | 0.002 | <0.0001 | <0.0001 | 0.0006 | <0.0001 | <0.0001 | 0.036 |
| TCRT | | 0.59 ± 0.05 | 0.48 = 0.06 | 0.31 ± 0.08 | 0.48 ± 0.07 | 0.25 ± 0.08 | 0.63 ± 0.06 | 0.38 ± 0.08 |
| | p value | 0.0007 | <0.0001 | <0.0001 | 0.0003 | 0.0003 | 0.0007 | 0.22 |
| QT max [ms] | | 394 ± 6 | 378 ± 5 | 364 ± 4 | 393 ± 5 | 364 ± 4 | 402 ± 6 | 370 ± 5 |
| | p value | <0.0001 | <0.0001 | <0.0001 | 0.31 | 0.02 | 0.47 | 0.006 |
| QTd [ms] | | 28.4 ± 2.4 | 25.6 ± 1.9 | 22.6 ± 1.5 | 29.4 ± 1.7 | 24.5 ± 1.4 | 27.1 ± 2.3 | 21.5 ± 1.3 |
| | p value | 0.08 | 0.03 | 0.01 | 0.76 | 0.83 | 0.94 | 0.23 |

*p values vs sitting;
**p values vs standing;
***p values vs supine
′compared with preceding rest, values for which are not given in the table
″compared with preceding rest, values for which are not given in the table Previous studies have described significant reduction of $VG_m$ in standing position compared to supine, as well as during the strain phase of Valsalva manoeuvre. The effect of all phases of Valsalva manoeuvre on repolarisation descriptors, however, can be assessed precisely only on beat-to-beat basis analysis.

It is difficult to comment on the differences in the effect of Valsalva manoeuvre and sustained handgrip on the wavefront direction descriptors. Although handgrip in supine position statistically significantly increased VGm (56.1±3.9 vs 57.8±4.1 mVms, p<0.0001) and TCRT (0.61±0.06 vs 0.63±0.06, p=0.0007) and decreased VGa (40.8±3.1 vs 40.0±3.1, p=0.01) the differences were much smaller than those induced by Valsalva manoeuvre and postural changes. The handgrip test, however, is known to be of limited sensitivity and specificity.

We found statistically significant correlation (r=−0.78, p<0.0001) between VGa and TCRT during steady-state supine conditions. The spatial VGa and TCRT appear to quantify the same physiological phenomenon, namely the difference in the spatial direction of the wavefronts of the depolarisation and the repolarisation, in a three-dimensional space.

Figure 11A:
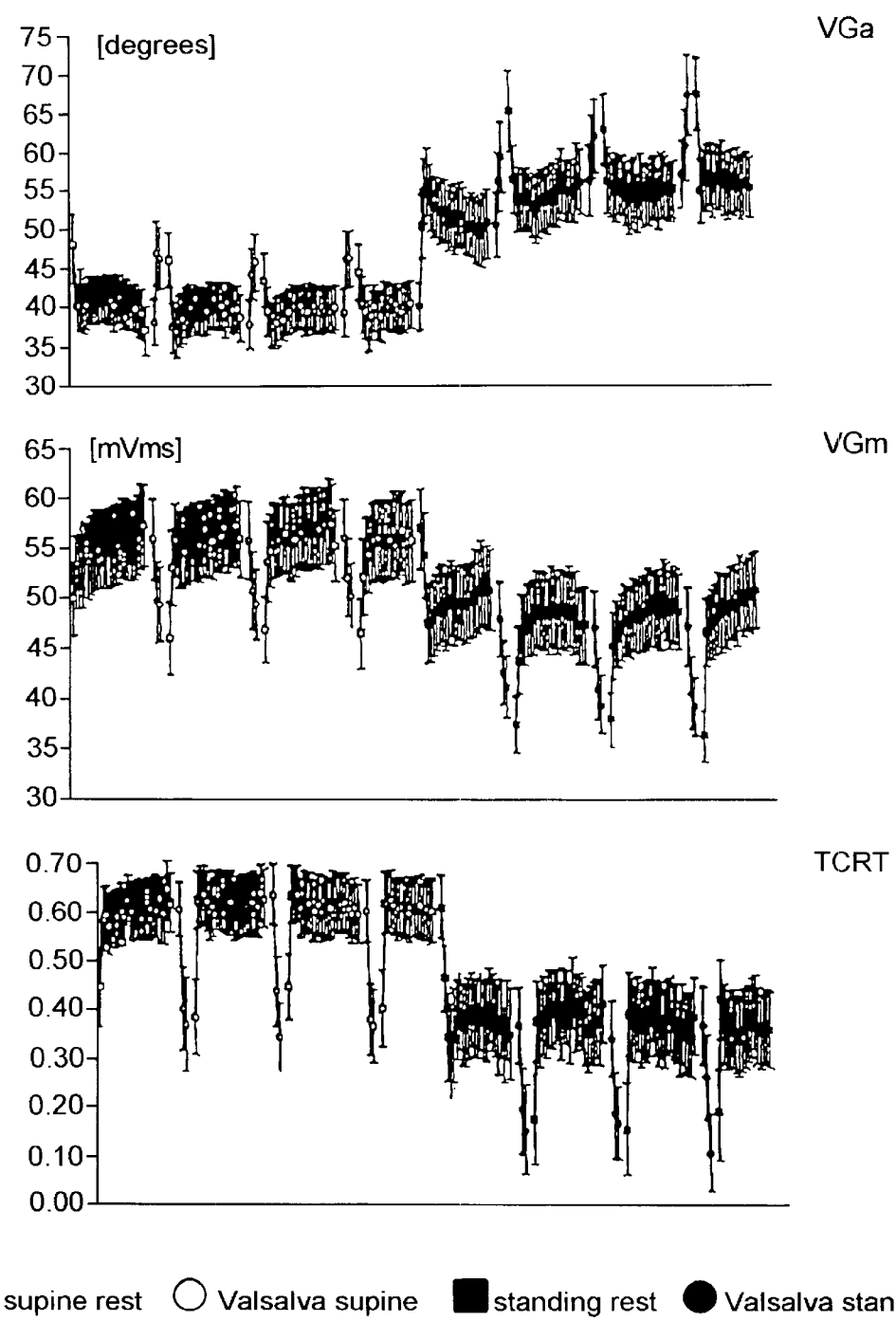
FIGS. 11a and 11b show the variations in descriptor value for ventricular gradient angle, ventricular gradient magnitude, TCRT, RR interval, maximum QT and QT dispersion during Valsalva manoeuvre, each manoeuvre being preformed 3 times in supine position and 3 times in unsupported standing position.
Figure 11B:
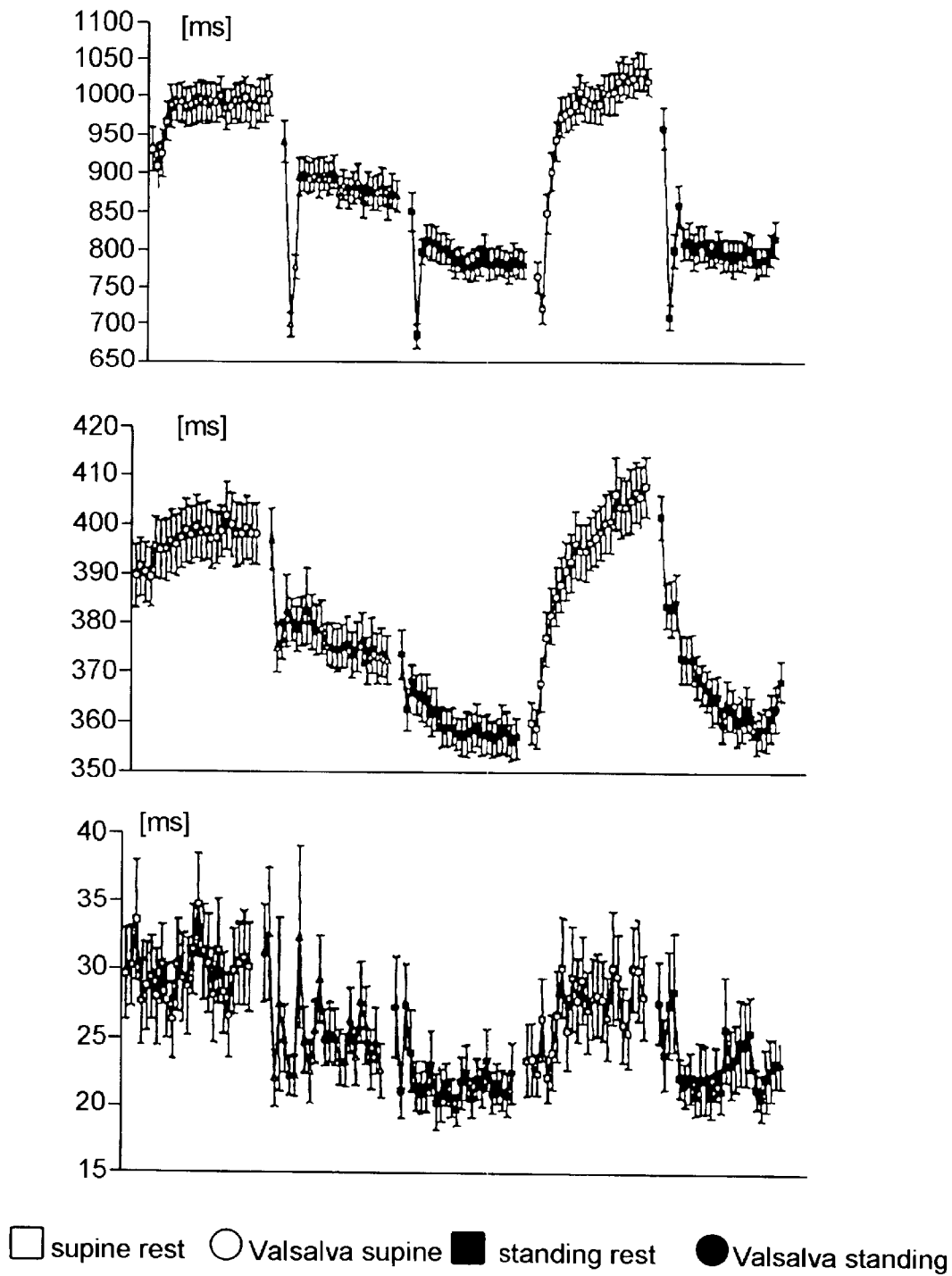

VGa was positively correlated with heart rate (r=−0.39, p=0.026 for the VGa/RR relation). On the other hand, although TCRT and the heart period clearly followed the same trend during postural changes and Valsalva manoeuvre (see FIGS. 10 and 11), there was no correlation between the two parameters during steady state supine position (r=0.09, p=0.61). This suggests that rather than TCRT being driven by the heart rate, both parameters are under the control of a common factor operating during autonomic perturbations but not during steady state resting conditions.

Previous studies have found significant correlation between VG and the heart rate. On the basis of this relation VG found limited use as a sensor for rate-adaptive pacing. The gradient is increased by an increase in pacing rate, and is decreased by exercise or other stress during fixed rate ventricular pacing. Thus, at least in theory, the gradient can be implemented in a closed loop rate-adaptive feedback system: the gradient is decreased by physical or emotional stress, which leads to increase of the pacing rate (at a controllable speed) and the latter increases the gradient to the resting level. The gradient was measured by the time integral (the area) under the evoked R wave. Important limitations of the VG measured in this way prevented the wide-spread use of VG as a rate-responsive sensor: although it is a rapidly responding sensor, the maximum pacing rate is reached very early during exercise, so the proportionality of the rate-response is very moderate. The ventricular gradient is also directly related to the ventricular mass and thickness; therefore changes in the ventricular geometry in upright posture may lead to paradoxical changes in heart rate.

The data from this study suggest that the role of VG and especially of TCRT as rate-responsive sensors in implantable antiarrhythmic devices, and possibly also for automatic detection of potentially arrhythmogenic autonomic modulations are potential applications of these descriptors. To achieve this in a commercial product, it may be necessary to make certain modifications such as simplyfying the measurement algorithm of TCRT and to calculate it from intracardiac leads instead of standard surface leads.

In some recent studies it was found that the beat-to-beat variability of the VG was significantly increased by myocardial ischemia (see, for example Horinaka S, Yamamoto H, Tabuchi T, Takada M, Akabane T, Onoda M, Yagi S. Ventricular gradient variability. New ECG method for detection of ischemic heart disease. J Electrocardiol 1995; 28:177–183; and Horinaka S, Yamamoto H. Enhancement of ventricular gradient variability during acute myocardial ischemia. Int J Cardiol 1998; 65:173–180). In another recent study it was found that an abnormal T wave axis in either the frontal or horizontal plane was a strong and independent predictor of fatal and non-fatal cardiac events in the general population older than 55 years. TCRT is able to observe such an abnormal T-wave axis.

From the results of this study, it was found that the maximum QT interval followed the changes of heart rate during postural changes and was significantly decreased in sitting compared to supine position and was further decreased in standing position. Although statistically significant, the changes of several milliseconds of QT max in standing position by Valsalva and handgrip are hardly of any clinical significance.

Although QT dispersion was significantly decreased in sitting and further in standing position compared to supine, the values are largely overlapping. It has been shown in the past that QT dispersion was significantly increased in standing compared to supine position in patients with syndrome X, while in one study a significant effect of posture on QT dispersion in healthy subjects was not found. The low reproducibility of both automatic and manual measurement of the QT dispersion is well documented.

The role of the autonomic nervous system in ventricular arrhythmogenesis has recently been heavily investigated (see, for example, La Rovere M T, Bigger Jr J T, Marcus F I, Mortara A, Schwartz P J. Baroreflex sensitivity and heart rate variability in prediction of total cardiac mortality after myocardial infarction. Lancet 1988; 351:478–484; Hohnloser S H, Klingenheben T, Loo A, Hablawetz E, Just H, Schwartz P J. Reflex versus tonic vagal activity as a prognostic parameter in patients with sustained ventricular tachycardia or ventricular fibrillation. Circulation 1994; 89:1068–1073; and Schmidt G, Malik M, Barthel P, Schneider R, Ulm K, Rolnitzky L, Camm A J, Bigger Jr J T, Schömig A. Hear-rate turbulence after ventricular premature beats as a predictor of mortality after acute myocardial infarction. Lancet 1999; 353:1390–1396). The autonomic modulations of the dynamicity of ventricular repolarisation have been shown to contain diagnostic and prognostic information (see, for example, Maison-Blanche P, Coumel P. Changes in Repolarization Dynamicity and the Assessment of the Arrhythmic Risk. PACE 1997; 20[Pt.II]:2614–2624; Nollo G, Speramza G, Grasso R, Bonamini R, Mangiardi L, Antolini R. Spontaneous beat-to-beat variability of the ventricular repolarisation duration. J Electrocardiol 1992; 25:9–17; Sandrone G, Torzillo D, Fundaro C, Porta A, Danna P, Polese A, Malliani A, Lombardi F. Spectral Analysis of RR and R-T Variabilities in Patients with Coronary Artery Disease. A. N. E. 1998; 3(3):237–243; Gang Yi, Xiao-Hua Guo, Reardon M, Gallagher M M, Hnatkova K, Camm A J, Malik M. Circadian Variation of the QT Interval in Patients With Sudden Cardiac Death After Myocardial Infarction. Am J Cardiol 1998; 81:950–956; and Homs E, Marti V, Guindo J, Laguna P, Vinolas X, Caminal P, Elosua R, Bayés de Luna A. Automatic Measurement of corrected QT interval in Holter recordings: Comparison of its dynamic behaviour in patients after myocardial infarction with and without life-threatening arrhythmias. Am Heart J 1997;134:181–7. However, the clinical value of many approaches to the assessment of the repolarisation dynamicity is unclear. Reliable descriptors to detect and quantify the autonomic modulations of ventricular repolarisation, would be extremely useful. The sensitivity of VG and of the new decriptor TCRT for detecting autonomic modulations, could be translated into prognostic power for major cardiac events. As mentioned above, the preliminary results indicate that such use of these descriptors is certainly possible.

The conclusion from this study was that both VG and TCRT are superior to QT max and QTd in detecting autonomic modulations of myocardial repolarisation induced by postural changes and Valsalva manoeuvre. The sensitivity of TCRT and the dynamicity of its reaction to postural and autonomic modulations suggest that it would have particularly useful application for rate-adaptive sensors in implantable antiarrhythmic devices. Given its measurement could be simplified and made possible from itracardiac leads it could be used for automatic detection of autonomic modulation of ventricular repolarisation or other potentially arrythmogenic factors in implantable devices.

There now follows a description of preferred implantable devices, such as a pacemaker (see FIGS. 12 to 14) and a pacemaker cardioverter-defibrillator (see FIGS. 15 and 16), which could use TCRT to improve pacing to act as a monitor for detecting ventricular repolarisation abnormalities or even act as an alarm to warn of autonomic conditions that pose a risk to the patient.

Figure 12:
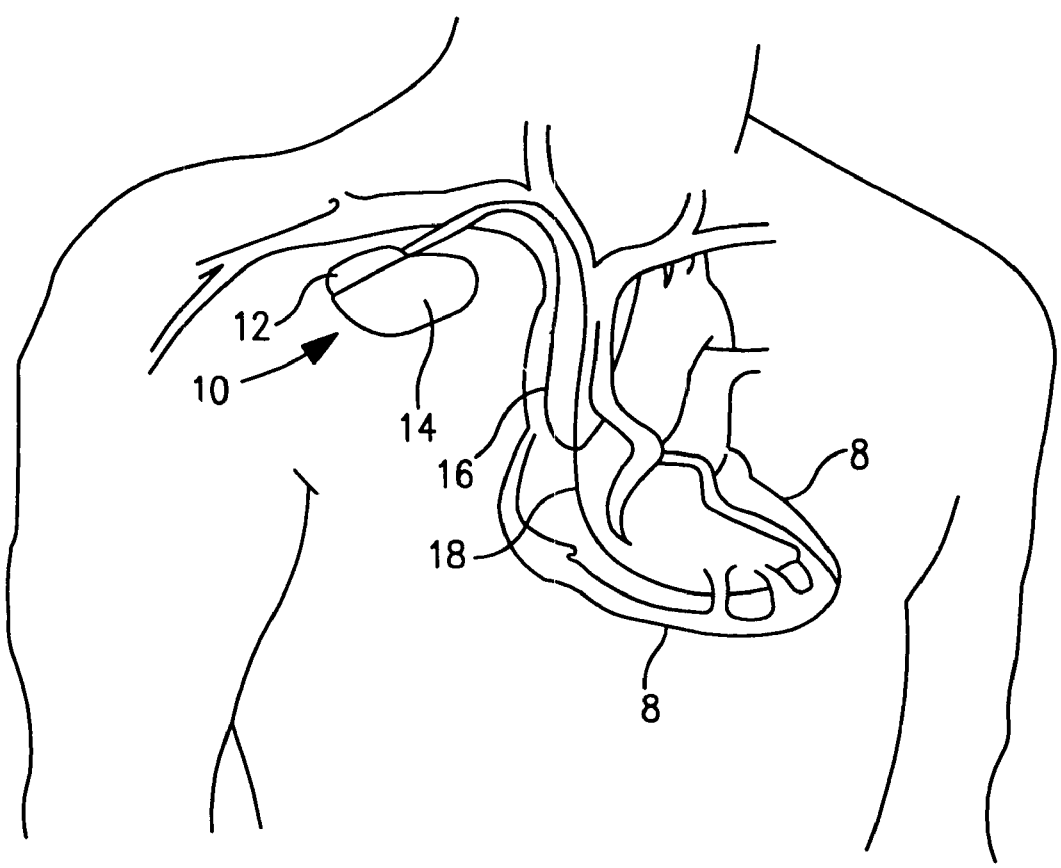
FIG. 12 shows an implantable device positioned within the human body.

FIG. 12 is a simplified schematic view of one embodiment of an implantable medical device ("IMI") 10 of the present invention. IMD 10 shown in FIG. 12 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IME 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 13:
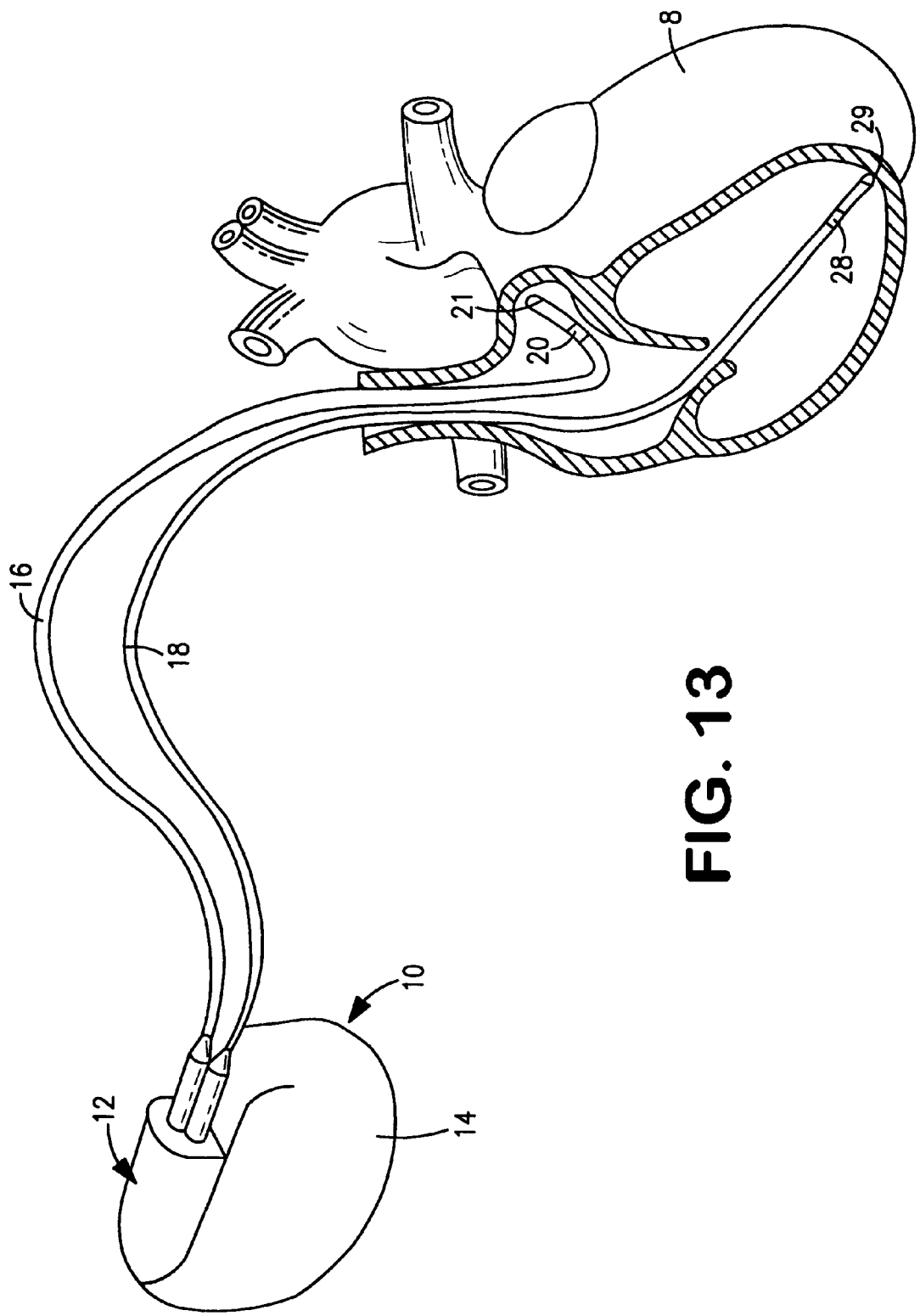
FIG. 13 shows a perspective view of a preferred pacemaker.

FIG. 13 shows connector header module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 14:
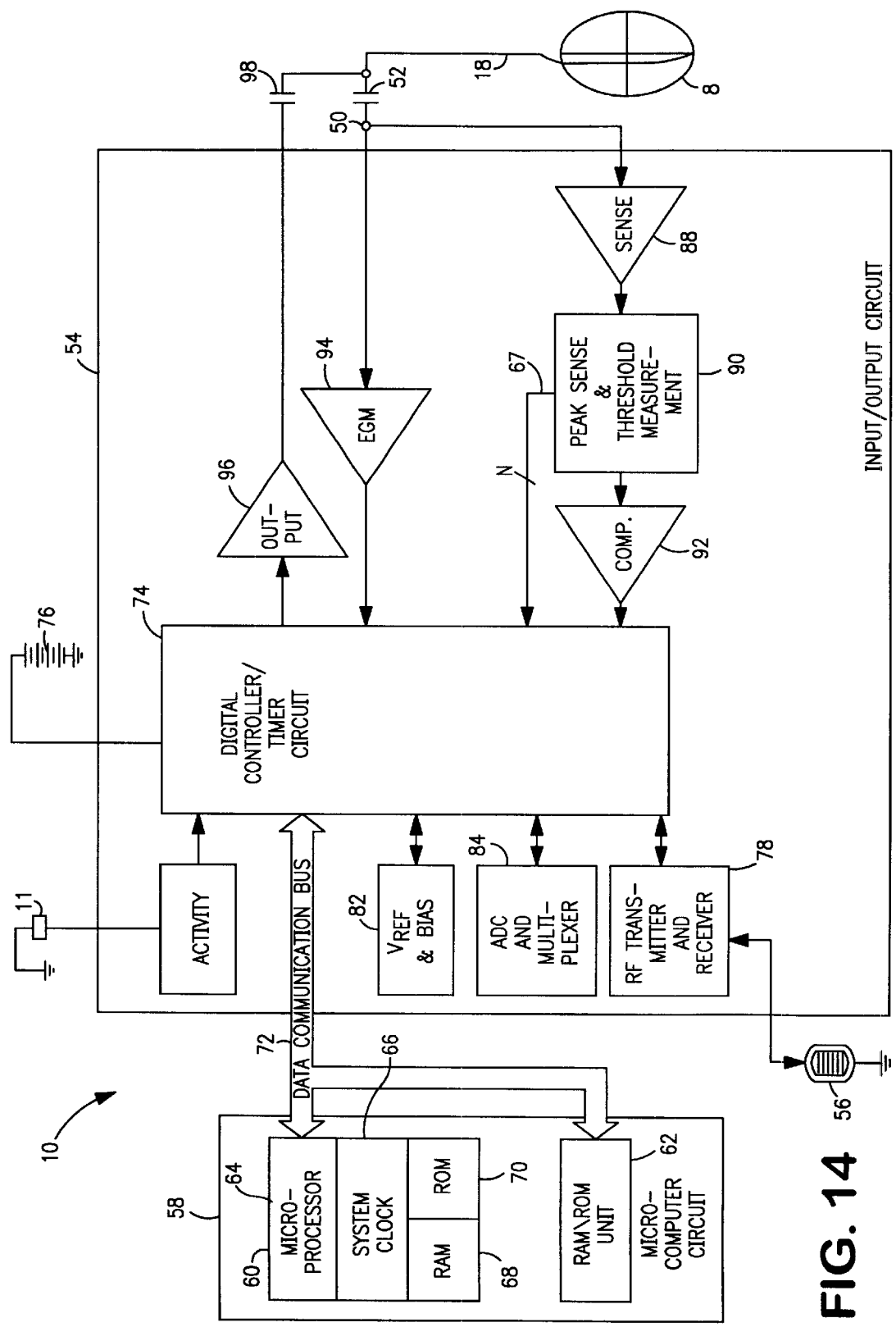
FIG. 14 shows a circuit diagram suitable for operating the pacemaker of FIG. 13.

FIG. 14 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. Additional information based on the patient's autonomic tone could be provided here to improve the pacing. For the sake of convenience, IMD 10 in FIG. 14 is shown with lead 18 only connected thereto; similar circuitry and connections not explicitly shown in FIG. 14 apply to lead 16.

IMD 10 in FIG. 14 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 14, lead 18 is coupled to node 50 in IME 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 14 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 14, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier (output pulse generator) 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. One such response could be generated through measurement of TCRT. This could be in response to changes in the autonomic tone of the patient or changes in direction of the repolarisation wavefront. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 15:
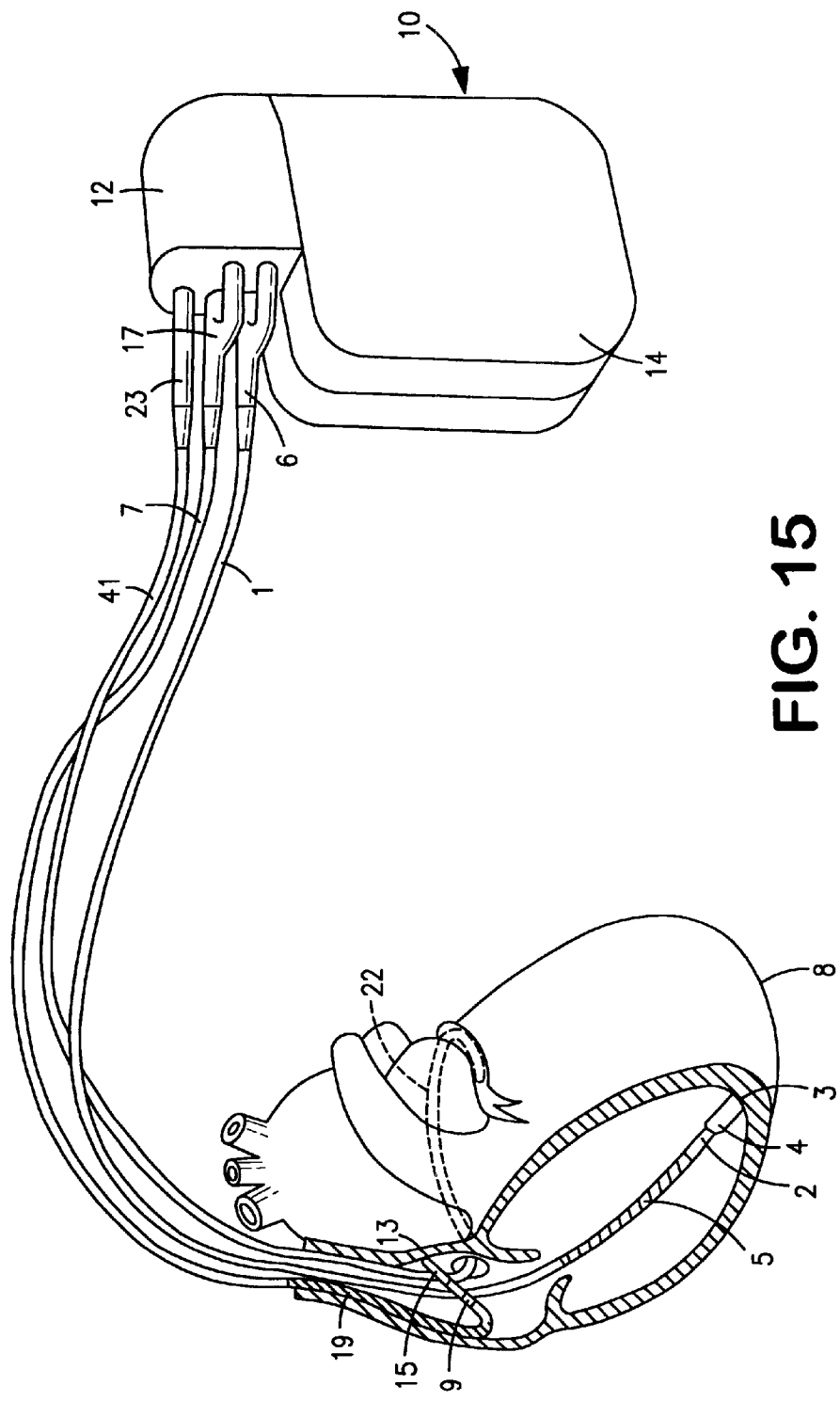
FIG. 15 shows a perspective view of a preferred pacemaker-cardioverter-defibrillator.
Figure 16:
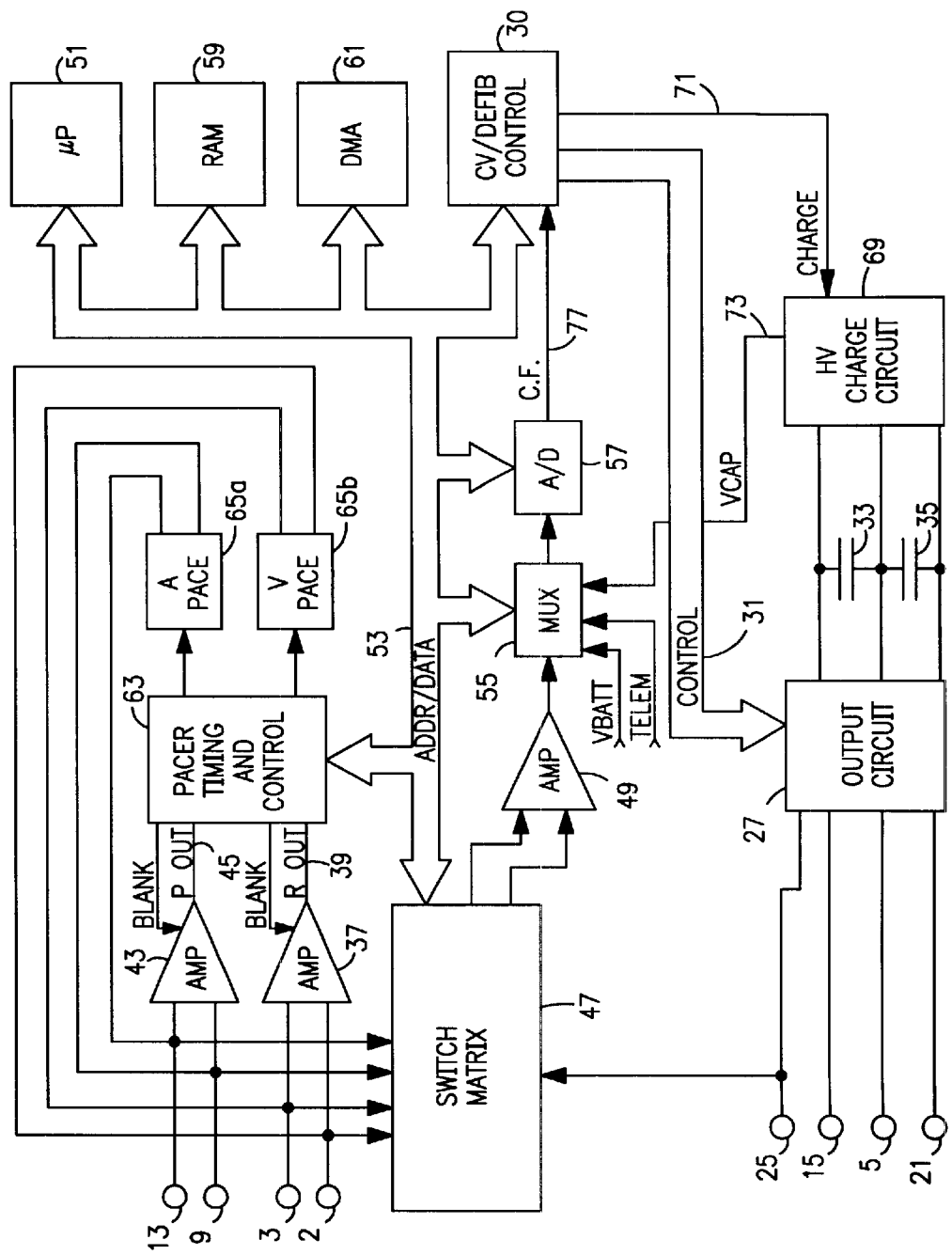
FIG. 16 shows a circuit diagram suitable for operating the pacemaker of FIG. 16.

FIGS. 15 and 16 illustrate one embodiment of IMD 10 and a corresponding lead set of the present invention, where IMD 10 is a PCD. In FIG. 15, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode (elongated coil electrode) 5 may be fabricated from platinum, platinum alloy or other materials known to be usable in implantable defibrillation electrodes and may be about 5 cm in length.

The atrial/SVC lead shown in FIG. 15 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 15 assumes the form of a coronary sinus lead disclosed in the above cited '838 patent issued to Bardy, and includes elongated insulative lead body 41 carrying one coiled conductor coupled to an elongated coiled defibrillation electrode 22. Electrode 22, illustrated in broken outline in FIG. 15, is located within the coronary sinus and great vein of the heart. At the proximal end of the lead is connector plug 23 carrying an electrical connector 41 coupled to the coiled conductor. The coronary sinus/great vein electrode 22 may be about 5 cm in length.

Implantable PCD 10 is shown in FIG. 15 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 15 may be practiced in conjunction with the present invention, such as those shown in U.S. Pat. No. 5,690,686 to Min et al., hereby incorporated by reference herein in its entirety.

FIG. 16 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 15 is employed, the correspondence to the illustrated electrodes is as follows. Electrode 25 in FIG. 16 includes the uninsulated portion of the housing of PCD 10. Electrodes 25, 13, 21 and 5 are coupled to high voltage output circuit 27, which includes high voltage switches controlled by CV/defib control logic 30 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier (wide band amplifier) 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art. For example, TCRT could be calculated and output signals generated accordingly.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65a and 65b, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms such as TCRT. Conventionally the presence of an atrial or ventricular tachyarrhythmia is confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 30, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 16, delivery of cardioversion or defibrillation pulses is accomplished by output circuit 27 under the control of control circuitry 30 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

As shown in FIGS. 12 to 16, conventional implantable devices 10 have several electrodes that could be used for recording depolarisation and repolarisation signals for the purposes of determining TCRT or other descriptor value. For example, in the IMD 10 of FIG. 13 signals could be recorded between the atrial tip electrode 21 and the ventricular tip electrode 29, between the atrial tip electrode 21 and the IMD ("can") 10 and between the ventricular tip electrode 29 and the IMD 10. Other electrodes could be placed on the IMD 10, or within the heart 8 or remote from the heart connected via additional leads. The signals recorded in three or more directions could be processed to calculate vectors describing the progress of the depolarisation and repolarisation wavefronts. Microprocessor 51 could be used to transform the vectors into an optimum dimensional space and descriptors such as TCRT and TMD could be determined. More complicated IMDs, for example, a pacemaker-cardioverter-defibrillator, would have an additional lead or leads from which further data could be extracted. The "InSync" implantable cardio defibrillator (ICD) which is sold by Medtronic, could record data between any two points of the ICD, SVC, three electrodes in the right ventricle, the left ventricle electrode and two atrial electrodes. It is desirable to extract the wavefront data from existing leads to avoid further obstructions being introduced into the heart pathways, for example, through the presence of extra leads or thicker leads. In addition, the fewer the number of components, the less likely it is that the device will go wrong.

In another embodiment, additional electrodes could be positioned on the patient corresponding with the or some of the standard independent ECG leads. Information from these could be fed to the IMD 10 for controlling pacing in response to autonomic changes or the detection of ventricular repolarisation abnormalities. In a further embodiment, the leads of an IMD 10 could be used to provide data which is fed to external monitoring equipment. This might be in the form of a possible device which the patient wears so that the patient can be warned when TCRT values are at dangerous levels as a result of autonomic changes, for example, during exercise.

In another embodiment, the IMD 10 may record the data with respect to time which is then fed to an external data processing system for analysis, for example, during a check up. Such data may provide early indications of heart problems in addition to that being treated by the implantable device 10. These might include ischemia and other conditions where damage to the heart muscle is caused which affect the direction of the repolarisation wavefront, change the autonomic tone or the response of the autonomic system.

The descriptor TCRT could be calculated and used by itself in such situations or the ECG data could be processed further to extract additional descriptor values, which together with TCRT may provide a better diagnosis tool.

In one embodiment envisaged in the present invention, a descriptor such as TCRT or TMD, or a combination of descriptors, may be used to control a drug delivery mechanism. This may be by way of an implantable device or possibly via external equipment, for example, when the patient is in an intensive care unit. Such drugs may be used to reduce clotting of blood (e.g. asprin) or perhaps reduce the stress levels in the patient. Sympathetic and parasympathetic agents could also be administered. Where no correction of symptoms is observed, alarms could be triggered and assistance summoned.

As mentioned above, TCRT has been found to provide a useful measure of the autonomic tone in the patient. Nearly all anaesthetic agents create a sympathetic or a parasympathetic effect in the autonomic system of a patient. It would therefore be useful for the autonomic response of the patient to be tested prior to being anethetised. TCRT could be monitored while a patient performs Valsalva manoeuvre (or some other standard test) to check the autonomic response, prior to being anethetised for surgery.

A third case study was carried to investigate whether QT dispersion could represent properly interlead heterogeneity of ventricular repolarisation. The results obtained were compared to determine the extent that the non-dipolar components of an ECG differ from the dipolar components, i.e. the residual energy of the T wave was investigated. The study was as follows:

The concept of the so-called QT dispersion has recently attracted significant attention from the clinical research community. Various methods have been proposed to evaluate QT dispersion from the standard 12 lead electrocardiogram (ECG) by measuring QT intervals in individual leads. Most frequently, the simple range of the QT interval measurements is used. There are numerous studies indicating the clinical value of QT dispersion. Among others, increased QT dispersion has been reported to be associated with QT interval prolongation due to drugs of known proarrhythmic properties and to be less increased on drugs with lesser proarrhythmic effects, to predict mortality in general epidemiological studies to identify patients who are at greater risk after surviving acute myocardial infaretion and to mark therapeutic efficacy in the idiopathic long QT syndrome. Recently, however, reports have also appeared challenging the clinical usefulness of QT dispersion.

Since the introduction of the concept of QT dispersion, it has been speculated that the increased range of QT interval measurements is caused by the regional heterogeneity of the duration of ventricular repolarisation. It has been proposed that different leads of the standard 12-lead ECG project the repolarisation signals of different regions of the myocardial tissue and that, consequently, increased dispersion is a sign of regional differences in the duration of repolarisation. Indeed, studies comparing the QT dispersion with the dispersion of these duration of monophasic action potentials found a general correlation supporting this hypothesis. It was observed that QT dispersion is increasingly prolonged with increasing differences in the duration of monophasic action potentials recorded at different endocardial sites.

At the same time, these studies do not offer direct proof that increased dispersion of the QT intervals in the standard 12-lead ECGs measures directly the same phenomena as the dispersion of durations of monophasic action potentials. If an increased heterogeneity exists in the durations of monophasic action potentials, the repolarisation sequence is more disturbed, the vectorcardiographic loop of the T wave is more abnormal and the projections of this loop into the standard ECG leads are more complicated than in normal electrocardiograms.

Recent studies have shown that a similar value of QT dispersion is recorded in full 12-lead ECGs and in their reconstruction from orthogonal XYZ leads and that QT dispersion values correlate with parameters of the vectorcardiographic T loop morphology. It has consequently been speculated that the different projections of the T wave vector onto the different leads of the standard ECG play an essential role, and that the hypothesis of QT dispersion representing a direct measure of the heterogeneity of ventricular repolarisation durations is flawed. Such a concept can explain even the earlier observations of the correlation of QT dispersion with the heterogeneity of monophasic action potential durations. However, the studies of orthogonally reconstructed 12-lead ECGs and of correlations with T loop morphology only prove that the projections of the T wave vector play an important role in determining QT dispersion but they do not prove that a regional heterogeneity of myocardial repolarisation duration is not involved at all.

To solve the problem of whether QT dispersion is, or is not, associated with regional heterogeneity of myocardial repolarisation, potentially in addition to the T wave vector projection, a direct study was conducted comparing QT dispersion with electrocardiographic signals that are not attributable to the orthogonal vector of the T wave. In 12-lead ECGs obtained from several clinically well defined populations, QT dispersion and, using special signal processing techniques, the extent of non-dipolar components by which the individuals leads of a 12-lead ECG differ from the 3-D vector of the repolarisation signals were measured.

The study involved four separate groups of subjects.

The group of normal subjects consisted of 78 normal healthy volunteers (aged 47±16 years, 23 women) with normal physical examination and normal 12-lead ECG. At the time of the study, none of the normal subjects was on any medication and on the day of the study, the subjects were asked to refrain from smoking and from alcohol and caffeine intake.

The group of hypertrophic cardiomyopathy (HCM) patients consisted of 68 patients (mean age 38±15 years, 21 women) referred to St George's Hospital London, England, for diagnosis, risk stratification, management of symptoms, and/or follow-up evaluation. Following the established guidelines, the diagnosis of HCM was based on the presence of left ventricular hypertrophy on 2D echocardiography in the absence of other cardiac or systemic disease that may cause left ventricular hypertrophy. For ethical reasons, patients were not required to discontinue therapy before this study. At the time of the study, 9 patients were on medication with established or potential effects on myocardial repolarisation (amiodarone, n=6; and sotalol, n=3).

The group of idiopathic dilated cardiomyopathy (DCM) patients consisted of 72 patients (mean age 48±15 years, 29 women). The diagnosis of idiopathic DCM was based on enlarged left ventricular diameters (left ventricular diameters: diastolic 64±10 mm, systolic 51±13 mm) with reduced systolic function without any underlying causes of DCM. At the time of the recording, 16 patients were on amiodarone.

Finally, the group of patients with acute myocardial infaretion (AMI) consisted of 81 patients (mean age 63±12 years, 20 women). Diagnosis of acute myocardial infaretion was based on previously published criteria, i.e. the presence of at least 2 of 3 standard signs of (a) typical chest pain, (b) cardiac enzymes elevated more than twice above to normal levels of our laboratory, and (c) typical ECG changes. History of previous myocardial infaretion was recorded in 13 patients, 44 patients had an anterior infaretion, and at the time of hospital admission, 68 patients received thrombolytic therapy. At the time of the study, none of the patients was on an antiarrhythmic therapy, 80 patients were receiving aspirin, 43 beta-blockers, 32 diuretics, and 34 ACE inhibitors.

In the patient groups, subjects were not eligible for this study if in atrial fibrillation or other non-sinus rhythm, in the presence of atrioventricular conduction block, or with a QRS duration>120 ms.

In each subject of each group, 10 serial 12-lead ECGs were recorded in a supine resting position using a digital 12-lead electrocardiograph MAC VU by Marquette Medical Systems (Milwaukee, Wis.). Each ECG recorded simultaneously all 12-leads for 10 seconds and the serial ECGs were performed one after another without removing the electrodes. In all subjects, all 10 ECGs were recorded within less than 3 min.

All ECGs were recorded after careful skin preparation. The healthy subjects were recorded after being instructed to refrain from smoking and caffeine intake on the day of the study. HCM and DCM patients were recorded at the time of presentation at a specialised out-patient clinic of our Hospital. The AMI patients were recorded on day 1 following the index infaretion.

Each ECG was stored on a floppy disc (500 Hz sampling at 12 bit resolution) and transferred to a dedicated workstation equipped with the QT Guard package (Marquette Medical Systems) which was used to construct the so-called median beat of each lead of each electrocardiogram. These median beats represent an ideal QRST complex of each lead of the ECG and, compared to the native ECG signal, have an improved signal to noise ratio. The median beats were further used to measure the QT dispersion and the non-dipolar components of each ECG.

In each electrocardiogram, QT dispersion was measured using the QT Guard package. In each lead of each ECG, the noise of the isoelectric line was measured and compared with the voltage of the peak of the T wave. If the standard deviation of the T-P segment signal did not exceed 70% of the maximum T wave amplitude and if the T wave amplitude was >60 mV, the lead was measured, otherwise it was excluded from the measurement. In each lead, the end of T wave was firstly determined automatically using the intersection of the isoelectric line with the tangent to the inflection point of the descending part of the T wave. (The tangent was calculated using least square fit to the 3 samples above and 3 samples below the inflection point.) These automatic measurements were subjected to visual checks by an experienced and electrocardiographically trained operator who corrected the automatic measurements manually when necessary. During the editing process, the operator was kept blinded with respect to the association of the ECGs with the individual groups in the study though clinical ECG diagnosis was possible in a number of cases.

An ECG was accepted for the QT dispersion measurement if the T wave offset was measured in at least 9 of the 12 standard leads. In such a case, QT dispersion was expressed using three different methods: as the range of the QT interval durations in all measured leads (that is the difference between the maximum and minimum QT interval measured–QTd method 1), as the standard deviation of the QT interval durations in all measurable leads (QTd method 2), and as the difference between the upper and lower quartile of the QT interval durations in all measurable leads (QTd method 3). Methods 2 and 3 for expressing QT dispersion were used in an attempt to overcome the technical problems associated with the simple measurement of QT interval range. In addition to these measures of QT dispersion, maximum QT interval was taken as the maximum of the QT intervals of all measurable leads. Heart rate was also derived from each ECG.

For each method of QT dispersion measurement, the results obtained in the serial electrocardiograms of the same subject were averaged and the mean value was used as the true measure of QT dispersion for the given individual. The representative values of maximum QT interval and of heart rate were obtained for each subject in the same way.

The concept attributing QT dispersion to the regional differences of myocardial repolarisation assumes that in addition to the global T wave vector, each lead of the 12-lead ECG records signals from a region of the heart (nearest to the electrode in case of the precordial leads) which are not recorded by any other lead. To quantify the presence of such signals, we have measured the non-dipolar components of the 12-lead ECG, i.e. the extent of the residuum of the T wave which exists after subtracting the T wave vector.

More specifically, using the technique described above, in relation to the first study, the signals from the eight independent leads of the 12-lead ECG (namely leads I, II, V1, V2, . . . , V6) were subjected to the Singular Value Decomposition and the electrocardiogram reconstructed in an orthogonal 8-lead system. In such a system, the first lead contained the maximum energy in one single direction, the second lead the maximum energy perpendicular to the first lead, the third lead, the maximum energy perpendicular to the first two leads, etc. In this way, the energy embedded in the first three orthogonal leads corresponded to the energy of the T wave vector while the energy in the remaining leads 4–8 corresponded to the non-dipolar components summed over all 12-leads of the original ECG (see FIG. 2a which illustrates the recorded ECG signals and FIG. 2b which illustrates those signals when they are reconstructed using Singular Value Decomposition). The Singular Value Decomposition is dependent on the region of the ECG signal for which the optimisation of the orthogonal leads is performed.

For the purposes of this study, we have optimised the Singular Value Decomposition for the T wave rather than for the QRS complex.

For each ECG, the proportion between the non-dipolar components in orthogonal leads 4–8 and (that is the time integral of leads 4–8 within the T wave) and the energy of the T wave vector in leads 1–3 (that is the time integral of leads 1–3 of the optimised orthogonal system of over the same time) was obtained. Similar to the measurement of QT dispersion, these values obtained from the serial ECGs in each subject were averaged and the result taken as the true measure of the non-dipolar component.

For the purposes of this study, we term the proportion between the non-dipolar and 3D vector components "the relative T wave residuum".

Subjects were excluded if at least 5 of the 10 serial ECGs either did not provide QT dispersion measurement based on the acceptance criteria as above, or were rejected by the singular value decomposition package because of low signal to noise ratio or other technical reasons.

The values of heart rate, Fridericia corrected maximum QT interval (QTc), QT dispersion and of the relative T wave residuum were compared in individual groups of the study. Since the distribution of the values of the relative T wave residua is not known, the non-parametric two tail, two sample Mann-Whitney test was used for this purpose. The correspondence between QT dispersion and T wave residua was examined using Spearman rank correlation coefficients which were calculated for the complete study as well as for the individual clinically defined populations. In the same way, the correspondence between T wave residua and heart rate and QTc interval were evaluated.

Unless specified otherwise, the data in tables are presented as mean±standard deviation while in whisker charts, data are presented as mean±standard error of the mean. A p value less than 0.05 was considered statistically significant.

For ECG processing reasons (mainly for T waves of too low amplitude in too many leads), 5 HCM patients and 10 DCM patients were excluded from the analysis. In the remaining subjects (78 normal volunteers, 63 HCM patients, 62 DCM patients, and 81 AMI patients), fewer than all serial ECGs were used in 3 DCM, 1 HCM, and 2 AMI patients.

Figure 17B:
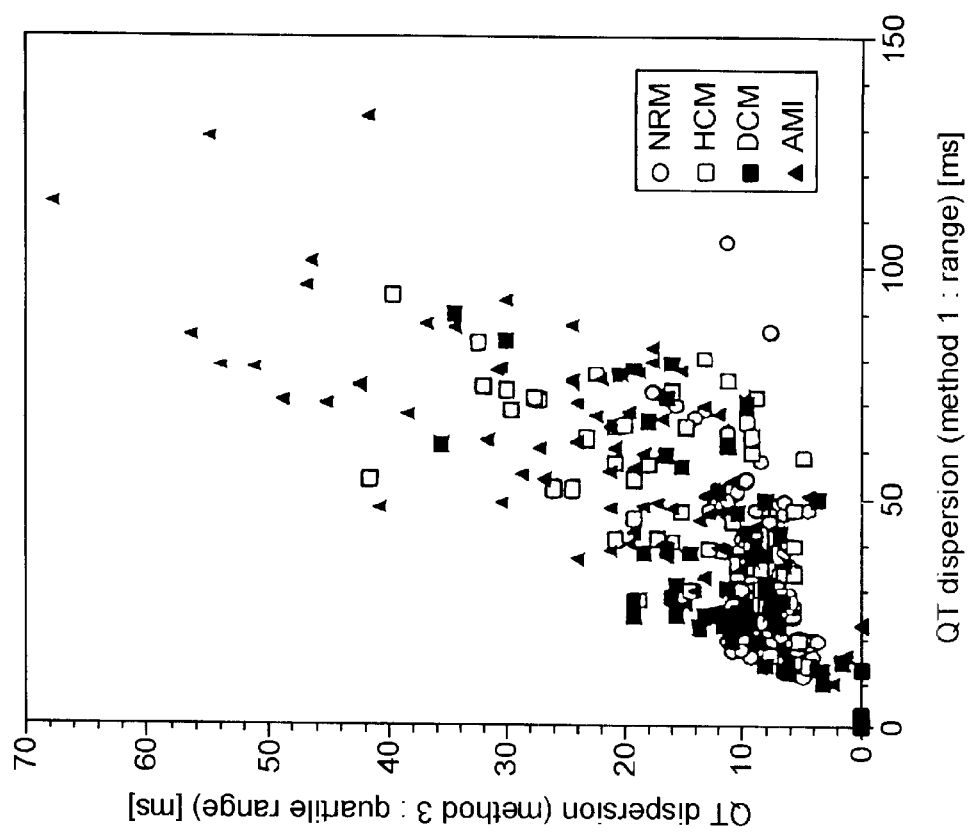
FIGS. 17a and 17b show scatter diagrams of QT dispersion values, where QTd Method 1=range of measurable QT intervals, QTd Method 2=standard deviation of measurable QT intervals, and QTd Method 3=inter-quartile difference of measurable QT intervals.
Figure 17A:
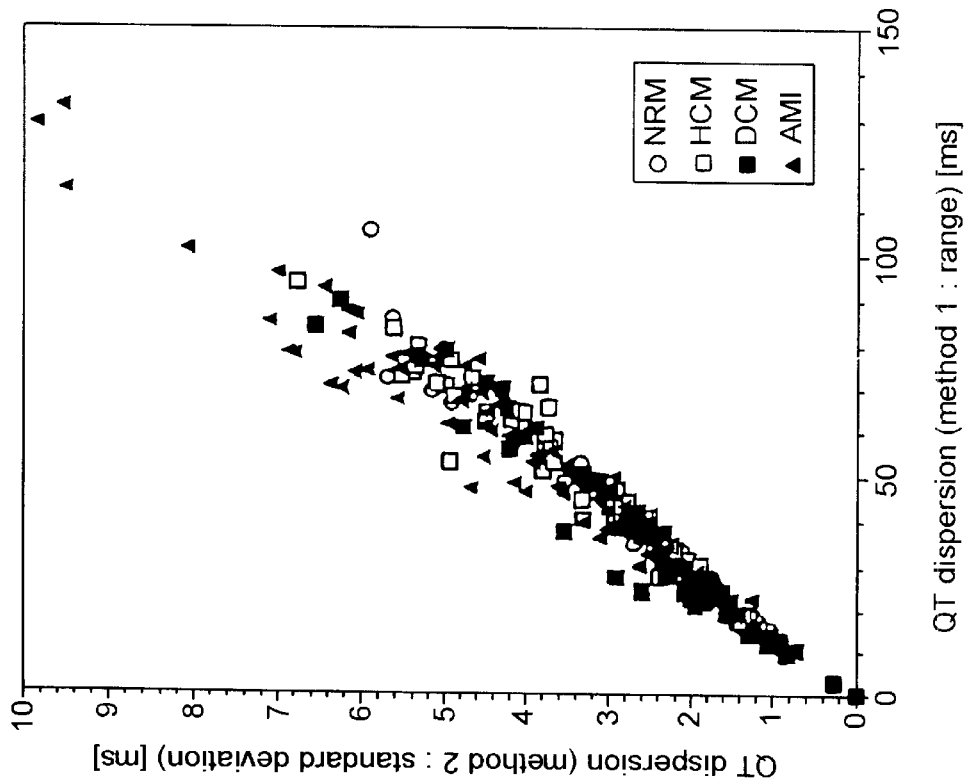

Table 7 shows the correlation coefficients between the individual methods for expressing QT dispersion. While Method 1 (range) was very closely correlated with Method 2 (standard deviation), Method 3 (inter-quartile difference) leads to a somewhat less close correlation although the relationship remains very strong and very statistically significant (FIGS. 17a and 17b).

Figure 18B:
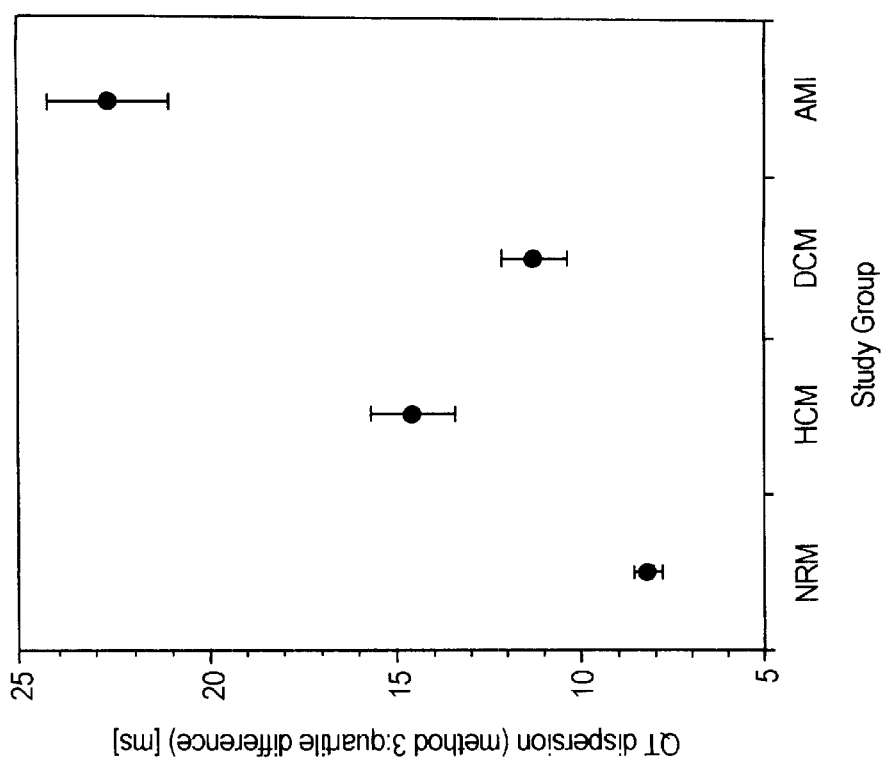
FIGS. 18a and 18b show QTd Method 1 and QTd Method 2 results displayed with respect to the clinical group of the subjects.
Figure 18A:
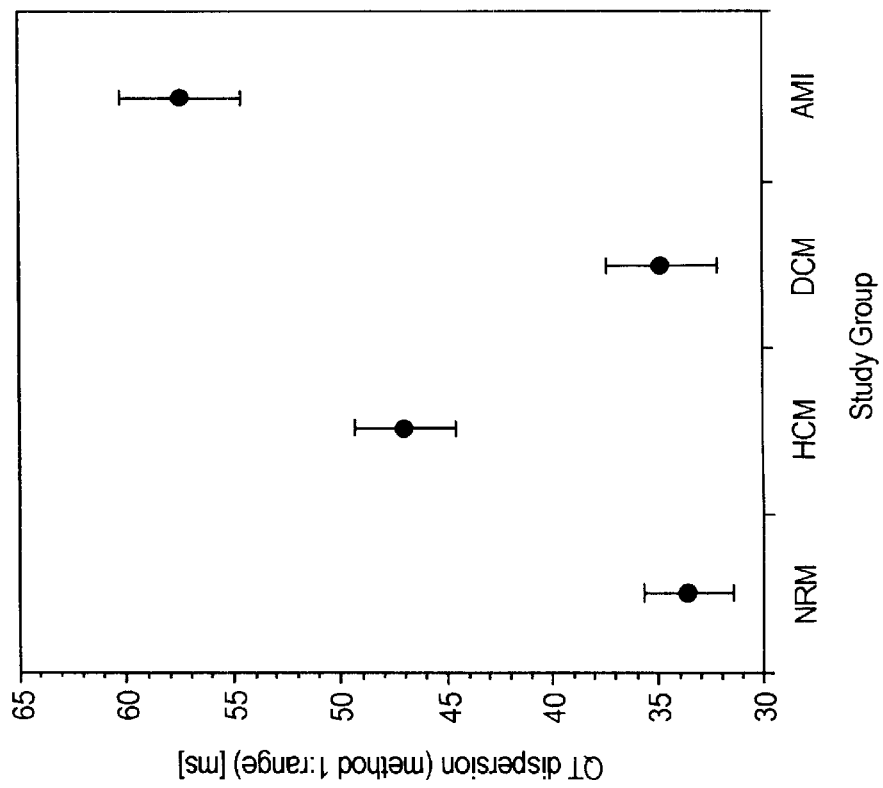

Table 8 shows the differences between the study populations in respect of heart rate and QTc interval. FIGS. 18a and 18b shows the values of QT dispersion (Method 1 and Method 3) in the four populations of the study. With Method 3 (inter-quartile range), all the differences between individual pairs of populations were statistically significant or nearly statistically significant. However, Method 1 (range of QT intervals) and Method 2 (standard deviation) did not differentiate between normal subjects and DCM patients (p=0.92 and p=0.35 for Method 1 and Method 2, respectively). Note that the results for Method 2 of QT dispersion are not shown in the figure—although numerically different, the values practically reproduced the comparisons with Method 1.

TABLE 7

Correlation coefficients between QT dispersion indices

| Group | QTd 1 vs QTd 2 | QTd 1 vs QTd 3 | QTd 2 vs QTd 3 |
| --- | --- | --- | --- |
| NRM | 0.9824 | 0.4136 | 0.4889 |
| HCM | 0.9689 | 0.6677 | 0.7725 |
| DCM | 0.9576 | 0.6437 | 0.7529 |
| AMI | 0.9655 | 0.7772 | 0.8685 |
| Total population | 0.9812 | 0.7212 | 0.7942 |

QTd 1=range of measurable QT intervals, QTd 2=standard deviation of measurable QT intervals, QTd 3=inter-quartile difference of measurable QT intervals. NRM=normal healthy volunteers, HCM=hypertrophic cardiomyopathy patients, DCM=idiopathic dilated cardiomyopathy patients, AMI=survivors of acute myocardial infarction.

TABLE 8

Comparisons between heart rate and QTc interval durations in study groups

| Group | Heart rate (bpm) | QTc interval (ms) |
| --- | --- | --- |
| NRM | 66.7 ± 9.4 | 406.5 ± 17.7 |
| HCM | 67.6 ± 12.9 | 447.2 ± 26.5 |
| DCM | 76.0 ± 13.0 | 429.4 ± 35.3 |
| AMI | 74.1 ± 14.7 | 441.1 ± 33.8 |

All differences between heart rate in individual groups were statistically significant with the exception of normal subjects vs HCM patients, DCM vs AMI patients. All differences between QTc interval were statistically significant with the exception of HCM vs AMI patients. NRM= normal healthy volunteers, HCM=hypertrophic cardiomyopathy patients, DCM=idiopathic dilated cardiomyopathy patients, AMI=survivors of acute myocardial infaretion. bpm=beats per minute.

Figure 19:
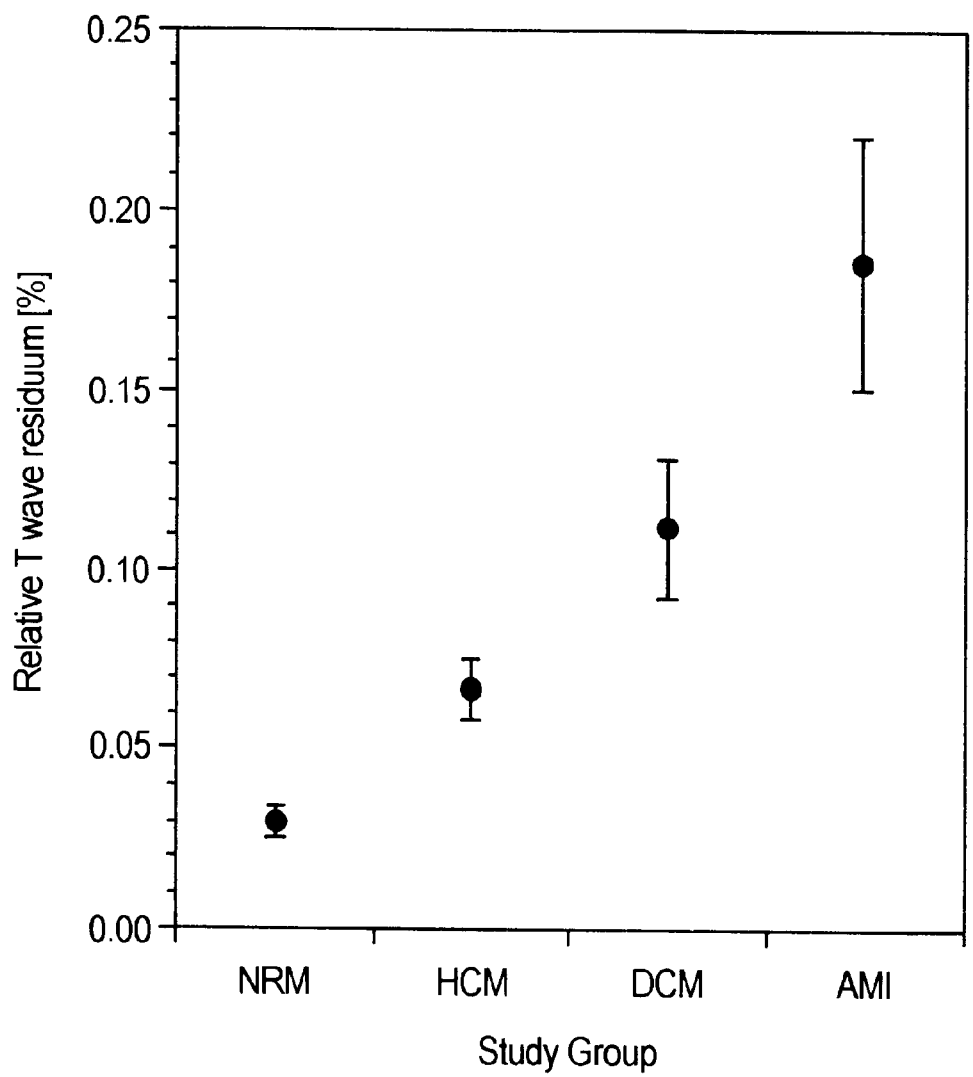
FIG. 19 shows the relative T wave residuum plotted with respect to the clinical group of the subject.

FIG. 19 shows the values of the relative T wave residua in the individual populations of the study. With the exception of the difference between normal subjects and HCM patients (p=0.14), all the differences between individual populations were statistically significant. It should be noted that the values of the relative T wave residuum are very small, the mean value in normal healthy subjects being approximately 0.03% which means that in the normal subjects, we have found the proportion between non-dipolar and dipolar components of the T wave in the order of 3 in 10,000.

The correlations between the relative T wave residua and the measures of QT dispersion is presented in Table 9. Corresponding scatter diagrams are shown in FIGS. 20a and 20b. In individual populations of the study, statistical significance of the correlation between relative T wave residua and QT dispersion was only reached in HCM patients. Note that in the DCM and HCM populations, an opposite relationship between QT dispersion and relative T wave residua was observed. Statistical significance of the correlation was reached in the total population of the study almost certainly because of similar trends from normal subjects to AMI patients.

Correlation coefficients of the relative T wave residua with heart rate and maximum QTc interval are also shown in Table 9. Similar to the measures of QT dispersion, the residuum is related neither to heart rate nor to the QTc interval.

The findings of this third case study may be summarised as follows:
a) The non-dipolar components, (i.e. electrocardiographic regional heterogeneity) of the repolarisation signals are measurable in digital 12-lead ECGs.
b) These non-dipolar components differ in different clinically well-defined groups.
c) The so-called QT dispersion is unrelated to the non-dipolar components of the T wave. Consequently, QT dispersion does not represent a direct measure of regional heterogeneity of ventricular repolarisation.

The study, together with previously published shows that QT dispersion may relate to nothing more than an expression of T wave loop abnormalities, rather than T wave loop morphology. Although technically more difficult to quantify, the morphology of the T wave loop appears to be a far valuable ECG factor.

In the study it was observed that the relative T wave residuum differs between different clinically well defined groups of our study. T wave residuum may be useful clinically as a diagnostic tool, either on its own, or more preferably, in conjunction with other descriptors which

TABLE 9

Correlation coefficients between QT dispersion and relative T wave residuum

| Group | QTd1 vs Twr | QTd2 vs Twr | QTd3 vs Twr | HR vs Twr | QTc vs Twr |
| --- | --- | --- | --- | --- | --- |
| NRM | −0.0446 | −0.0945 | −0.0811 | 0.0794 | 0.2193 |
|  | NS | NS | NS | NS | NS |
| HCM | 0.2805 | 0.2882 | 0.3305 | −0.2027 | 0.1322 |
|  | P = 0.026 | P = 0.022 | P = 0.008 | NS | NS |
| DCM | −0.1531 | −0.1755 | −0.2201 | −0.0873 | −0.0317 |
|  | NS | NS | NS | NS | NS |
| AMI | 0.0771 | 0.0445 | 0.0393 | 0.1054 | 0.2807 |
|  | NS | NS | NS | NS | P = 0.011 |
| Total population | 0.2165 | 0.2380 | 0.2982 | 0.0135 | 0.3270 |
|  | p = 0.00026 | p = 6 × 10$^{-5}$ | P = 3 × 10$^{-7}$ | NS | P = 2 × 10$^{-8}$ |

QTd 1 = range of measurable QT intervals,
QTd 2 = standard deviation of measurable QT intervals,
QTd 3 = inter-quartile difference of measurable QWT intervals.
HR = heart rate,
QTc = Fridericia corrected maximum QT interval.
Twr = relative T wave residuum.
NRM = normal healthy volunteers,
HCM = hypertrophic cardiomyopathy patients,
DCM = idiopathic dilated cardiomyopathy patients,
AMI = survivors of acute myocardial infarction.

The findings of this study shows that QT dispersion is largely caused by the different projection of the T wave vector in different leads of the standard ECG. These findings also show a significant difference between QT dispersion in groups with a different morphology of the vectorcardiographic T wave loop. Also, this is the first study to show that in addition to the projection effects of the T wave vector, no regional components of signal repolarisation play a role in determining QT dispersion.

This case study does not disprove the clinical utility of QT dispersion. Indeed, the large number of clinical studies showing the potential of QT dispersion are consistent with the hypothesis that patients at greater risk (e.g. patients on proarrhythmic therapy or patients with advanced ischaemic heart disease liable to ventricular tachycardia/fibrillation) have a more complex T wave vector and therefore a more complex projection of the T wave vector into the individual ECG leads. Perhaps, practical aspects of QT dispersion measurement also play a role. More complex patterns of the ECG repolarisation signals may clearly lead to increased difficulty with determining the end of the T wave and may consequently result in the measurement of an increased QT dispersion. If this is the case, the more complex projections of the T wave vector are combined with a systematic bias towards increased QT dispersion values in patients with disturbed ventricular repolarisation. The studies reporting poor intra- and inter-observer reproducibility and poor intra-subject stability of QT dispersion assessment point in this direction. One study found not only increased QT dispersion in HCM patients compared to normals but also a lower reproducibility of QT dispersion measurement in these patients.

could indicate certain heart conditions. It is possible to take the view that the relative T wave residuum truly corresponds to the local heterogeneity in ventricular repolarisation.

What is claimed is:

1. A method of characterising ventricular operation of a patient's heart, comprising sensing a plurality of electrical signals heart from different spatial positions with respect to the heart during depolarisation and repolarisation of the patient's heart, the plurality of electrical signals monitoring the propagation of depolarisation and repolarisation waves originating in the patient's heart, processing the plurality of electrical signals to yield a vector which describes the propagation direction of one of the depolarisation and repolarisation wavefronts, and a set of a plurality of vectors which describe the propagation direction of the other of the depolarisation and repolarisation wavefronts with respect to time, and determining the vector deviation between the depolarisation and repolarisation wavefronts by measuring the angle between pairs of respective vectors for all combinations of depolarisation vector to repolarisation vector between predetermined time limits, wherein the cosine of the angle between each depolarisation/repolarisation vector pair is calculated.

2. A method as in claim 1, wherein angles are measured between a vector for the repolarisation wave, which corresponds to a direction of maximum energy of the repolarisation wave, and each vector from a set of vectors describing the depolarisation wave at different time instances, the set of vectors corresponding to substantially the whole duration of depolarisation of the patient's heart.

3. A method as in claim 1 or 2, wherein the mean cosine of the angle is calculated for all depolarisation/repolarisation vector pairs.

4. A method of characterising ventricular operation of a patient's heart, comprising sensing the propagation of depolarisation and repolarisation waves originating in the heart, determining vectors which are representative of the direction of the wavefronts of the depolarisation and repolarisation waves, and determining the vector deviation between the depolarisation and repolarisation vectors by determining the cosine of the angle between the vectors describing the depolarisation and repolarisation wavefronts, wherein the vector deviation is a function of:

a) the cosine of the angle between two vectors, each vector describing one of the depolarisation and repolarisation wavefronts;

d) the cosines of the angles between a vector describing either the depolarisation or repolarisation wavefront and a set of vectors describing the other of the depolarisation or repolarisation wavefront for a plurality of time instances; or e) the cosines of the angles between a set of vectors describing the depolarisation wavefront for a plurality of lime instances and a set of vectors describing the repolarisation wavefront for a plurality of time instances.

5. A method as in claim 4, wherein data is produced for the propagation of the depolarisation and repolarisation wave with respect to a first set of axes, the data is transformed to a new set of axes defining an optimised orthogonal domain having a first axis aligned with a direction of maximum energy for depolarisation or repolarisation and wherein the vector deviation is measured in the optimised orthogonal domain.

6. A method of characterising ventricular operation of a patient's heart, comprising sensing a plurality of electrical signals from different spatial positions with respect to the heart during depolarisation and repolarisation of the heart, the plurality of electrical signals being sensed by an implantable medical device and being associated with the propagation of depolarisation and repolarisation waves originating from a patient's heart, processing the electrical signals to yield a plurality of vectors which describe the propagation direction of a wavefront for a depolarisation wave and a plurality of vectors which describe the propagation direction of a wavefront for a repolarisation wave, wherein ventricular operation is characterised in terms of the cosine of the angle between the plurality of vectors for the depolarisation and repolarisation waves, wherein at least one of the plurality of vectors describes the propagation of the wavefront as a function of time and the mean of the cosine of the angle between pairs of vectors is determined.

7. An implantable medical device comprising a plurality of medical electrical leads, the leads having electrodes for sensing electrical signals from different spatial positions in, on or near a patient's heart, wherein the device processes the electrical signals to yield directions of propagation for depolarisation and repolarisation waves of a patients heart, calculates the angle of deviation between the depolarisation and repolarisation waves, and generates an output signal corresponding to the angle of deviation, wherein the output signal varies in accordance with the cosine of the angle of deviation.

8. A device as in claim 7, wherein the angle of deviation between the depolarisation and repolarisation waves is calculated with respect to time and the output signal varies in accordance with the mean of the cosine of the angle of deviation for a plurality of time instances.

9. A device as in claim 8, wherein the output signal varies in accordance with the mean of a set of cosine values for the angle of deviation between the direction of the repolarisation wavefront for a maximum energy value and the direction of the depolarisation wavefront as a function of time for all time instances between start and finish points of depolarisation.

10. A device as in any of claim 7, 8, or 9, wherein the output signal is used for at least one of:

g) control pacing of the patient's heart;

h) monitor the condition of the patient's heart;

i) monitor the progression of disease in the patient's heart;

j) raise an alarm when the angle is outside predetermined limits;

k) control a drug dispensing pump; and/or l) monitor the response of the patient's autonomic system.

11. A device as in any of claims 7 through 10, wherein the device is selected from the group of pacemaker, cardioverter, defibrillator, pacemaker-cardioverter-defibrillator, heart monitor and drug dispensing pump.

12. A device as in any of claims 7 through 11, wherein additional electrical signals are sensed by:

d) at least one electrode provided on a housing of the device;

e) at least one subcutaneous electrode; and/or f) at least one external electrode that is applied to a patient's body.

13. A device as in claim 12, wherein the at least one electrode is coupled to the device by a medical electrical lead, by an electrical connection or by a radio frequency transmitter.

14. A method of characterising ventricular operation, comprising sensing a plurality of electrical signals associated with the propagation of a repolarisation wave originating in the patient's heart, the plurality of electrical signals being sensed from different spatial positions on, in or near the patient's heart, processing the plurality of electrical signals to yield a plurality of vectors that are representative of the wavefront of the repolarisation wave, and determining a measure of the spatial variation of the repolarisation wavefront, wherein the spatial variation is calculated by determining vector contributions for the repolarisation wavefront in each of a set of predetermined directions and measuring the angle between pairs of vector contributions.

15. A method as in claim 14, wherein the pre-determined directions correspond with at least three of the standard ECG channels of I, II, V1, V2, V3, V4, V5 and V6, and preferably the vector contribution for the ECG channel of V1 is ignored in the calculation.

16. A method of characterising ventricular operation of a patient's heart, comprising sensing a plurality of electrical signals to monitor repolarisation of the heart from different spatial positions with respect to the patients heart, processing the plurality of signals to yield a vector describing the propagation of a repolarisation wave through the heart, projecting the vector onto a set of axes to determine vector contributions of the signal vector in the directions of the axes, and measuring the angle between pairs of vector contributions, wherein the vector corresponds to a direction of maximum energy of the repolarisation wave.

17. A method of characterising ventricular operation of a patient's heart comprising sensing a plurality of electrical signals to monitor propagation of repolarisation through the heart from different spatial positions with respect to the patient's heart, processing the plurality of electrical signals to yield a vector describing the propagation of a repolarisation wave with respect to time and with respect to a first set of axes defining an optimum domain space, mapping the path of a tip of the vector in the optimum domain space to generate a T-wave loop and calculating a parameter describing the morphology variation of that loop, wherein the parameter is determined by projecting the T-wave loop on to reconstruction vectors corresponding to electrode positions to generate vector contributions in those electrode directions, and determining the angle between all pairs of vector contributions.

18. A method as in claim 17, wherein the reconstruction vectors correspond to the position of at least three of the standard ECG leads of I, II, V1, V2, V3, V4, V5 and V6, and preferably the vector contribution from the standard ECG lead of V1 is ignored in the calculation.

19. A method as in any of claim 17 or 18, wherein the T-wave loop is mapped in two orthogonal dimensions and the energy of the T-wave loop in the two orthogonal dimensions is equalised prior to calculating said parameter.

20. A method of characterising ventricular operation of a patient's heart comprising sensing a plurality of electrical signals associated with the propagation of a repolarisation wave originating in the patient's heart from different spatial positions with respect to the patient's heart, processing the plurality of electrical signals to yield a vector which is representative of the wavefront of the repolarisation wave with respect to a first set of axes, transforming the vector to a second set of axes defining an optimised orthogonal domain having a first axis aligned with a direction of maximum energy, the domain comprising three dimensions representing the dipolar components of the repolarisation wavefront vector and at least one further dimension representing the non-dipolar components of the repolarisation wavefront vector and determining the energy of the non-dipolar components, wherein said optimised orthogonal domain has eight dimensions and the transformed repolarisation wavefront vector S has eight components $s_1$ to $s_8$ corresponding one to each dimension, wherein the vector components are ranked in order of most significance with respect to energy and the non-dipolar components are represented by the fourth to eighth components $s_4$ to $s_8$.

21. A method as in claim 20, wherein the energy of the non-dipolar components is determined for a portion of the repolarisation wave corresponding to a particular region of the heart muscle.

22. A method as claimed in any of claim 1, 3, 4, 5, 6, 14, 15, 16, 17, 19, 20 or 21, wherein the plurality of electrical signals are measured from electrodes positioned in different spatial positions corresponding to the standard ECG leads of I, II, V1, V2, V3, V4, V5 and V6.

23. A method of detecting whether a patient is healthy or sick, wherein more than one parameter characterising ventricular operation as claimed in any of claim 1, 3, 4, 5, 6, 14, 15, 16, 17, 19, 20, 21, 33 or 22 is calculated.

24. A method of detecting abnormalities of ventricular repolarisation in a patient using a method of characterising ventricular operation as claimed in any of claim 1, 3, 4, 5, 6, 14, 15, 16, 17, 19, 20, 21, 33 or 22, wherein preferably said method is a method of detecting the onset of ischemia.

25. A method of determining whether a patient is suffering from heart failure, and preferably a method of determining whether the patient is suffering from one of hypertropic cardiomyopathy, idiopathic dilated cardiomyopathy and acute myocardial infarction, comprising measuring a parameter characterising ventricular operation as claimed in any of claim 1, 3, 4, 5, 6, 14, 15, 16, 17, 19, 20, 21, 33 or 22, wherein preferably the method is accomplished by employing an implantable medical device which is capable of sensing depolarisation and repolarisation waves, and processing same.

26. A method of categorising subjects using a method of characterising ventricular operation as claimed in any of claim 1, 3, 4, 5, 6, 14, 15, 16, 17, 19, 20, 21, 33 or 22.

27. A method of monitoring the autonomic system of a subject, wherein a method of characterising ventricular operation as claimed in any of claim 1, 3, 4, 5, 6, 14, 15, 16, 17, 19, 20, 21, 33 or 22, is used to measure changes in the autonomic system of the subject, wherein the method is accomplished by employing an implantable medical device which is capable of sensing depolarisation and repolarisation waves and processing same.

28. A method as in claim 27, wherein changes in the autonomic system of the patient are measured to:

f) monitor the progress of a disease in a subject;

g) monitor the influence of drugs on the autonomic system of a subject;

h) control the rate of pacing for a pacemaker;

i) control a drug dispensing pump and/or j) test the response of the autonomic system of a subject.

29. A method as in claim 28, wherein changes in the autonomic system of the patient are measured while the patient executes a predetermined procedure to effect a change in autonomic system, wherein preferably the autonomic system is measured while Valsalva manoeuvre is performed by the patient and/or while a set of postural changes are executed by the patient.

30. A method of determining depolarisation start and end points for measuring characteristics of a signals representing changes in energy during depolarisation of a patient's heart, comprising finding a first peak in the energy of the signal corresponding to depolarisation of the patient's heart, determining a point in time, $t_{RP}$, corresponding to the peak energy and determining the maximum energy $E_{Rmax}$ of the signal at that point, determining a point in time $t'_{RS}$ before $t_{RP}$ and a point in time $t'_{RE}$ after $t_{RP}$ where the energy of the signal drops to a predetermined percentage of the maximum energy, determining the depolarisation start point by subtracting a first predetermined time interval from time $t'_{RS}$ and determining the depolarisation end point by adding a second predetermined time interval to time $t'_{RE}$.

31. A method as claimed in claim 30, wherein said predetermined percentage of the maximum energy $E_{Rmax}$ is in range of 50 to 90% of $E_{Rmax}$, preferably in the range of 60 to 80% of $E_{Rmax}$, and most preferably 70% of $E_{Rmax}$.

32. A method as claimed in claim 31, wherein said first and second predetermined time intervals are in the range of 38 to 58 msec, preferably in the range of 43 to 53 msec, and most preferably 48 msec.

33. A method of determining repolarisation start and end points for a signal representing changes in energy during depolarisation and repolarisation of a patient's heart, comprising:

finding a first peak in the energy of the signal corresponding to depolarisation of the patient's heart, determining the maximum energy $E_{Rmax}$ of the signal at the peak and determining a point in time $t'_{RE}$ where the energy of signal has dropped to a predetermined percentage of $E_{Rmax}$, finding the next peak in the signal energy corresponding to repolarisation and determining the point in time $t_{TP}$ where that peak occurs, determining the repolarisation start point as a predetermined fraction of the time interval between $t'_{RE}$ and $t_{TP}$;

determining the repolarisation end point by determining a vector $s_{2D}(t_i)$ which describes the repolarisation wavefront as projected on to a plane spanned by two orthogonal vectors $u_1$ and $u_2$ which represent the maximum energy and next most energy of the repolarisation wave in two orthogonal directions for $t_i \geq t_{TS}$, the vector having a tip which defines a path on said plane, dividing the area defined by the path of the tip of $S_{2D}(t_i)$ in the plane of $u_1$ and $u_2$ into a plurality of equal rectangular cells, assigning a measure $D_i$ to each cell dependent on the time spent by the tip of $s_{2D}(t_i)$ in the $i^{th}$ cell, discarding cells having the measures $D_i=0$ and ordering all other cells in respect of $D_i$, determining a threshold value $D_{th}$ of $D_i$ which is greater than the mean value of $D_i$, and determining the end point of repolarisation $t_{TE}$ as a point at which $D_i \geq D_{th}$.

34. A method as claimed in claim 33, wherein said predetermined fraction of the time interval between $t'_{RE}$ and $t_{TP}$ is in the range ¼ to ½ preferably said predetermined fraction of the time interval between $t'_{RE}$ and $t_{TP}$ is □.

35. A method as claimed in any of claim 1, 3, 4, 5, 6, 14, 15, 16, 17, 19, 20, 21 or 33 wherein data from the electrical signals is decomposed into an optimum domain space using singular value decomposition.

36. A system for measuring characteristics of ventricular operation of patient's heart in accordance with any of the methods of claim 1, 3, 4, 5, 6, 14, 15, 16, 17, 19, 20, 21, 33 or 22, comprising a plurality of electrodes for sensing a plurality of electrical signals in different spatial positions in, on or near to a patient's heart to monitor the propagation of depolarisation and repolarisation waves originating in the patient's heart, a microprocessor for processing the plurality of electrical signals to determine a characteristic of ventricular operation, and an indicator to convey the value of the measured characteristic, or condition of the patient's autonomic system, to an observer, wherein preferably the indicator is a visual display and/or an audible alarm.

37. A system as in claim 36, wherein the system senses the plurality of electrical signals via:

e) at least one electrode attached to a medical electrical lead of an implantable medical device selected from the group of pacemaker, cardioverter, defibrillator, pacemaker-cardioverter-defibrillator and heart monitor which is implanted within the subject's body;

f) at least one electrode provided on a housing of an implantable medical device;

g) at least one subcutaneous electrode; and/or h) at least one external electrode applied to the patient's body.

38. A system as in any of claim 36 or 37, wherein the system has eight electrodes which correspond to the standard electrode positions of I, II, V1, V2, V3, V4, V5 and V6.

39. An implantable medical device which measures characteristics of ventricular operation of a patient's heart in accordance with any of the methods of claim 1, 3, 4, 5, 6, 14, 15, 16, 17, 19, 20, 21, 33 or 22, comprising a plurality of electrodes for sensing a plurality of electrical signals in different spatial positions in, on or near to a patient's heart to monitor the propagation of depolarisation and repolarisation waves originating in the patients heart, and a microprocessor for processing the plurality of electrical signals to measure a characteristic of ventricular operation, and to generate an output signal corresponding to said measured characteristic.

40. An apparatus as in claim 39, wherein the apparatus is at least one of:

f) a pacemaker or pacemaker-cardioverter-defibrillator having a pacing rate which is controlled in response to the calculated characteristic of ventricular operation;

g) a cardioverter or a defibrillator, the operation of which is controlled in response to the calculated characteristic of ventricular operation;

h) a monitor for detecting abnormalities in ventricular repolarisation, the device preferably being able to trigger a warning signal when the calculated characteristic of ventricular operation is within certain limits;

i) a monitor for measuring changes in the autonomic system of a subject, the device preferably being able to trigger a warning signal when the calculated characteristic of ventricular operation is within certain limits; and/or j) a device for controlling a drug dispensing pump.

41. A computer program, comprising software code portions for performing the method as claimed in any of claim 1, 3, 4, 5, 6, 14, 15, 16, 17, 19, 20, 21, 33 or 22, a computer program product which is directly loadable into the internal memory of a digital computer, comprising software code portions for performing said method, a microprocessor which is programmed with software code portions for performing said method, or a digital computer which is programmed with software code portions for performing said method.

* * * * *

UNITED STATES PATENT AND TRADEMARK OFFICE
CERTIFICATE OF CORRECTION

PATENT NO. : 6,438,409 B1  
APPLICATION NO. : 09/534454  
DATED : August 20, 2002  
INVENTOR(S) : Marek Malik et al.

Page 1 of 1

It is certified that error appears in the above-identified patent and that said Letters Patent is hereby corrected as shown below:

Col. 47, lines 50 and 51, please delete "claim 1, 3, 17, 19" and insert --claims 1-3, 17-19--.
Col. 47, lines 54 and 55, please delete "claim 1, 3, 17, 19" and insert --claims 1-3, 17-19--.
Col. 47, line 63, please delete "claim 1, 3, 17, 19" and insert --claims 1-3, 17-19--.
Col. 48, line 3, please delete "claim 1, 3, 17, 19" and insert --claims 1-3, 17-19--.
Col. 48, lines 6 and 7, please delete "claim 1, 3, 17, 19" and insert --claims 1-3, 17-19--.
Col. 48, line 14, please delete "f)" and insert --a)--.
Col. 48, line 15, please delete "g)" and insert --b)--.
Col. 48, line 17, please delete "h)" and insert --c)--.
Col. 48, line 18, please delete "i)" and insert --d)--.
Col. 48, line 19, please delete "j)" and insert --e)--.
Col. 46, line 6, please delete "claim" and insert --claims--.
Col. 44, line 65, please delete "claim" and insert --claims--.
Col. 49, lines 17 and 18, please delete "claim 1, 3, 17, 19" and insert --claims 1-3, 17-19--.
Col. 49, line 23, please delete "claim 1, 3, 17, 19" and insert --claims 1-3, 17-19--.
Cal. 49, line 36, please delete "e)" and insert --a)--.
Col. 49, line 41, please delete "f)" and insert --b)--.
Col. 49, line 43, please delete "g)" and insert --c)--.
Col. 49, line 44, please delete "h)" and insert --d)--.
Col. 50, line 1, please delete "claim" and insert --claims--.
Col. 50, lines 6 and 7, please delete "claim 1, 3, 17, 19" and insert --claims 1-3, 17-19--.
Col. 50, line 36, please delete "claim 1, 3, 17, 19" and insert --claims 1-3, 17-19--.

Signed and Sealed this

Twelfth Day of June, 2007

JON W. DUDAS  
*Director of the United States Patent and Trademark Office*